US005817757A

United States Patent [19]
Adams et al.

[11] Patent Number: 5,817,757
[45] Date of Patent: Oct. 6, 1998

[54] INHIBITORS OF PEPTIDE BINDING TO MHO CLASS II PROTEINS

[75] Inventors: Alan D. Adams, Crawford; A. Brian Jones, Scotch Plains; Victoria K. Lombardo, Belle Mead; Richard L. Tolman, Warren, all of N.J.

[73] Assignee: Merck & Co., Inc., Rahway, N.J.

[21] Appl. No.: 736,706

[22] Filed: Oct. 28, 1996

Related U.S. Application Data

[60] Provisional application No. 60/008,059, Oct. 30, 1995.
[51] Int. Cl.$^6$ .......................... A61K 38/06; A61K 35/14; A61K 45/00; A61K 39/00
[52] U.S. Cl. ...................... 530/331; 530/380; 424/280.1; 424/278.1; 424/810; 514/18; 514/19
[58] Field of Search ................................. 530/331, 380; 424/278.1, 810; 514/18, 19

[56] References Cited

FOREIGN PATENT DOCUMENTS

| 0 532 466 | 3/1992 | European Pat. Off. . |
|---|---|---|
| WO 88/03022 | 5/1988 | WIPO . |
| WO 96/01646 | 1/1996 | WIPO . |
| WO 96/20215 | 7/1996 | WIPO . |
| WO 96/30035 | 10/1996 | WIPO . |

OTHER PUBLICATIONS

Basak et al., Int. J. Peptide Protein Res., vol. 46 (1995), pp. 228–237, "Peptidyl substrates containing unnatural amino acid at the P'1 position are potent inhibitors of prohormone convertases".
Kroemer et al., J. Med. Chem., vol. 38 (1995), pp. 4917–4928, "3D–Quantitative structure–activity relationships of human immunodeficiency virus type–1 proteinase . . .".
Scholz et al., J. Med. Chem., vol. 37 (1994), pp. 3079–3089, "Inhibitors of HIV–1 proteinase containing 2–heterosubstituted 4–amino–3–hydroxy–5–phenylpentanoic acid . . . ".
Chapman et al., J. Med. Chem., vol. 36 (1993), pp. 4293–4301, "Inhibition of matrix metalloproteinases by N–carboxyalkyl peptides".
Urban et al., FEBS, vol. 298, No. 1 (1992), pp. 9–13, "Reduced–bond tight–binding inhibitors of HIV–1 protease".
Hanson et al., Biorganic & Medicinal Chemistry Letters, vol. 6, No. 16 (1996), pp. 1931–1936, Design of MHC Class II (DR4) ligands using conformationally restricted imino acids at p3 and p5.
Sette et al., J. of Immunol., vol. 151 (1993), pp. 3163–3170, "HLA DR4w4–Binding motifs illustrate the biochemical basis of degeneracy and specificity in peptide–DR interactions".
Rudensky et al., Nature, vol. 359 (1992), pp. 429–431, "Truncation variants of peptides isolated from MHC Class II molecules suggest sequence motifs".

Chicz et al., Nature, vol. 358 (1992), pp. 764–768, "Predominant naturally processed peptides bound to HLA–DR1 are derived from MHC–related molecules and are heterogeneous in size".
Hammer et al., Cell, vol. 74 (1993), pp. 197–203, "Promiscuous and allele–specific anchors in HLA–DR–binding peptides".
Germain et al., Annu. Rev. Immunol., vol. 11 (1993), pp. 403–450, "The biochemistry and cell biology of antigen processing and presentation".
Jorgensen et al., Annu. Rev. Immunol., vol. 10 (1992), pp. 835–873, "Molecular components of T–cell recognition".
Stern et al., Nature, vol. 368 (1994), pp. 215–221, "Crystal structure of the human class II MHC protein HLA–DR1 complexed with an influenza virus peptide".
Hurtenbach et al., J. Exp. Med., vol. 177 (1993), pp. 1499–1504, "Prevention of autoimmune diabetes in non–obese diabetic mice by treatment with a Class II major histocompatibility complex–blocking peptide".
Guery et al., J. Exp. Med., vol. 177 (1993), pp. 1461–1468, "Selective immunosuppression by administration of major histocompatibility complex Class II–binding peptides".
Wauben et al., J. of Immunol. vol. 152 (1994), PP. 4211–4220, "Inhibition of experimental autoimmune encephalomyelitis by MHC Class II binding competitor peptides depends on the relative MHC binding affinity of the disease–inducing peptide".
Gautam et al., J. of Immunol., vol. 148 (1992), pp. 3049–3054, "Inhibition of experimental autoimmune encephalomyelitis by a nonimmunogenic non–self peptide that binds to I–Au1".
Skinner et al., Annals of the Rheumatic Diseases, vol. 53 (1994), pp. 171–177, "Lymphocyte responses to DR ¼ restricted peptides in rheumatoid arthritis".
Hanson et al., Biorganic & Medicinal Chem. Lett., vol. 6, pp. 1931–1936 (1996), "Design of MHC Class II (DR4) ligands using conformationally restricted imino acids at p3 and p5".

(List continued on next page.)

Primary Examiner—Ponnathapura Achutamurthy
Assistant Examiner—Padmashri Ponnaluri
Attorney, Agent, or Firm—Catherine D. Fitch; Melvin Winokur

[57] ABSTRACT

Compounds of the formula are inhibitors of peptide binding to major histocompatibility complex type II proteins and are useful in the treatment and prevention of autoimmune diseases including: rheumatoid arthritis, Type I diabetes, multiple sclerosis, lupus erythematosis, Graves disease and pemphigus. The present invention also provides novel compositions, methods of treatment employing the compounds of the present invention and methods of manufacture of the compounds of structural formula (I).

3 Claims, No Drawings

OTHER PUBLICATIONS

Hammer et al., Proc. Nat'l Acad. Sci. USA, vol. 91, pp. 4456–4460 (1994), "High–affinity binding of short peptides to major histocompatibility complex class II molecules by anchor combinations".

Jones et al., Abstracts of the 25th Nat'l Medicinal Chemistry Symposium, Jun. 18–22, 1996, Ann Arbor, MI., "The development of peptidomimetic inhibitors of the binding of antigenic peptide to MHC Class II".

Adams et al., Abstracts of 25th Nat'l Medicinal Chemistry Symposium, University of Michigan, Ann Arbor, MI, Jun. 18–22, 1996, Abstract No. 98, "The development of small molecule inhibitors of the binding of antigenic peptide to MHC Class II".

Jones et al., Abstracts of the XIVth Int'l Symposium on Medicinal Chemistry, Maastricht, The Netherlands, Sep. 8–12, 1996, "Inhibition of MHC Class II ligation oy peptidomimetics: prospects for antigen specific immunosuppression".

Acton III et al., Tetra. Lett., vol. 37, No. 25, pp. 4319–4322 (1996), "Synthesis and derivatization of a versatile alpha–substituted lactam dipeptide isostere".

Acton, III et al., C&EN, Feb. 19 1996, 211th ACS Natl'l Meeting, New Orleans, Mar. 24–28, 1996, "alpha–Allyl lactam dipeptide isosteres: Synthesis and utility of a versatile intermediate".

Rusiecki et al., Abstracts of the 20th IUPAC Symposium on the Chemistry of Natural Products, Chicago, IL, Sep. 15–20, 1996, "Modular synthesis of tripeptide inhibitos of MHC Class II".

INHIBITORS OF PEPTIDE BINDING TO MHO CLASS II PROTEINS

CROSS-REFERENCE TO RELATED APPLICATIONS

This is a non-provisional application based on Provisional Application Ser. No. 60/008,059, filed Oct. 30, 1995.

FIELD OF THE INVENTION

The present invention provides novel compounds, novel compositions, methods of their use and methods of their manufacture, where such compounds may be pharmacologically useful as agents in therapies whose mechanism of action rely on the inhibition of peptide binding to major histocompatibility complex (MHC) class II molecules, and more particularly useful in therapies for the treatment and prevention of autoimmune diseases.

BACKGROUND OF THE INVENTION

A basic function of the immune system is to distinguish self from non-self, an activity carried out primarily by T cells. Failure of mechanisms which control the tolerance of T cells to self antigens and the prevention of activation of T cells by self antigens may lead to autoimmunity. In individuals afflicted with autoimmune diseases, an increased frequency of alleles for specific human leukocyte antigens (HLAs) are found, and it is believed that the disease-associated HLA molecules have the ability to bind the auto antigen and present it to T cells, thereby inducing and/or maintaining the autoimmune process. Currently available immunosuppressive drugs are inadequate because of limited efficacy, lack of selectivity and considerable toxicity.

The present invention is directed to compounds which inhibit the binding of peptides to the major histocompatibility complex class II, a more selective target for therapeutic treatment and prevention of autoimmune diseases. Major histocompatibility complex class II molecules (MHC class II) are cell-surface glycoproteins that bind antigenic peptide fragments and display them at the cell surface to CD4-positive helper T-cells. The action of these molecules forms part pathway of the immune system for identifying and responding to foreign antigens. In brief, antigen presenting cells internalize foreign proteins. Once internalized, the proteins are proteolytically degraded and short sequences of the degraded proteins are bound to MHC class II molecules in an endosomal compartment. These complexes of the short sequences bound to the MHC Class II molecule are then exposed on the cell surface where they initiate a series of immunogenic events.

MHC Class II proteins are synthesized and assembled in the endoplasmic reticulum as trimers composed of highly polymorphic α and β-chain polypeptides and a non-polymorphic invariant chain polypeptide. The invariant chain prevents the premature binding of peptides to MHC class II. In addition, the invariant chain contains a sequence that targets the α/β heterodimer into the low pH, protease-rich endosomal compartment. In this compartment, the invariant chain is removed, leaving the MHC class II α/β heterodimers free to bind antigenic peptides.

Both class I and class II histocompatibility proteins have different domain organizations but similar structures, with two membrane-proximal immunoglobulin-like domains and a membrane-distal peptide-binding site formed by an eight stranded β-sheet and two α-helical regions. Polymorphic residues in both class I and II proteins are clustered in the peptide-binding region and are responsible for the different peptide specificities observed for different histocompatibility proteins. Class I histocompatibility proteins are specific for peptides of defined length, usually 8–10 residues and have allele-specific binding motifs characterized by strong preferences for a few side chains at some positions in the peptide, and wide tolerance for many side chains at the other positions. Class II histocompatibility proteins bind longer peptides with no apparent restriction on peptide length. Class II proteins also have allele specific motifs, which have been more difficult to characterize because of the difficulty in aligning peptide sequences of different lengths.

The mechanism of peptide binding to class II histocompatibility proteins has not been clearly defined. The 3.3 angstrom crystal structure of the human class II histocompatibility protein HLA-DR1 showed that bound peptide extended out the ends of the binding site, but interpretation of HLA-peptide interactions was complicated by the presence of a mixture of endogenous peptides in the peptide-binding site. Brown et al., Nature 364:33–39 (1993).

Stern et al. determined the refined 2.75 angstrom structure of the HLA-DR1/HA peptide complex showing that the peptide binds as a straight extended chain with a pronounced twist. Nature 368:215–221(1994). Hydrogen bonds between main-chain atoms along the peptide and HLA-DR1 residues from the α-helical regions and the β-sheet provide a component to the binding interaction that is independent of peptide sequence. Twelve of the hydrogen bonds involve residues conserved in most human and mouse class II alleles, and suggest a universal method for peptide binding by class II histocompatibility proteins. Five side chains of the HA peptide are accommodated by polymorphic pockets in the HLA-DR1 binding site. These pockets appear to determine the peptide specificity of different class II proteins.

Antigen presenting cells (APCs) expressing MHC class II molecules capture proteins from extracellular fluids. APCs can take up antigens through surface immunoglobulin receptors, through $F_c$ receptor-mediated internalization of antibody/antigen complexes, or through bulk-phase endocytosis. Internalized antigens are then transported to endosomal compartments where they are digested into peptide fragments. A subset of these peptides can associate with a specific binding groove at the interface of MHC class II α and β-chain heterodimers. Most of the polymorphisms in these proteins are located within this binding groove, so that each different MHC class II allele can bind a distinct, but overlapping, subset of antigenic peptides. MHC class II/peptide complexes are then transported to the cell surface where they are recognized by T-cell receptors (TCRs) on CD4-positive T-cells. This process is pivotal for the generation of both humoral and cellular immune responses.

Three genetic loci within the human MHC encode class II antigen-presenting molecules: HLA-DP, HLA-DQ, and HLA-DR. These loci are highly polymorphic. For instance, there are over 30 DRβ alleles in the human population. Since each individual expresses only a small number of different histocompatibility proteins, each histocompatibility protein must be able to bind a large number of different peptides in order to ensure an immune response against many possible pathogens. The extensive polymorphism of histocompatibility genes may be the result of selection of alleles that can present peptides from particular pathogens.

The inheritance of particular MHC class II alleles is linked to susceptibility to many autoimmune diseases. A prominent example of this is susceptibility to rheumatoid arthritis (RA) which is genetically associated with a small subset of related DR alleles (DR4Dw4,DR4Dw14, and DR1). See, Skinner et al., Annals of the Rheumatic Diseases 53:171–177 (1994). Over 90% of RA patients possess at least one of these 3 DR alleles compared to 27% in an age-matched control group.

Autoimmune conditions are thought to involve the T-cell recognition of self-components by MHC Class II proteins, a situation which is normally avoided. This presentation generates an undesirable immune response to self. Since the sole function of MHC class II molecules is to present peptide antigens, the present invention is concerned with compounds which interfere with the binding of peptides to MHC class II molecules and a method of treating and preventing autoimmune diseases employing such compounds which interfere with the binding of peptides to MHC class II molecules associated with disease. Specifically blocking the formation of the MHC Class II self-peptide complex is a manner of disrupting the aberrant process of the autoimmune disorder without globally depressing immune function. Hurtenbach et al., J. Exp. Med. 177:1499–1504 (1993) demonstrated that treatment with MHC class II complex-blocking peptide prevented autoimmune diabetes in non-obese diabetic mice. Further, Guery et al., J. Exp. Med. 177:1461–1468 (1993) administered MHC class II binding peptides to mice and showed suppression of induction of T cell antibody responses. The binding inhibitors of the present invention may prevent the presentation of self-peptides to autoreactive T-cells that drive the disease process. An advantage of the immunotherapy and immunotherapeutic agents of the present invention is that they are very selective agents, targeting only certain alleles of MHC Class II, which may minimize the risk of opportunistic infections during long term treatment. Although competition for MHC binding among peptides is known, no non-peptide (or pseudopeptide) inhibitor of MHC Class II binding has been known. Due to the inherent pharmacological limitations of peptides, particularly within a system that involves proteolytic degradation of proteins, the compounds of the present invention having less peptidic character may present a useful avenue for therapy.

SUMMARY OF THE INVENTION

The novel compounds of the present invention are those of structural formula I:

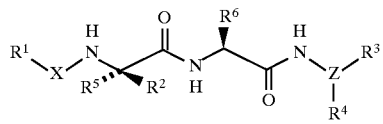

(I)

or a pharmaceutically acceptable salt or ester thereof, that inhibit peptide binding to MHC Class II proteins. As inhibitors of binding to MHC Class II proteins, the compounds of the present invention may be used in the treatment and prevention of autoimmune diseases, including rheumatoid arthritis, Type I diabetes, multiple sclerosis, lupus erythematosis, Graves disease and pemphigus.

There is no precedent in the literature for inhibition of MHC Class II proteins by nonpeptides or pseudopeptides.

Therefore it is an object of this invention to provide compounds that have activity in the inhibition of peptide binding to MHC Class II proteins. It is an additional object of this invention to provide methods of using the compounds of formula I for the treatment of autoimmune conditions such as rheumatoid arthritis, Type I diabetes, multiple sclerosis, lupus erythematosis, Graves disease and pemphigus.

It is a further object of this invention to provide pharmaceutical compositions for the compounds of formula I. Still another object of the present invention is to provide a method for in vitro inhibition of peptide binding of MHC Class II proteins.

DETAILED DESCRIPTION OF THE INVENTION

The novel compounds of this invention have the structural formula I:

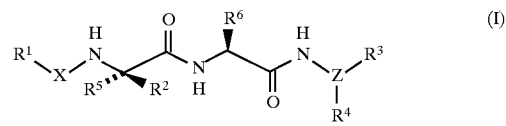

(I)

or a pharmaceutically acceptable salt or ester thereof, wherein:

X is selected from
  (a) $CHR^8$,
  (b) $C=O$,
  (c) $SO_2$, and
  (d) $-C(O)O-$;

Z is selected from:
  (a) CH, and
  (b) N;

$R^1$ is selected from
  (a) $C_{1-10}$ alkyl, unsubstituted or substituted with one to three substituents selected from:
    (1) aryl,
    (2) cycloalkyl,
    (3) halogen,
    (4) $NHR^7$, and
    (5) a heterocyclic ring,
  (b) $C_{2-10}$ alkenyl unsubstituted or substituted with one to three substituents selected from
    (1) aryl,
    (2) cycloalkyl,
    (3) halogen,
    (4) $NHR^7$, and
    (5) a heterocyclic ring,
  (c) cycloalkyl, and
  (d) a heterocyclic ring;

$R^2$ is selected from
  (a) hydrogen, and
  (b) $C_{1-3}$ alkyl unsubstituted or substituted with one to three halo substituents;

$R^3$ and $R^4$ are each independently selected from:
  (a) hydrogen,
  (b) $CONR^8R^8$,
  (c) $CO_2R^8$,
  (d) $C_{1-10}$ alkyl unsubstituted or substituted with one to three substituents selected from:
    (1) $CONHR^8$,
    (2) $CO_2R^8$
    (3) OH, and
    (4) $NH_2$,
  or $R^3$ and $R^4$ together with Z form a 6 to 8 membered lactam ring; for example

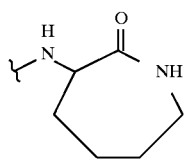

$R^5$ is selected from:
  (a) $C_{1-5}$ alkyl, unsubstituted or substituted with one to three substituents independently selected from:
    (a) cycloalkyl,
    (b) aryl,
    (c) OH,
    (d) $NH_2$,
    (e) —NHCH=NH($NH_2$),
    (f) —NHCO-aryl, and
    (g) halogen; and
  (b) $C_{2-5}$ alkenyl, unsubstituted or substituted with one to three substituents independently selected from:
    (a) cycloalkyl,
    (b) aryl,
    (c) OH,
    (d) $NH_2$,
    (e) —NHCH=NH($NH_2$),
    (f) —NHCO-aryl, and
    (g) halogen;

$R^6$ is $C_{1-5}$ alkyl, unsubstituted or substituted with one to three substituents selected from:
  (a) cycloalkyl,
  (b) aryl,
  (c) OH,
  (d) $NH_2$, and
  (e) halogen;

$R^7$ is selected from:
  (a) $C_{1-4}$ alkyl,
  (b) $C_{1-4}$ alkoxycarbonyl,
  (c) $C_{1-4}$ alkylcarbonyl, and
  (d) $C_{1-4}$ alkylsulphonyl;

each $R^8$ is independently selected from
  (a) hydrogen, and
  (b) $C_{1-4}$ alkyl;

cycloalkyl is independently selected at each occurrence from
  (a) $C_{3-8}$ saturated cycloalkyl unsubstituted or substituted with one to three substituents selected from:
    (1) hydroxy,
    (2) halogen,
    (3) $C_{1-4}$ alkyl, and
    (4) $C_{1-4}$ alkoxy,
  (b) $C_{3-8}$ saturated cycloalkyl substituted with aryl or $C_{3-8}$ cycloalkyl
  (c) $C_{3-8}$ saturated cycloalkyl fused with aryl or $C_{3-8}$ cycloalkyl, aryl is independently selected at each occurrence from:
  (a) phenyl,
  (b) naphthyl,
  (c) indenyl,
  (d) thiophenyl,
  (e) benzothiophenyl,
  (f) furanyl,
  (g) benzofuranyl,
  (h) pyrrolyl,
  (i) indolyl,
  (j) pyridyl,
  and is either unsubstituted or substituted with one to three substituents independently selected from:
    (1) $C_{1-4}$ alkyl,
    (2) $C_{1-4}$ alkoxy,
    (3) halogen, and
    (4) hydroxy, halogen is independently selected at each occurrence from:
  (a) F,
  (b) Cl,
  (c) Br, and
  (d) I;

a heterocyclic ring is independently selected at each occurrence from:
  (a) $C_{3-8}$ cycloalkyl wherein one or two of the carbon atoms are replaced with a heteroatom selected from oxygen, nitrogen, and sulfur, unsubstituted or substituted with one to three substituents selected from
    (1) $C_{1-4}$ alkyl,
    (2) $C_{1-4}$ alkoxy,
    (3) halogen, and
    (4) hydroxy,
  (b) $C_{3-8}$ cycloalkyl wherein one or two of the carbon atoms are replaced with a heteroatom selected from oxygen, nitrogen, and sulfur, substituted with aryl or $C_{3-8}$ cycloalkyl.
  (c) $C_{3-8}$ cycloalkyl wherein one or two of the carbon atoms are substituted with a heteroatom selected from oxygen, nitrogen and sulfur, fused with aryl or $C_{3-8}$ cycloalkyl.

Combinations of substituents and/or variables are permissible only if such combinations result in stable compounds.

As used herein "alkyl" is intended to include both branched- and straight-chain saturated aliphatic hydrocarbon groups having the specified number of carbon atoms, e.g, methyl, ethyl, propyl, butyl, pentyl, hexyl, heptyl, octyl, nonyl, decyl and isomers thereof such as isopropyl, isobutyl, sec-butyl, tert-butyl, isopentyl, isohexyl, etc. "Alkoxy" represents an alkyl group having the indicated number of carbon atoms attached through an oxygen bridge, e.g. methoxy, ethoxy, propyloxy, isopropoxy, etc. "Alkoxycarbonyl" represents alkyl-O—C(O)— wherein the indicated number of carbons refers to those of the alkyl residue. "Acyl" represents an alkyl group having the indicated number of carbon atoms attached through a —C(O)— bridge. "Sulfonyl" represents an alkyl group having the indicated number of carbon atoms attached through a —$SO_2$— bridge.

The terms halogen and halo refer to F, Cl, Br and I.

The heterocyclic or aryl ring may be attached to the structural formula I at any nitrogen atom (in the case of heterocyclic) or carbon atom (in either case) in the ring which results in the creation of a stable, uncharged structure.

In one embodiment of the instant invention are compounds of formula I wherein:

X is $CHR^8$;

Z is selected from:
  (a) CH, and
  (b) N;

$R^1$ is selected from:
  (a) $C_{1-10}$ alkyl, unsubstituted or substituted with one to three substituents independently selected from:
    (1) aryl, and
    (2) cycloalkyl,
  (b) cycloalkyl;

$R^2$ is H;

$R^3$ and $R^4$ are each independently selected from:
  (a) —$CONR^8R^8$,
  (b) —$COOR^8$, and (c) $C_{1-10}$ alkyl;

$R^5$ is $C_{1-4}$ alkyl, unsubstituted or substituted with one to three substituents selected from:
(a) aryl,
(b) $NH_2$, and
(c) $NHCH=NH(NH_2)$;

$R^6$ is $C_{1-4}$ alkyl;

$R^8$ is selected from
(a) H
(b) $C_{1-4}$ alkyl.

A class of compounds within this embodiment further limited to those wherein:

X is $CH_2$;
Z is N;
$R^1$ is selected from:
(a) $C_{1-10}$ alkyl, unsubstituted or substituted with cycloalkyl, and
(b) cycloalkyl;

$R^2$ is H;

$R^3$ and $R^4$ are each independently selected from:
(a) $-CONR_8R^8$,
(b) $-COOR^8$, and
(c) $C_{1-10}$ alkyl;

$R^5$ is $C_{1-4}$ alkyl, unsubstituted or substituted with one to three substituents selected from:
(a) $NH_2$, and
(b) $NHCH=NH(NH_2)$;

$R^6$ is $C_{1-4}$ alkyl;

$R^8$ is selected from:
(a) H, and
(b) $C_{1-4}$ alky cycloalkyl is selected from:
(a) $C_{3-8}$ saturated cycloalkyl,
(b) $C_{3-8}$ saturated cycloalkyl substituted with aryl or C1–8 cycloalkyl, and
(c) $C_{3-8}$ saturated cycloalkyl fused with aryl or C1–8 cycloalkyl;

aryl is selected from:
(a) phenyl,
(b) naphthyl, and
(c) pyridyl.

Examples of compounds illustrating the present invention include, but are not limited to, the following:

(1) N-α-((3-Cyclohexyl)propyl))-pyAla-Nva-Leu-NH$_2$,
(2) N-α-((2-Methyl-2-((3-cyclohexyl)propylamino))-propanoyl)-Nva-Leu-NH$_2$,
(3) N-α-((2-Methyl-2-((3-cyclohexyl)propylamino))-4-pentenoyl)-Nva-Leu-NH$_2$,
(4) N-α-((2-Methyl-2-((3-cyclohexyl)propylamino))-4-pentanoyl)-Nva-Leu-NH$_2$,
(5) N-α-((3-Cyclohexyl)propyl))-pyAla-Nva-cLys,
(6) N-α-((3-Cyclohexyl)propyl))-Nva-Nva-Leu-NH$_2$,
(7) N-α-Ethylcarbamoyl-Cha-Val-Nva-NH-NH$_2$,
(8) (α-CBZ)-(ε-BOC)Lys-Nva-Leu-NH$_2$,
(9) (α-CBZ)-Lys-Nva-Leu-NH$_2$,
(10) α-[Cinnamoyl]-(ε-BOC)Lys-Nva-Leu-NH$_2$,
(11) α-[Cinnamoyl]-Lys-Nva-Leu-NH$_2$,
(12) α-[2-methylcinnamoyl]-(ε-BOC)Lys-Nva-Leu-NH$_2$,
(13) α-[2-methylcinnamoyl]-Lys-Nva-Leu-NH$_2$,
(14) α-[3-methylcinnamoyl]-(ε-BOC)Lys-Nva-Leu-NH$_2$,
(15) α-[3-methylcinnamoyl]-Lys-Nva-Leu-NH$_2$,
(16) α-[2-Phenylcyclopropyl-1-carbonyl]-(ε-BOC)Lys-Nva-Leu-NH$_2$,
(17) α-[2-Phenylcyclopropyl-1-carbonyl]-Lys-Nva-Leu-NH$_2$,
(18) α-[2-Benzylcyclopropyl-1-carbonyl]-(ε-BOC)Lys-Nva-Leu-NH$_2$,
(19) α-[2-Benzylcyclopropyl-1-carbonyl]-Lys-Nva-Leu-NH$_2$,
(20) α-[1-phenylcyclopropyl-1-carbonyl]-(ε-BOC)Lys-Nva-Leu-NH$_2$,
(21) α-[1-Phenylcyclopropyl-1-carbonyl]-Lys-Nva-Leu-NH$_2$,
(22) α-[(1R,2S)-Cyclohexylcyclopropyl-1-carbonyl]-Lys-Nva-Leu-NH$_2$,
(23) α-[Benzylurea]-(ε-CBZ)Lys-Nva-Leu-NH$_2$,
(24) α-[Benzylurea]-Lys-Nva-Leu-NH$_2$,
(25) α-[2-methyl-3-phenylpropionyl]-(ε-CBZ)Lys Nva-Leu-NH$_2$,
(26) α-[2-methyl-3-phenylpropionyl]-Lys-Nva-Leu-NH$_2$,
(27) α-[2-(t-Butylsulfony)methyl-3-phenylpropionyl]-(ε-BOC)Lys-Nva-Leu-NH$_2$,
(28) α-[2-(t-Butylsulfony)methyl-3-phenylpropionyl]-Lys-Nva-Leu-NH$_2$,
(29) α-[2,2-dimethyl-3-phenylpropionyl]-(ε-BOC)Lys-Nva-Leu-NH$_2$,
(30) α-[2,2-dimethyl-3-phenylpropionyl]-Lys-Nva-Leu-NH$_2$,
(31) α-[3S-methyl-3-phenylpropionyl]-(ε-CBZ)Lys-Nva-Leu-NH$_2$,
(32) α-[3S-methyl-3-phenylpropionyl]-Lys-Nva-Leu-NH$_2$,
(33) α-[3R-methyl-3-phenylpropionyl]-(ε-BOC)Lys-Nva-Leu-NH$_2$,
(34) α-[3R-methyl-3-phenylpropionyl]-Lys-Nva-Leu-NH$_2$,
(35) α-[3R-methyl-3-cyclohexylpropionyl]-(ε-BOC)Lys-Nva-Leu-NH$_2$,
(36) α-[3R-methyl-3-cyclohexylpropionyl]-Lys-Nva-Leu-NH$_2$,
(37) α-[(1R,2S)-2-Cyclohexylcyclopropyl-1-carbonyl]-Lys-Nva-Leu-NH$_2$,
(38) α-(3-Phenylpropyl)-(ε-BOC)Lys-Nva-Leu-NH$_2$,
(39) α-[3-Phenylpropyl]-Lys-Nva-Leu-NH$_2$,
(40) α-[3-Cyclohexylpropyl]-(ε-BOC)Lys-Nva-Leu-NH$_2$,
(41) α-[3-Cyclohexylpropyl]-Lys-Nva-Leu-NH$_2$,
(42) α-[trans-2-Cyclohexylcyclopropyl-1-methyl]-Lys-Nva-Leu-NH$_2$,
(43) EtOCO-Cha-(ε-BOC)Lys-Nva-α-AzaLeu-NH$_2$,
(44) EtOCO-Cha-Lys-Nva-α-AzaLeu-NH$_2$,
(45) (α-BOC)-(ε-CBZ)Lys-Nle-α-AzaNle-OEt,
(46) α-[3-Cyclohexylpropyl]-(ε-CBZ)Lys-Nle-α-AzaNle-OEt,
(47) α-[3-Cyclohexylpropyl]-Lys-Nle-α-AzaNle-OEt,
(48) α-[3-Cyclohexylpropyl]-(ε-BOC)Lys-Nva-α-AzaLeu-OEt,
(49) α-[3-Cyclohexylpropyl]-Lys-Nva-α-AzaLeu-OEt,
(50) α-[3-Cyclohexylpropyl]-(ε-CBZ)Lys-Nva-α-AzaNle-OEt,
(51) α-[3-Cyclohexylpropyl]-Lys-Nva-α-AzaNle-OEt,
(52) α-[1,2,3,4-tetrahydronaphthyl-2-methyl]-(ε-CBZ)Lys-Nva-α-AzaNle-OEt,

(53) α-[1,2,3,4-tetrahydronaphthyl-2-methyl]-Lys-Nva-α-AzaNle-OEt,
(54) N-ethylcarbamoyl-phenylalanine-valine-alanine-leucinol,
(55) N-ethylcarbamoyl-phenylalanine-valine-norvalanine-leucinol,
(56) N-3-cyclohexylpropyl-valine-alanine-leucinol,
(57) N-E -α-methylcinnamyl-valine-alanine-leucinol,
(58) N-ethylcarbamoyl-phenylalanine-valine-alanin-(3',3'-dimethylbutyl)amide,
(59) N-ethylcarbamoyl-phenylalanine-valine-alanin-(isoamyl)amide,
(60) N-ethylcarbamoyl-phenylalanine-omithine-norvaline-leucin-hydrazide,
(61) N-ethylcarbamoyl-phenylalanine-valine-alanine-leucin-hydrazide,
(62) N-ethylcarbamoyl-phenylalanine-valine-leucinhydrazide,
(63) N-ethylcarbamoyl-phenylalanine-valine-alaninhydrazide,
(64) N-Boc-valine-norvaline-leucinamide,
(65) N-3-cyclohexylpropyl-valine-norvaline-leucinamide,
(66) N-E -α-methylcinnamyl-valine-alanine-leucinamide,
(67) N-3-phenylpropanoyl-lysine-norvaline-leucinamide, and
(68) N-3-cyclohexylpropanoyl-lysine-norvaline-leucinamide.

In one class of this embodiment are compounds further limited to those wherein:
(1) N-α-((3-Cyclohexyl)propyl))-pyAla-Nva-Leu-NH$_2$,
(2) N-α-((2-Methyl-2-((3-cyclohexyl)propylamino))-propanoyl)-Nva-Leu-NH$_2$,
(3) N-α-((2-Methyl-2-((3-cyclohexyl)propylamino))-4-pentenoyl)-Nva-Leu-NH$_2$,
(4) N-α-((2-Methyl-2-((3-cyclohexyl)propylamino))-4-pentanoyl)-Nva-Leu-NH$_2$,
(5) N-α-((3-Cyclohexyl)propyl))-pyAla-Nva-cLys,
(6) N-α-((3-Cyclohexyl)propyl))-Nva-Nva-Leu-NH$_2$,
(7) (α-CBZ)-Lys-Nva-Leu-NH$_2$,
(8) α-[Cinnamoyl]-Lys-Nva-Leu-NH$_2$,
(9) α-[2-methylcinnamoyl]-Lys-Nva-Leu-NH$_2$,
(10) α-[3-methylcinnamoyl]-Lys-Nva-Leu-NH$_2$,
(11) α-[2-Phenylcyclopropyl-1-carbonyl]-Lys-Nva-Leu-NH$_2$,
(12) α-[2-Benzylcyclopropyl-1-carbonyl]-Lys-Nva-Leu-NH$_2$,
(13) α-[1-Phenylcyclopropyl-1-carbonyl]-Lys-Nva-Leu-NH$_2$,
(14) α-[(1R,2S)-2-Cyclohexylcyclopropyl-1-carbonyl]-Lys-Nva-Leu-NH$_2$,
(15) α-[Benzylurea]-Lys-Nva-Leu-NH$_2$,
(16) α-[2-methyl-3-phenylpropionyl]-Lys-Nva-Leu-NH$_2$,
(17) α-[2-(t-Butylsulfony)methyl-3-phenylpropionyl]-Lys-Nva-Leu-NH$_2$,
(18) α-[2,2-dimethyl-3-phenylpropionyl]-Lys-Nva-Leu-NH$_2$,
(19) α-[3S-methyl-3-phenylpropionyl]-Lys-Nva-Leu-NH$_2$,
(20) α-[3R-methyl-3-phenylpropionyl]-Lys-Nva-Leu-NH$_2$,
(21) α-[3R-methyl-3-cyclohexylpropionyl]-Lys-Nva-Leu-NH$_2$,
(22) α-[3-Phenylpropyl]-Lys-Nva-Leu-NH$_2$,
(23) α-[3-Cyclohexylpropyl]-Lys-Nva-Leu-NH$_2$,
(24) α-[trans-2-Cyclohexylcyclopropyl-1-methyl]-Lys-Nva-Leu-NH$_2$,
(25) EtOCO-Cha-Lys-Nva-α-AzaLeu-NH$_2$,
(26) α-[3-Cyclohexylpropyl]-Lys-Nle-α-AzaNle-OEt,
(27) α-[3-Cyclohexylpropyl]-Lys-Nva-α-AzaLeu-OEt,
(28) α-[3-Cyclohexylpropyl]-Lys-Nva-α-AzaNle-OEt,
(29) α-[1,2,3,4-tetrahydronaphthyl-2-methyl]-Lys-Nva-α-AzaNle-OEt,
(30) N-ethylcarbamoyl-phenylalanine-valine-norvalanine-leucinol,
(31) N-ethylcarbamoyl-phenylalanine-ornithine-norvaline-leucin-hydrazide,
(32) N-ethylcarbamoyl-phenylalanine-valine-alanine-leucin-hydrazide, and
(33) N-3-cyclohexylpropanoyl-lysine-norvaline-leucinamide.

In a subclass of this class are the following compounds:
(1) N-α-((3-Cyclohexyl)propyl))-pyAla-Nva-cLys,
(2) α-[3-Cyclohexylpropyl]-Lys-Nle-α-AzaNle-OEt,
(3) α-[3-Cyclohexylpropyl]-Lys-Nva-α-AzaLeu-OEt,
(4) α-[3-Cyclohexylpropyl]-Lys-Nva-α-AzaNle-OEt,
(5) α-[1,2,3,4-tetrahydronaphthyl-2-methyl]-Lys-Nva-α-AzaNle-OEt,
(6) N-ethylcarbamoyl-phenylalanine-valine-norvalanine-leucinol,
(7) N-ethylcarbamoyl-phenylalanine-omithine-norvaline-leucin-hydrazide, and
(8) N-ethylcarbamoyl-phenylalanine-valine-alanine-leucin-hydrazide.

The compounds of the present invention are named by reference to a tetrapeptide of the general format:

cap-P1-P2-P3-P4 where "PX" represents the amino acid in the "xth" position in the tetrapeptide starting from P1 at the N-terminus. The 'cap' is a non-amino acid group attached to the N-terminus. P4 is the carboxy terminal residue. Names are given as the amino terminus 'cap' followed by a hyphen and the three letter code of the first residue, followed by a hyphen and the three letter code of the second residue, followed by a hyphen and the three letter code of the third residue, followed by a hyphen and the three letter code of the fourth residue (three letter code is standard peptide nomenclature: see Amino Acid and Peptide Nomenclature *J. Biol. Chem* 260, 14–42 and IUPAC-IUB Nomenclature recommendations). Where any portion of the putative tetrapeptide is replaced by a non-peptide the residue (or residues) is replaced by a one line alphanumeric description constructed from IUPAC nomenclature and/or accepted abbreviations. For example, where 'cap-P1' is replaced by a 3-cyclohexylpropyl residue the name is of the format cHx(CH$_2$)$_3$-P2-P3-P4. After the last amino acid residue, or replacement, a hyphen is followed by the moiety positioned at the carboxy terminus of the analogous tetrapeptide, i.e. —NH2,—OH, —OEt. Unnatural amino acids are referred to by accepted nomenclature.

Examples of generally accepted abbreviations employed are:

| Name | Abbreviation(s) |
| --- | --- |
| Alkyl groups | Et, Pr, Bu, iBu ..etc |
| Benzoyl | Bz |
| Benzyl | Bzl |
| Benzyloxycarbonyl | Cbz or Z |
| t-Butoxycarbonyl | Boc |
| Ethoxycarbonyl | EtOCO |
| Cyclohexyl | cHx |
| Cyclopentyl | cPe |
| Cyclohexlalanine | Cha |
| Norleucine | Nle |
| Xaa | Any amino acid |

Semicarbazide analogs of amino acids wherein the α-CH is replaced by a N-atom are written α-AzaXaa. Similar analogs not corresponding a commonly named amino acids are denoted by an alphanumeric string. Examples are:

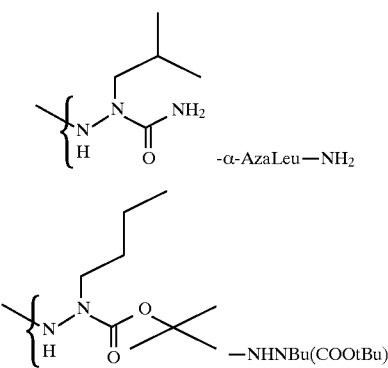

The compounds of the present invention are of substantially non-peptide character, yet inhibit peptide binding MHC Class II proteins. Because the compounds of the present invention have substantially reduced peptide character relative to known inhibitors, the compounds of the present invention will be more likely to penetrate cellular membranes to access the Class II loading compartment within the cell, where competition for peptide binding is thought to occur. They are also likely to be more stable than peptides in the proteolytic environment of the endosomal compartment and hence better able to compete with the endogenous peptides. Based on knowledge within the art regarding peptide versus nonpeptide pharmacology, the compounds of the present invention are expected to have better oral bioavailability and longer in vivo half life than intact peptides.

Also included within the scope of this invention are pharmaceutically acceptable salts of the compounds of formula I, where a basic or acidic group is present on the structure.

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, omithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, e.g. by reacting a free acid with a suitable organic or inorganic base. Where a basic group is present, such as amino, an acidic salt, i.e. hydrochloride, hydrobromide, acetate, pamoate, and the like, can be used as the dosage form.

Also, in the case of an acid (—COOH) or alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

When any variable (e.g., $R^1$, $R^6$, etc.) occurs more than one time in any constituent or in formula I, its definition on each occurrence is independent of its definition at every other occurrence. Also, combinations of substituents and/or variables are permissible only if such combinations result in stable compounds.

The compounds of the present invention may have chiral centers other than those centers whose stereochemistry is depicted in formula I, and therefore may occur as diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The term "therapeutically effective amount" means that amount of a drug or pharmaceutical agent that will elicit the biological or medical response of a tissue, system, animal or human that is being sought by a researcher, veterinarian, medical doctor or other clinician, which includes alleviation of the symptoms of the disorder being treated. The novel methods of treatment of this invention are for disorders known to those skilled in the art. The term "mammal" includes humans.

The present invention has the objective of providing methods of treating and preventing autoimmune diseases including: rheumatoid arthritis, Type I diabetes, multiple sclerosis, lupus erythematosis, Graves disease and pemphigus by oral, systemic, parenteral or topical administration of the novel compounds of formula I either alone or in combination with other agents useful in treating autoimmune diseases. For the treatment of rheumatoid arthritis such agents which may be used in combination with the novel compounds of structural formula (I) include, but are not limited to: aspirin; NSAIDs including fenoprofen, tolmetin, sulindac, meclofenamate, indomethacin, ibuprofen, naproxen, ketoprofen, piroxicam, flurbiprofen, and diclofenac; gold sodium thiomalate; aurothioglucose; auranofin; penicillamine; hydroxychloroquine; sulfasalazine, corticosteroids; methotrexate; azathioprine; and cyclophosphamide. For the treatment of type 1 diabetes such agents which may be used in combination with the novel compounds of structural formula (I) include, but are not limited to: insulin therapy. For the treatment of multiple sclerosis such agents which may be used in combination with the novel compounds of structural formula (I) include, but are not limited to: prednisone, dexamethazone, azathioprine, copolymer 1, cyclophosphamide, interferon, plasmapheresis, and baclofen. For the treatment of lupus erythematosis, such agents which may be used in combination with the novel compounds of structural formula (I) include, but are not limited to: antimalarials such as hydroxychloroquinine, chloroquine, and quinacrine; prednisone and methyl prenisolone; and cyclophosphamide. For the treatment of pemphigus, such agents which may be used in combination with the novel compounds of structural formula (I) include, but are not limited to: systemic corticosteroids, prednisone, methotrexate, cyclophosphamide and azathioprine.

The present invention also has the objective of providing suitable systemic including oral and parenteral including topical pharmaceutical formulations for use in the novel methods of treatment and prevention of the present invention. The term "treatment" is intended to include ameliorating the autoimmune symptoms and/or arresting the progression of an autoimmune disease in an individual known to be, or believed to be suffering from an autoimmune disease. The term "prevention" is intended to include ameliorating the underlying cause of an autoimmune condition in an individual who may not have begun to experience recognizable symptoms of an autoimmune condition, and arresting the progress of an autoimmune disease in a patient who has not begun to experience recognizable symptoms of an autoimmune condition. The term "administration of" and or "administering a" compound should be understood to mean providing a compound of the invention or a prodrug of a compound of the invention to the individual in need of treatment. The compositions containing the present compounds as the active ingredient for use in the treatment of the above-noted conditions can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

The daily dosage of the products may be varied over a range from 0.01 to 1,000 mg per adult human/per day. For oral administration, the compositions are preferably provided in the form of tablets containing 0.01 to 1,000 mg, and particularly dosages of 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 7 mg/kg of body weight per day.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The compounds of the present invention may also be used in the preparation of a medicament or an agent useful in the treatment of autoimmune diseases, including rheumatoid arthritis, Type I diabetes, multiple sclerosis, lupus erythematosis, Graves disease and pemphigus.

For the treatment and prevention of autoimmune diseases, the compounds of the present invention may be administered in a pharmaceutical composition comprising the active compound in combination with a pharmaceutically acceptable carrier adapted for topical administration. Topical pharmaceutical compositions may be, e.g., in the form of a solution, cream, ointment, gel, lotion, shampoo or aerosol formulation adapted for application to the skin. These topical pharmaceutical compositions containing the compounds of the present invention ordinarily include about 0.005% to 5% by weight of the active compound in admixture with a pharmaceutically acceptable vehicle.

For the treatment and prevention of autoimmune diseases, the compounds of the present invention may be used together with agents known to be useful in treating autoimmune disease, discussed previously.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The compounds of the present invention can be prepared readily according to the following Schemes and Examples or modifications thereof using readily available starting materials, reagents and conventional synthesis procedures. In these reactions, it is also possible to make use of variants which are themselves known to those of ordinary skill in this art, but are not mentioned in greater detail.

The following examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds.

GENERAL METHODS.

All temperatures given in the following examples are in degrees Celsius. $^1$H nuclear magnetic resonance (NMR) spectra were taken at 300, 400 or 500 MHz at ambient temperature in the solvent indicated. Shifts are reported in ppm, referenced to solvent D. Except where indicated, commercially available compounds were used without further purification. Where not noted, natural and unnatural amino acids are of the (L) configuration. Various protected di- and tripeptides were prepared by conventional 1-(3-dimethylaminopropyl)-3-ethyl carbodimide hydrochloride (EDC)/hydroxybenztriazole (HOBT) solution phase couplings of appropriately protected amino acids. Anhydrous solvents were purchased from Aldrich. Methylene chloride was, in some cases, distilled from $CaH_2$ before use. All reactions run under anhydrous conditions were run under positive pressure of dry nitrogen.

Abbreviations used for amino acids follow the rules of the IUPAC-IUB Commission of Biochemical Nomenclature in *J. Biol.Chem.*, 1972, 247, 977–983. Additional abbreviations used are: Boc- is t-butoxycarbonyl, BOP is benzotriazole-1-yl-oxy-tris-(dimethylamino)-phosphonium hexafluorophosphate, DCC is N,N'-dicyclohexylcarbodiimide, DCM is dichloromethane, DIEA is N, N'-diisopropylethyl amine; DMF is N,N'-dimethyl formamide, EDC is 1-(3-dimethylaminopropyl)-3-ethyl carbodimide hydrochloride,EtOAc is ethyl acetate, ESI is electrospray ionization, ESI-MS is electrospray ionization mass spectroscopy, Fmoc is 9-fluorenylmethyloxycarbonyl, HOBT is N-hydroxybenzotriazole, HPLC is high pressure liquid chromatography, MeOH is methanol, NMP is N-methylpyrolidine, PyBOP, benzotriazole-1-yl-oxy-tris-pyrrolidino-phosphonium hexafluorophosphate; RINK-MBHA and Wang resins are common, commercially available, amide-linked polystyrene-based resins, RP-HPLC is reverse phase high performance liquid chromatography, RT is room temperature, SPPS is solid phase peptide synthesis, TFA is trifluoroacetic acid.

EXAMPLES 1 TO 3

Examples 1 through 3 were prepared by solid-phase synthesis using well documented procedures. Standard Fmoc chemistry on RINK-MBHA resin was used to link the first three C-terminal amino acids. Couplings were performed with DCC/HOBT in NMP for 70 min. Fmoc cleavage was achieved with 20% piperidine in NMP for 20 min. Following cleavage of the N-terminal Fmoc group of the tripeptide, the resins were treated with ~8 equivalents of cyclohexylpropionaldehyde, ~9 equivalents sodium cyanoborohydride in NMP for 120 min. Cleavage from the resin was achieved using 100% TFA. The crude materials were purified by reversed phase (C18) HPLC, using a mixed water/acetonitrile eluant containing 0.1% trifluoroacetic acid, and lyophilized. Materials were validated by mass spectral characterization.

EXAMPLE 1

N-α-((3-Cyclohexyl)propyl))-pyAla-Nva-Leu-NH$_2$

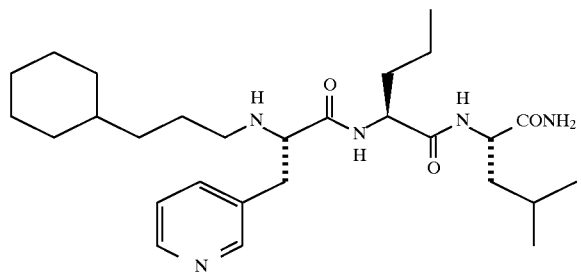

Mass spectrum [ESI]: m/z=502, 272

EXAMPLE 2

N-α((2-Methyl-2-((3-cyclohexyl)propylamino))-propanoyl)-Nva-Leu-NH₂

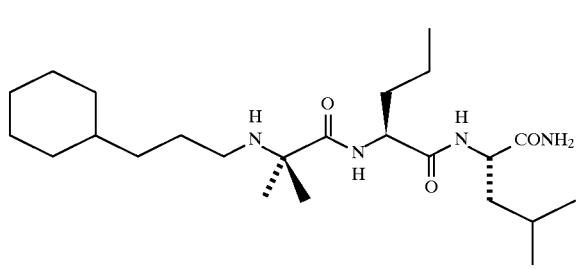

Mass spectrum [ESI]: m/z=439

EXAMPLE 3

N-α-((2-Methyl-2-((3-cyclohexyl)propylamino))-4-pentenoyl)-Nva-Leu-NH₂

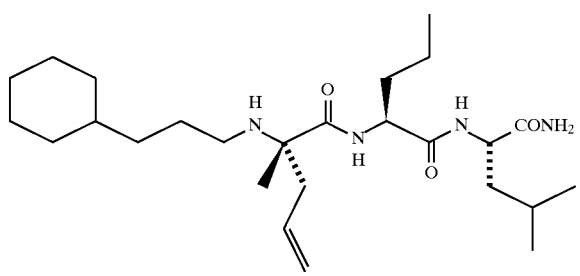

Mass spectrum [ESI]: m/z=464

EXAMPLE 4

N-α-((2-Methyl-2-((3 -cyclohexyl)propylamino))-4-pentanoyl)-Nva-Leu-NH₂

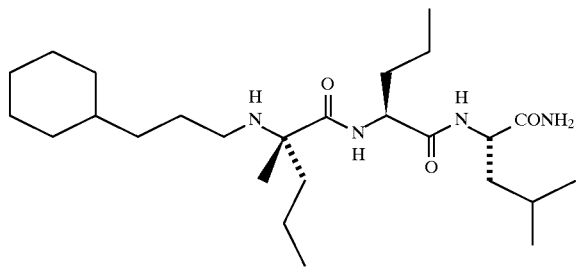

The product of Example 3 (3 mg) was dissolved in ethyl acetate (2 mL) and 10% Pd/C (cat.) added. The system was purged with hydrogen and hydrogenation continued at 1 atm H₂ and ambient temperature for 120 min. The reaction mixture was filtered through a pad of Celite™ diatomaceous earth and concentrated. The product was lyophilized from acetonitrile/water and validated by mass spectral characterization. Mass spectrum [ESI]: m/z=467

EXAMPLE 5

N-α-((3-Cyclohexyl)propyl))-pyAla-Nva-cLys

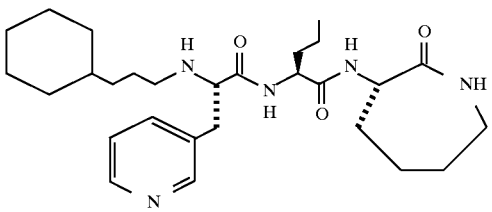

Cyclolysine hydrochloride (0.6 mmol) and Boc-norvaline (0.6 mmol) were dissolved in DMF (10 mL). HOBT (0.6 mmol) and EDC (0.6 mmol) were added and the mixture adjusted to neutral pH with diisopropylethylamine. After 120 min, aq. NaHCO₃ was added and the mixture extracted with EtOAc. The organics were washed with 2N HCl, dried over magnesium sulfate, filtered and concentrated. The residue was dissolved in 4N HCl/dioxane (5 mL) and stirred for 30 min. Concentration of the mixture gave the required Nva-cLys-NH₂.HCl. A fraction of the Nva-cLys-NH₂.HCl (80 mg, 0.33 mmol) was dissolved in DMF (10 mL) and Boc-3-pyridylalanine (0.33 mmol) added. HOBT (0.33 mmol) and EDC (0.33 mmol) were added. After 120 min aq. NaHCO₃ was added and the mixture extracted with EtOAc. The organics were washed with 2N HCl dried over magnesium sulfate, filtered and concentrated. The residue was dissolved in 4N HCl/dioxane (5 mL) and stirred for 30 min. Concentration of the mixture gave the required PyAla-Nva-cLys-NH₂.2HCl. PyAla-Nva-cLys-NH₂.2HCl (52 mg) was dissolved in MeOH (5 mL) and treated with cyclohexylpropionaldehyde (1 eq), sodium cyanoborohydride (1.1 eq) and diisopropylethylamine (1 eq). After 60 min water was added and the mixture extracted with EtOAc, dried over magnesium sulfate, filtered and concentrated. This material was lyophilized from acetonitrile/water. Half of the lyophilizate was purified by reversed phase (C18) HPLC using a mixed water/acetonitrile eluant containing 0.1% trifluoroacetic acid, and lyophilized to provide the title compound. Selected NMR signals, CD₃OD, 500 MHz, d/ppm : 8.1 (1H,d), 8.0 (1H,d) 4.5 (1H,dd), 4.38 (1H,dd), 4.16 (1H,dd), 3.24 (2H, m), 2.92 (2H,m), 0.94 (3H,t). Mass spectrum [ESI]: m/z= 500.

EXAMPLE 6

N-α-((3-Cyclohexyl)propyl))-Nva-Nva-Leu-NH₂

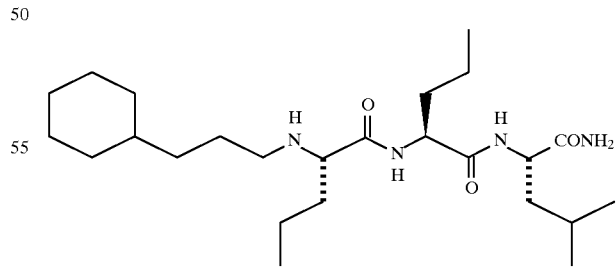

Standard Fmoc chemistry on RINK-MBHA resin was used to link the first three C-terminal amino acids. Couplings were performed with DCC/HOBT in NMP for 70 min. Fmoc cleavage was achieved with 20% piperidine in NMP for 20 min. Following cleavage of the N-terminal Fmoc group, the tripeptide was cleaved from the resin by treatment with 100% TFA. The tripeptide (5.1 mg) was dissolved in MeOH (100 μL). Cyclohexylpropionaldehyde (1.6 mg) was added followed by sodium cyanoborohydride (2.0 mg). After 1h NaHCO₃ solution was added and the mixture extracted with EtOAc, dried over magnesium sulfate, filtered and concentrated. The crude material was purified by chromatography on silica gel. Selected NMR signals, CD₃OD, 400 MHz, d/ppm : 4.40(2H,m), 3.15 (1H,t), 2.47 (2H,m), 0.95 (6H,m), 0.90 (6H,d). Mass spectrum [ESI]: m/z=453.

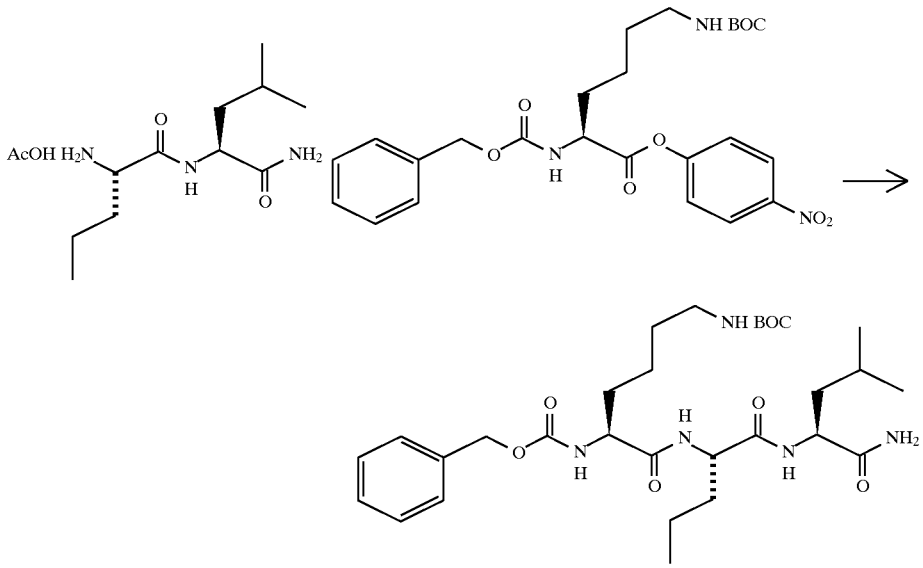

EXAMPLE 7

N-α-Ethylcarbamoyl-Cha-Val-Nva-NH-NH₂

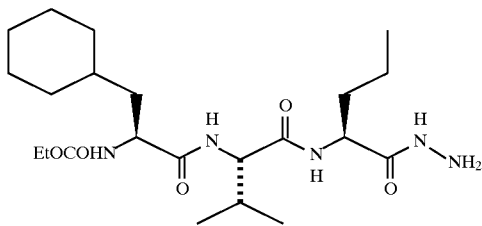

The title Hydrazide was prepared by solid-phase synthesis using well documented procedures. Standard Fmoc chemistry on Wang resin was used to link the three amino acids. Couplings were performed with DCC/HOBT in NMP for 70 min. Fmoc cleavage was achieved with 20% piperidine in NMP for 20 min. Following cleavage of the N-terminal Fmoc group of the tripeptide the resin was treated with ethyl chloroformate (1 eq) and diisopropylethylamine (1 eq) in DMF for 120 min. The material was cleaved from the resin and the C-terminal hydrazide generated by treatment with hydrazine (30 eq) in DMF for 2 days. The crude material was purified by reversed phase (C18) HPLC using a mixed water/acetonitrile eluant containing 0.1% trifluoroacetic acid, lyophilized and validated by mass spectral characterization.

Mass spectrum [ESI]: m/z=468.

EXAMPLE 8

(ε-BOC)Lys Nva Leu-NH₂

Step 1: Preparation of (α-CBZ)-(ε-BOC)Lys-Nva-Leu-NH₂

The acetate salt of Nva Leu-NH₂ (1.0 Eq, 80 mg, 0.277 mmol) and (α-CBZ)(ε-BOC)lysine p-nitrophenyl ester (1.0 Eq, 138.9 mg, 0.277 mmol) were dissolved in DMF (5 mL) at 0° C. Diisopropyl ethylamine (45 μL, 0.25 mmol) was added at 0° C. After 1 hour the mixture was allowed to warm to room temperature and stir overnight. The mixture was diluted with water and ethyl acetate. The organic layer was washed with water, saturated sodium bicarbonate(aq) until colorless, water and brine. The crude product was purified by elution from a Sephadex LH-20-100 (700×12.5 mm) column using methanol. The product was recovered as an amorphous solid. 1H NMR [400 MHz, d4 Methanol] Selected peaks: 7.32 (m, 5H), 5.09 (s, 2H), 4.36 (m, 1H), 4.28 (q, 1H), 4.05 (m, 1H), 3.01 (t, 2H), 0.93 (m, 6H), 0.89 (d, 3H). Mass spectrum [ESI, 80% ACN/20% 0.01% aqTFA]: m/z=592.3.

Step 2: Preparation of (α-CBZ)-(ε-BOC)Lys-Nva-Leu-NH₂:

Typical CBZ Removal

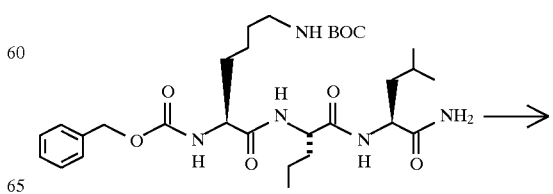

-continued

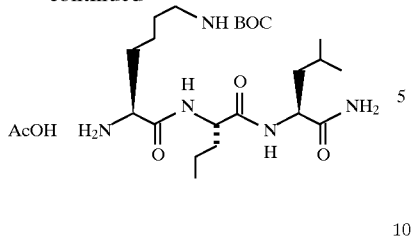

The (α-CBZ)-(ε-BOC)Lys-Nva-Leu-NH₂ (147 mg, 0.248 mmol, obtained according to the procedures above) was dissolved in glacial acetic acid (5 mL) with 10% Pd on activated carbon (30 mg, 20% by wt). The reaction flask was purged three times vacuum versus H₂ and stirred vigorously under one atm. of H₂ at room temperature. The reaction was typically complete after 1–2 hours as judged by TLC. The reaction mixture was filtered through a pad of Celite™ diatomaceous earth to remove the catalyst and concentrated i. vac. Residual acetic acid is removed as the toluene azeotrope i. vac. The residue was diluted with satd. aq. sodium bicarbonate and extracted eight times with EtOAc. The combined extracts were washed with brine, dried over Na₂SO₄ and reduced i. vac. The title compound was recovered as an oil. ¹H NMR [400 MHz, d4 Methanol] Selected peaks: 4.4 (dd brd, 1H), 4.31 (dd, 1H, J=8.6, 5.7 Hz), 3.33 (t,1H, J=6.0 Hz), 3.02 (t, 2H, J=6.8 Hz), 1.42 (s, 9H), 0.95 (d, 3H, J=6.4 Hz), 0.91 (d, 3H, J=6.4 Hz).

EXAMPLE 9

(α-CBZ)-Lys-Nva-Leu-NH₂

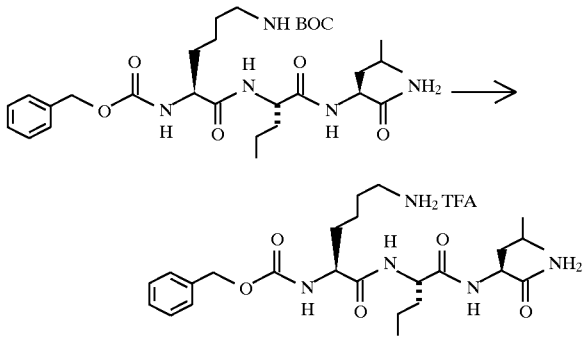

Typical BOC removal:

The (α-CBZ)-(ε-BOC)Lys-Nva-Leu-NH₂ (19.8 mg, 0.034 mmol, obtained according to Example 8, Step 1) was dissolved in methylene chloride (1.5 mL) and cooled to 0° C. Neat TFA (1.5 mL) was added dropwise. A solution was typically stirred ¼ to 1 h at 0° C. The reaction mixture was concentrated i. vac. and purified by preparatory reverse phase chromatography on an E. Merck LiChroprep RP-18 (310×25 mm) column with 0.1% TFA(aq) : CH₃CN (65:35) as eluent. The product was recovered as an amorphous solid. ¹H NMR [400 MHz, d4 Methanol] Selected peaks: 7.28 (m, 5H), 5.04 (s, 2H), 4.28 (m, 2H), 4.05 (m, 1H), 2.85 (t, 2H),0.87 (m, 9H). Mass spectrum [ESI, 80% ACN/20% 0.01% aqTFA]: m/z=492.4.

EXAMPLE 10

α-[Cinnamoyl]-(ε-BOC)Lys-Nva-Leu-NH₂

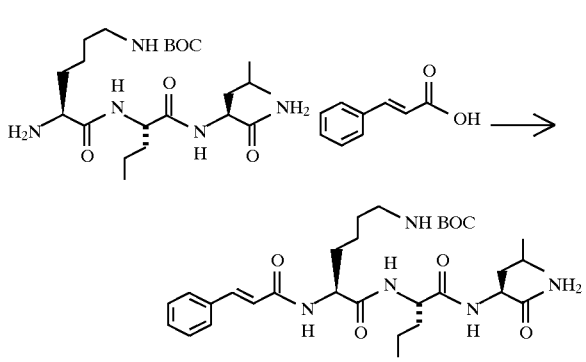

Typical EDC/HOBT Acylation:

The (ε-BOC)Lys-Nva-Leu-NH₂ (1.0 Eq, 50.8 mg, 0.11 mmol, the product of Example 8), trans-cinnamic acid (1.7 Eq, 27.4 mg, 0.19 mmol), and 1-hydroxy-benzotriazole monohydrate (1.0 Eq, 16.8 mg, 0.11 mmol) were combined and dissolved in DMF (2 ml). 1-(3-Dimethylaminopropyl)-3-ethylcarbodiimide hydrochloride (43 mg, 0.22 mmol) was added and reaction stirred under nitrogen at RT overnight. The reaction mixture was diluted with water and ethyl acetate and the aqueous layer was extracted three times with EtOAc. The combined organic layers were washed with water and brine. The combined extracts were dried over Na₂SO₄ and concentrated i. vac.

The crude product was purified by elution from a Sephadex LH-20-100 (780×12.7 mm) column with methanol. The product was recovered as an oil. ¹H NMR [400 MHz, d4 Methanol] Selected peaks: 7.51 (m, 3H), 7.33 (m, 3H), 6.67 (d, 1H), 4.33 (m, 2H), 4.23 (q, 1H), 2.99 (t, 2H), 0.87 (m, 9H). Mass spectrum [ESI, 80% CH₃CN/20% 0.01% aqTFA]: m/z=588.2.

EXAMPLE 11

α-[Cinnamoyl]-Lys-Nva-Leu-NH₂

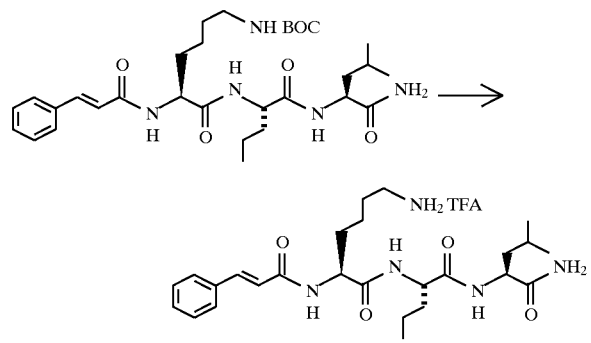

The BOC amine (21.7 mg, 0.036 mmol, the product of Example 10) was dissolved in CH₃OH (0.5 mL) at 0° C. Methanolic HCl 1.3N (1.5 mL) was added dropwise. The mixture was diluted with methanol (2 mL) after ¼ Hr and concentrated i. vac. The crude product was purified by preparatory reverse phase HPLC on an E. Merck LiChroprep RP-18 (310×25 mm) column with 0.1% TFA(aq): CH₃CN (65:35) as eluent. The product was recovered as an oil. ¹H NMR [300 MHz, d4 Methanol] Selected peaks: 7.51 (m, 3H), 7.34 (m, 3H), 6.66 (d, 1H), 4.3 (m, 3H), 2.89 (t, 2H), 0.88 (m,9H). Mass spectrum [ESI, 80% CH₃CN/20% 0.01% aqTFA]: m/z=488.2.

EXAMPLE 12

α-[2-methylcinnamoyl]-(ε-BOC)Lys-Nva-Leu-NH₂

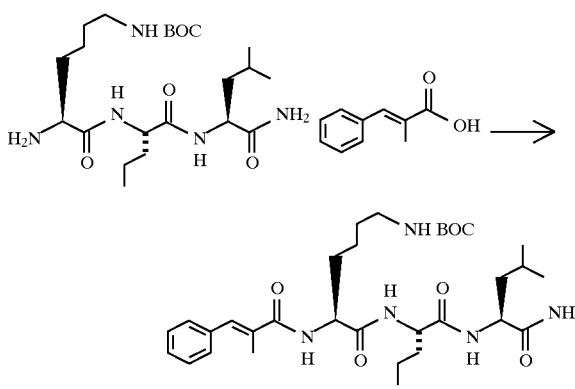

The acylation of (ε-BOC)Lys-Nva-Leu-NH₂ (18.7 mg, 0.041 mmol, obtained according to the procedures of Example 8) by α-methyl cinnamic acid (13.0 mg, 0.80 mmol) was carried out as described in Example 21289-174. The crude product was purified by elution from a Sephadex LH-20–100 (780×12.7 mm) column with methanol. The product was recovered as an oil. ¹H NMR [400 MHz, d4 Methanol] Selected peaks: 7.37 (m,5H), 7.31 (m,1H), 4.38 (m, 2H), 4.29 (q, 1H), 3.05 (t, 2H), 2.1 (s, 3H), 0.95 (m, 6H), 0.9 (d, 3H). Mass spectrum [ESI, 80% CH₃CN/20% 0.01% aqTFA]: m/z=602.2.

EXAMPLE 13

α-[2-methylcinnamoyl]-Lys-Nva-Leu-NH₂

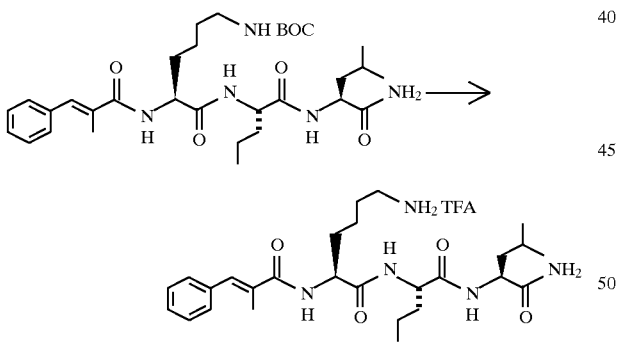

The BOC amine (20.7 mg, 0.034 mmol, product of Example 12) was dissolved in glacial acetic acid (2 ml) at room temperature. Trifluoroacetic acid (2 ml) was added dropwise. The reaction mixture was then cooled in an ice bath and stirred at 0° C. for 1 hr 15 minutes. The reaction mixture was diluted with methanol and concentrated i. vac. The crude product was purified by preparatory reverse phase HPLC on an E. Merck LiChroprep RP-18 column with 0.1% TFA(aq): CH₃CN (62:38). The product was recovered as an oil. ¹H NMR [300 MHz, d4 Methanol] Selected peaks: 7.32 (m,6H), 4.34 (m,3H), 2.9 (t, 2H), 2.05 (s, 3H),0.89 (m, 9H). Mass spectrum [ESI, 80% CH₃CN/20% 0.01% aqTFA]: m/z=503.2.

EXAMPLE 14

α-[3-methylcinnamoyl]-(ε-BOC)Lys-Nva-Leu-NH₂

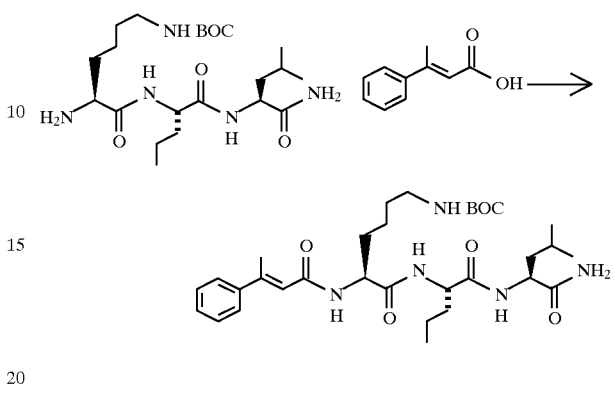

The acylation of (ε-BOC)Lys-Nva-Leu-NH₂ (49.7 mg, 0.109 mmol, the product of Example 8) by β-methyl cinnamic acid (21.8 mg, 0.134 mmol) was carried out as described in Example 10. The crude product was purified by elution from a Sephadex LH-20-100 (780×12.7 mm) column with methanol. The product was recovered as an oil. ¹H NMR [300 MHz, d4 Methanol] Selected peaks: 7.36 (m, 5H), 6.25 (s, 1H), 4.28 (m, 3H), 2.99 (t, 2H), 2.46 (s, 3H), 0.86 (m, 9H). Mass spectrum [ESI, 80% CH₃CN/20% 0.01% aqTFA]: m/z=602.

EXAMPLE 15

α-[3-methylcinnamoyl]-Lys-Nva-Leu-NH₂

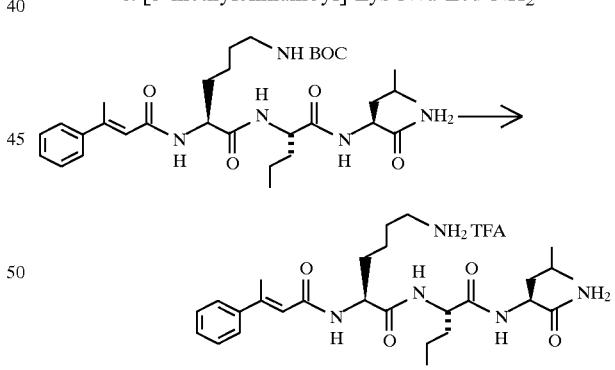

The deprotection of the BOC amine of Example 14 (36.6 mg, 0.061 mmol) was carried out as described in Example 9. The crude product was purified by preparatory reverse phase HPLC on an E. Merck LiChroprep RP-18 column with 0.1% TFA(aq): CH₃CN (38:62). The product was recovered as an oil. ¹H NMR [400 MHz, d4 Methanol] Selected peaks: 7.5 (m, 2H), 7.37 (m, 3H), 6.28 (s, 1H), 4.39 (m, 2H), 2.93 (t,2H), 2.51 (s3H), 0.94 (m, 9H). Mass spectrum [ESI, 80% CH₃CN/20% 0.01% aqTFA]: m/z= 502.3.

EXAMPLE 16

α-[2-Phenylcyclopropyl-1-carbonyl]-(ε-BOC)Lys-Nva-Leu-NH$_2$

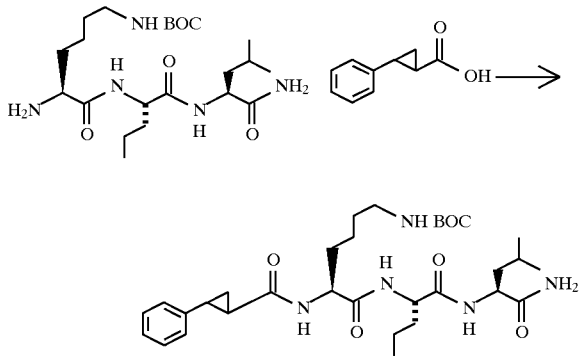

The acylation of (ε-BOC)Lys-Nva-Leu-NH$_2$ (43.6 mg, 0.095 mmol, the product of Example 8) by trans 2-phenylcyclopropane-1-carboxylic acid (26.0 mg, 0.160 mmol) was carried out as described in Example 10. The crude product was purified by elution from a Sephadex LH-20–100 (780×12.7 mm) column with methanol. The product was recovered as an oil. $^1$H NMR [400 MHz, d4 Methanol] Selected peaks: 7.13 (m, 5H), 4.32 (m, 1H), 4.2 (m, 2H), 2.98 (m, 2H), 2.32 (m, 1H), 1.94 (m, 1H), 0.88 (m, 9H). Mass spectrum [ESI, 80% CH$_3$CN/20% 0.01% aqTFA]: m/z=602.2.

EXAMPLE 17

α.[2-Phenylcyclopropyl-1-carbonyl]-Lys-Nva-Leu-NH$_2$

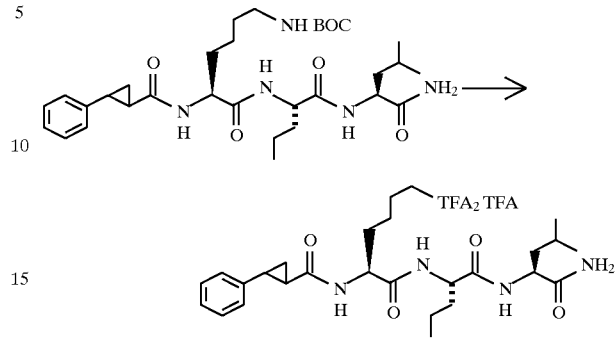

The deprotection of the BOC amine of Example 16 (34.0 mg, 0.057 mmol) was carried out as described in Example 13. Residual acetic acid was removed by azeotropic evaporation with toluene. The crude product was purified by preparatory reverse phase HPLC on an E. Merck LiChroprep RP-18 column with 0.1% TFA(aq): CH$_3$CN (62:38). Two diastereomers were separated. The absolute configurations are unknown. The early eluting product was recovered as an oil.

Isomer A: $^1$H NMR [300 MHz, d4 Methanol] Selected peaks: 7.13 (m,5H), 4.3 (m, 3H), 2.86 (t, 2H), 0.89(m, 9H). Mass spectrum [ESI, 80% CH$_3$CN/20% 0.01% aqTFA]: m/z=502.2.

The late eluting product was recovered as an oil.

Isomer B: $^1$H NMR [300 MHz, d4 Methanol] Selected peaks: 7.14 (m, 5H), 4.27 (m, 3H), 2.88 (t, 2H), 0.9 (m, 9H). Mass spectrum [ESI, 80% CH$_3$CN/20% 0.01% aqTFA]: m/z=502.2.

EXAMPLE 18

α-[2-Benzylcyclopropyl-1-carbonyl]-(ε-BOC)Lys-Nva-Leu-NH$_2$

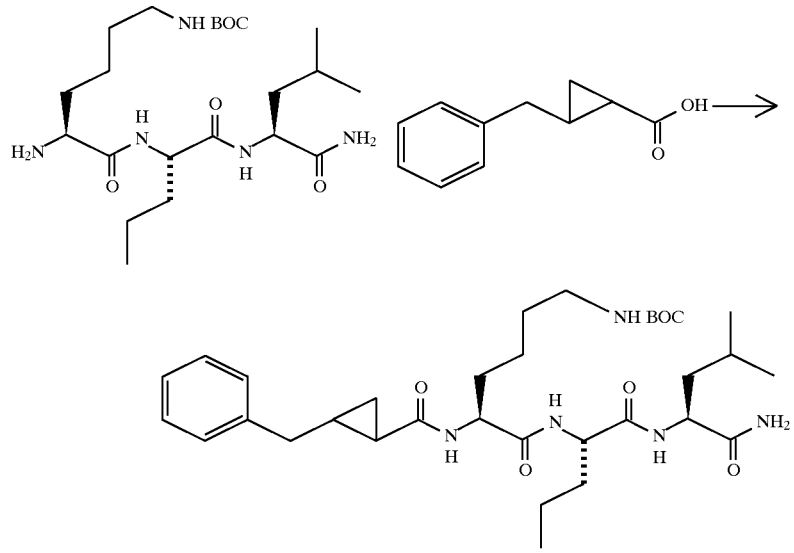

The acylation of (ε-BOC)Lys-Nva-Leu-NH$_2$ (30.1 mg, 0.066 mol, the product of Example 8) by 2-benzyl-1-cyclopropyl carboxylic acid (38.5 mg, 0.219 mmol, previously prepared from the hydrolysis of commercial ethyl 2-benzyl-1-cyclopropyl carboxylate) was carried out as described in Example 10. The crude product was purified by elution from a Sephadex LH-20-100 (780×12.7 mm) column using methanol. The product was recovered as an amorphous solid. $^1$H NMR [300 MHz, d4 Methanol] Selected peaks: 7.919 (m, 5H), 4.32 (m, 1H), 4.18 (m, 2H), 2.98 (m, 2H), 2.62 (m, 1H), 2.56 (m, 1H), 1.06 (m, 1H), 0.86 (m, 9H), 0.76 (m, 1H). Mass spectrum [ESI, 80% CH$_3$CN/20% 0.01% aqTFA]: m/z=616.3.

EXAMPLE 19

α-[2-Benzylcyclopropyl-1-carbonyl]-Lys-Nva-Leu-NH$_2$

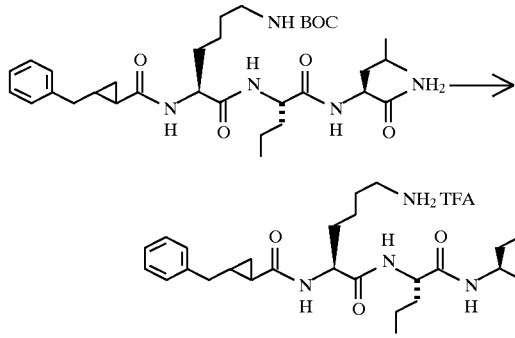

The deprotection of the BOC amine of Example 18 (32.6 mg, 0.053 nmmol) was carried out as described in Example 13. The crude product was purified by preparatory reverse phase HPLC on an E. Merck LiChroprep RP-18 (310×25 mm) column with 0.1% TFA(aq): CH$_3$CN (57:43) as eluent. The product was recovered as an amorphous solid. $^1$H NMR [400 MHz, d4 Methanol] Selected peaks: 7.23 (m, 5H), 4.34 (m, 1H), 4.27 (m, 2H), 2.9 (m, 2H), 1.11 (h, 1H), 0.92 (m, 9H), 0.81 (m, 1H). Mass spectrum [ESI, 80% CH$_3$CN/20% 0.01% aqTFA]: m/z=516.3.

EXAMPLE 20

α-[1-phenylcyclopropyl-1-carbonyl]-(ε-BOC)Lys-Nva-Leu-NH$_2$

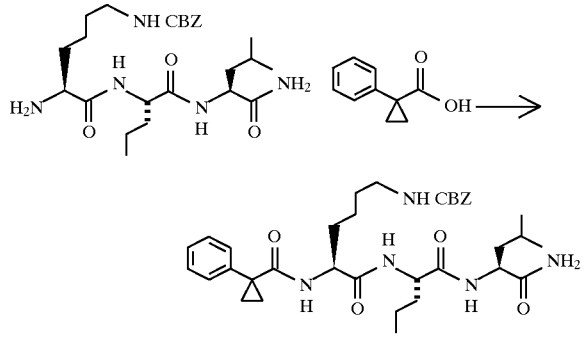

(ε-CBZ)-Lys-Nva-Leu-NH$_2$ is prepared by the general procedures typified by Examples 8 and 9 starting from (α-BOC)-(ε-CBZ)-Lysine. The acylation of (ε-CBZ)Lys-Nva-Leu-NH$_2$ (110.6 mg, 0.226 mmol.) by 1-phenyl-1-cyclopropyl carboxylic acid (44.3 mg, by 1-phenyl-1-cyclopropyl carboxylic acid (44.3 mg, 0.271 mmol) was carried out as described in Example 10. The crude product was purified by elution from a Sephadex LH-20-100 (780× 12.7 mm) column using methanol. The product was recovered as an amorphous solid. 1H NMR [300 MHz, d4 Methanol] Selected peaks: 7.31 (m, 10H), 5.01 (s, 2H), 4.28 (m, 2H), 4.16 (q, 1H), 3.01 (t, 2H), 0.85 (m, 9H). Mass spectrum [PBI-NH3/CI]: m/z=636.3.

EXAMPLE 21

α-[1-Phenylcyclopropyl-1-carbonyl]-Lys-Nva-Leu-NH$_2$

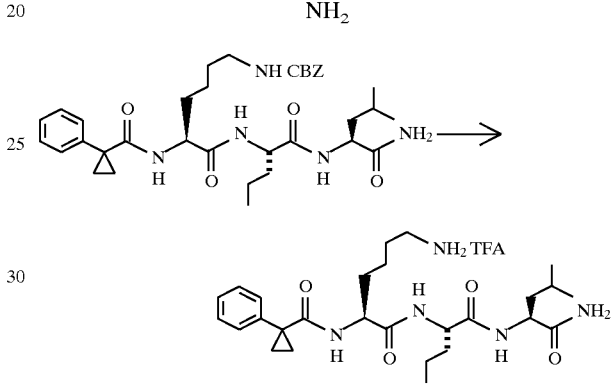

The CBZ protected amine of Example 20 (48.3 mg, 0.076 mmol) was dissolved in glacial acetic acid (6 mL) with Pd/C 10% (11.0 mg, ~20% w/w). The reaction flask was purged three times vacuum versus H$_2$ and stirred vigorously under one atm. of H$_2$ at room temperature. The reaction was typically complete after 1–2 hours as judged by TLC. The reaction mixture was filtered through a pad of Celite™ diatomaceous earth to remove the catalyst and concentrated i. vac. Residual acetic acid is removed as the toluene azeotrope i. vac. The product was recovered as an oil. 1H NMR [400 MHz, d4 Methanol] Selected peaks: 7.39 (m, 5H), 4.37 (5, 1H), 4.31 (dd, 1H), 4.21 (q, 1H), 2.86 (t, 2H), 0.93 (m, 6H), 0.88 (d, 3H). Mass spectrum [ESI, 80% ACN/20% 0.01% aqTFA] m/z=502.2.

EXAMPLE 22

α-[(1R,2S)-1-Cyclohexylcyclopropyl-1-carbonyl]-Lys-Nva-Leu-NH$_2$

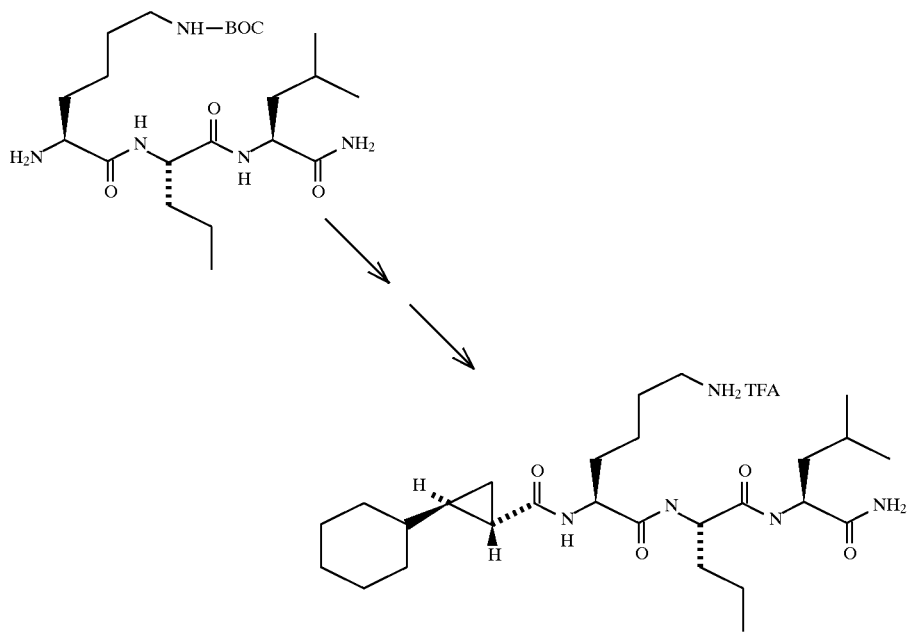

The acylation of the (ε-BOC)Lys-Nva-Leu-NH₂ (35.6 mg, 0.078 mmol, the product of Example 8) by (1R,2S)-2-Cyclohexylcyclopropyl-1-carboxylic acid (16.4 mg, 0.098 mmol) was carried out as described in Example 10. The crude product was purified by elution from a Sephadex LH-20-100 (780×12.7 mm) column with methanol. The product was recovered as an oil.

The deprotection of the BOC amine (7.2 mg, 0.012 mmol) was carried out as described in Example 9. The crude product was purified by preparatory reverse phase HPLC on an E. Merck LiChroprep RP-18 (310×25 mm) column with 0.1% TFA(aq): CH₃CN (60:40) as eluent. The product was recovered as an oil. Characteristic NMR Resonances; ¹H NMR 400 MHz (CD₃OD); 8.02 (m, 2 NH protons), 4.35 (m, 1H), 4.27 (overlapping m's, 2H), 2.92 (t, 2H, J =7.5 Hz), 0.7 (m's, 2H, cycloprpyl H's).Mass spectrum [ESI 80% CH₃CN/0.1% Aq TFA]: m/z 508.3, M+1 for 507.4 calculated mass.

EXAMPLE 23

α-[Benzylureal]-(ε-CBZ)Lys-Nva-Leu-NH₂

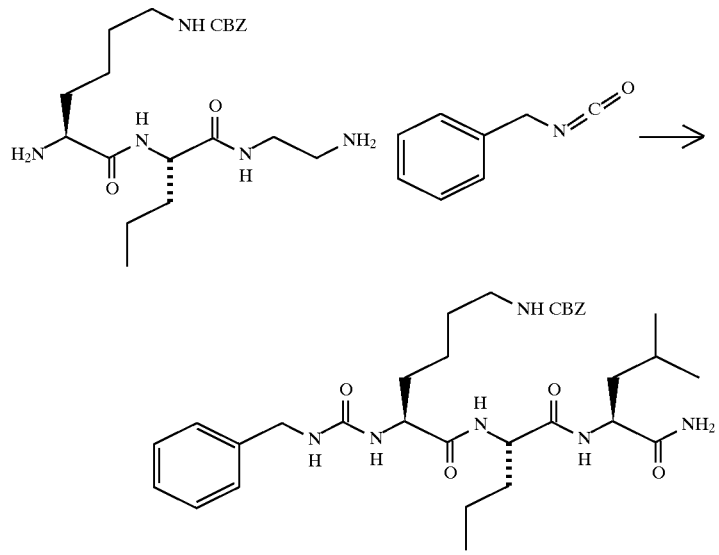

(ε-CBZ)Lys-Nva-Leu-NH₂(40.9 mg, 0.83 mmol, see Example 20) was dissolved in dry methylene chloride (5 mL) at 0° C. Benzyl isocyanate (12.0 µL, 0.098 mmol) was added to the solution. After 1.5 hours, reaction was warmed to room temperature and stirred ½ hour. The mixture was concentrated i. vac. The crude product was purified by elution from a Sephadex LH-20-100 (700×12.5 mm) column using methanol. The product was recovered as an amorphous solid. 1H NMR [300 MHz, d6 DMSO] Selected peaks: 7.23 (m, 10H), 4.94 (s, 2H), 2.9 (m, 2H), 0.77 (m, 9H). Mass spectrum [ESI, 80% ACN/20% 0.01% aqTFA] m/z=625.2.

EXAMPLE 24

α-[Benzylureal]-Lys-Nva-Leu-NH$_2$

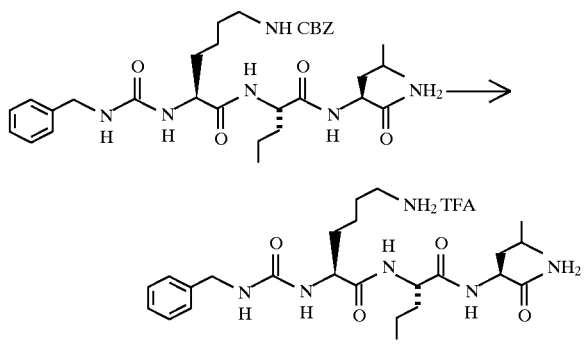

The deprotection of the CBZ protected amine prepared according to the procedures of Example 23 (40.5 mg, 0.066 mmol) was carried out as described in Example 21. The crude product was purified by preparatory reverse phase HPLC on an E. Merck LiChroprep RP-18 (310×25 mm) column with 0.1% TFA(aq): CH$_3$CN (62:38) as eluent. The product was obtained as an amorphous solid. 1H NMR [400 MHz, d4 Methanol] Selected peaks: 7.27 (m, 5H), 4.35 (m, 1H ), 4.32 (d, 2H), 4.27 (m, 1H), 4.17 (t, 1H ), 2.91 (t, 1H ), 0.94 (t, 3H), 0.89 (dd, 6H). Mass spectrum [ESI, 80% ACN/20% 0.01% aqTFA] m/z=492.2.

EXAMPLE 25

α-[2-methyl-3-phenylpropionyl]-(ε-CBZ)Lys-Nva-Leu-NH$_2$

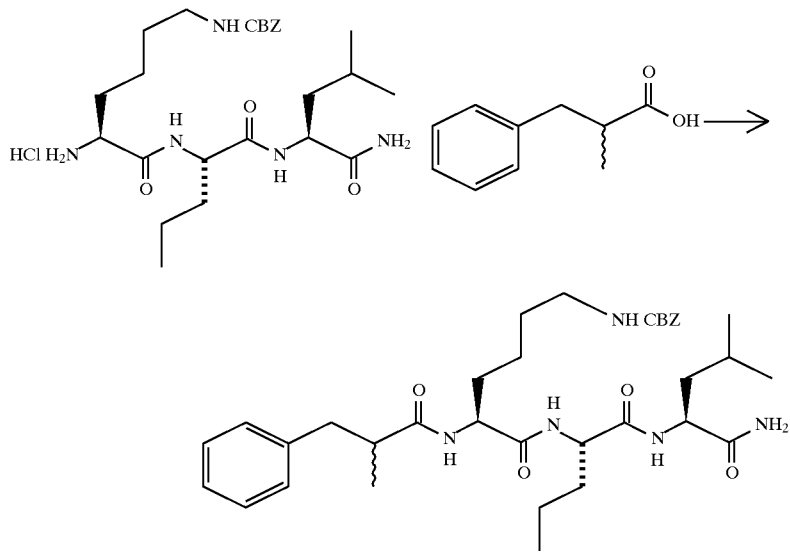

The acylation of (ε-CBZ)Lys-Nva-Leu-NH$_2$ (60.1 mg, 0.114 mmol, see Example 20) by (+)-α-methyl hydrocinnamic acid (23.5 mg, 0.143 mmol) was carried out as described in Example 10. The crude product was purified by elution from a Sephadex LH-20-100 (780×12.7 mm) column with methanol. The product was recovered as an oil. $^1$H NMR [300 MHz, d4 Methanol] Selected peaks: 7.17 (m, 10H), 4.32 (m, 1H), 4.18 (m, 1.5 m), 4.06 (m, 0.5H), 1.06 (dd, 3H), 0.86 (m, 9H). Mass spectrum [ESI, 80% CH$_3$CN/20% 0.01% aqTFA] m/z=638.2.

EXAMPLE 26

α-[2-methyl-3-phenylpropionyl]-Lys-Nva-Leu-NH$_2$

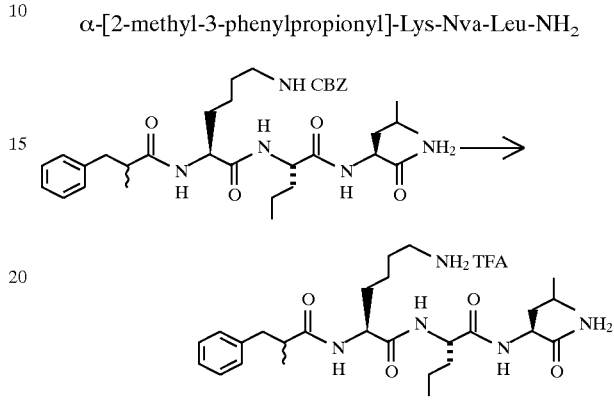

The deprotection of the CBZ amine produced in Example 25 (50.0 mg, 0.078 mmol) was carried out as described in Example 21. The crude product was purified by preparatory reverse phase chromatography on an E. Merck LiChroprep RP-18 (310×25 mm) column with 0.1% TFA (aq):CH$_3$CN (65:35) as eluent. Two diastereomers were separated. The absolute configurations are unknown.

The early eluting product was recovered as an oil. Isomer A: $_1$H NMR [400 MHz, d4 Methanol] Selected peaks: 7.22 (m, 5H), 4.35 (m, 1H), 4.26 (q, 1H), 4.19 (m, 1H), 2.69 (m, 2H), 1.16 (d, 3H), 0.95 (d, 3H), 0.93 (t, 3H), 0.90 (d, 3H). Mass spectrum [ESI, 80% CH$_3$CN/20% 0.01% aqTFA] m/z=504.2.

The late eluting product was recovered as an oil. Isomer B: $^1$H NMR [400 MHz, d4 Methanol] Selected peaks: 7.22 (m, 5H), 4.3 (m, 3H), 2.69 (m, 1H), 2.61 (m, 1H), 1.1 (d, 3H), 0.95 (d, 3H), 0.94 (t, 3H), 0.91 (d, 3H). Mass spectrum [ESI, 80% CH$_3$CN/20% 0.01% aqTFA] m/z=504.2.

EXAMPLE 27

α-[2-(t-Butylsulfony)methyl-3-phenylpropionyl]-(ε-BOC)Lys-Nva-Leu-NH$_2$

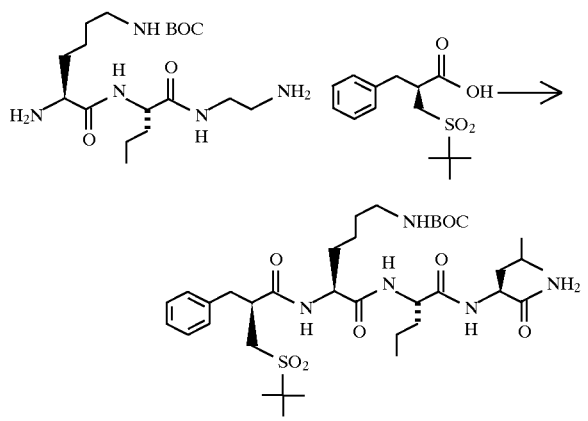

The acylation (ε-BOC)Lys-Nva-Leu-NH$_2$ (36.4 mg, 0.80 mmol, the product of Example 8) by (2R)-(t-butylsulfonyl)-3-phenylpropanoic acid (31.6 mg, 0.11 mmol) was carried out as described in Example 10. The crude product was purified by elution from a Sephadex LH-20-100 (780×12.7 mm) column with methanol. The product was recovered as an oil. $^1$H NMR [300 MHz, d4 Methanol] Selected peaks: 7.23 (m, 5H), 4.31 (m, 1H), 4.15 (m, 2H), 1.26 (s, 9H), 0.9 (d, 3H), 0.85 (t, 3H), 0.84 (d, 3H). Mass spectrum [ESI, 80% CH$_3$CN/20% 0.01% aqTFA] m/z=724.2.

EXAMPLE 28

α-[2-(t-Butylsulfony)methyl-3-phenylpropionyl]-Lys-Nva-Leu-NH$_2$

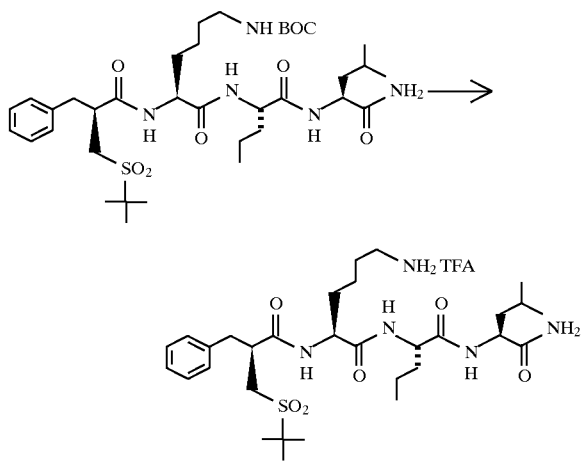

The deprotection of the BOC amine of Example 27 (30.1 mg, 0.042 mmol) was carried out as described in Example 9. The crude product was purified by preparatory reverse phase HPLC on an E. Merck LiChroprep RP-18 (310×25 mm) column with 0.1% TFA(aq):CH$_3$CN (62:38) as eluent. The product was recovered as an oil. $^1$H NMR [400 MHz, d4 Methanol] Selected peaks: 7.28 (m, 5H), 4.3 (m, 3H), 3.05 (m, 2H), 2.91 (t, 2H), 2.76 (dd,1H), 1.29 (s, 9H), 0.95 (m, 6H), 0.9 (d, 3H). Mass spectrum [ESI, 80% CH$_3$CN/20% 0.01% aqTFA] m/z=624.2.

EXAMPLE 29

α-[2,2-dimethyl-3-phenylpropionyl]-(ε-BOC)Lys-Nva-Leu-NH$_2$

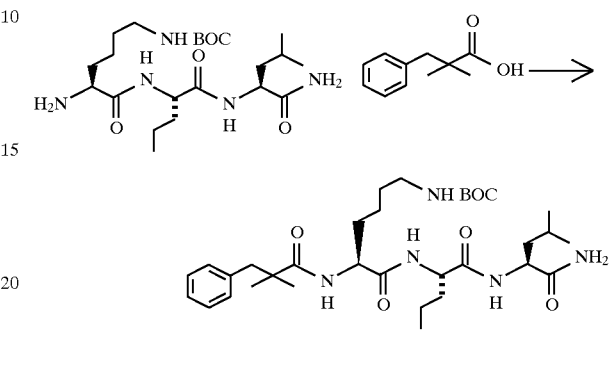

The acylation of (ε-BOC)Lys-Nva-Leu-NH$_2$ (30.7 mg, 0.067 mmnol, product of Example 8) by 2,2-dimethyl-3-phenylpropionic acid (17.0 mg, 0.096 mmol, previously prepared by treating 2,2-dimethyl-3-phenyl propanol with Jones reagent) was carried out as described in Example 10. The crude product was purified by elution from a Sephadex LH-20 (780×12.7 mm) column with methanol. The product was recovered as an oil. $^1$H NMR [400 MHz, d4 Methanol] Selected peaks: 7.18 (m, 5H), 4.38 (m, 1H) 4.28 (m, 2H), 2.99 (t, 2H), 2.83 (2H, ABq, Δδ 60 Hz, JAB=13.2 Hz), 0.94 (m, 6H), 0.9 (d, 3H). Mass spectrum [ESI, 80% CH$_3$CN/20% 0.01% aqTFA] m/z=618.3.

EXAMPLE 30

α-[2,2-dimethyl-3-phenylpropionyl]-Lys-Nva-Leu-NH$_2$

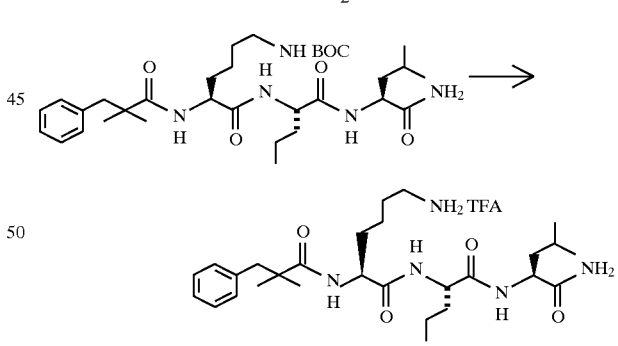

The deprotection of the BOC amine prepared according to the procedures of Example 29 (31.9 mg, 0.052 mmol) was carried out as described in Example 9. The crude product was purified by preparatory reverse phase HPLC on an E. Merck LiChroprep RP-18 (310×25 mm) column with 0.1% TFA(aq):CH$_3$CN (62:38) as eluent. The product was recovered as an oil. $^1$H NMR [400 MHz, d4 Methanol] Selected peaks: 8.12 (m, 2H), 7.18 (m, 5H), 4.36 (m, 2H), 4.31 (m, 1H), 2.88 (t, 3H), 2.83 (2H, ABq, Δδ=51.3 Hz, JAB=13.2 Hz), 1.18 (d, 6H), 0.95 (m, 6H), 0.9 (d, 3H). Mass spectrum [ESI, 80% CH$_3$CN/20% 0.01% aqTFA] m/z=519.3.

EXAMPLE 31

α-[3S-methyl-3-phenylpropionyl]-(ε-CBZ)Lys-Nva-Leu-NH₂

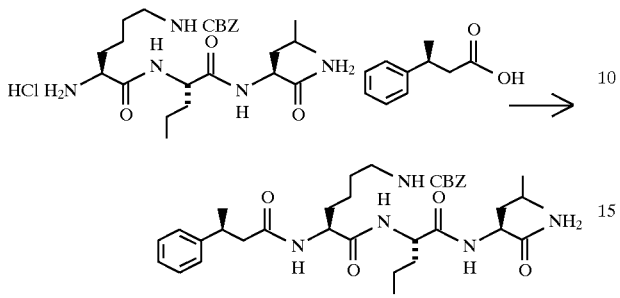

The acylation of (ε-CBZ)Lys-Nva-Leu-NH₂ (36.6 mg, 0.070 mmol, see Example 20) by (3S)methyl-3-phenylpropionic acid (13.0 μL, 0.085 mmol) was carried out as described in Example 10. The crude product was purified by elution from a Sephadex LH-20-100 (780×12.7 mm) column with methanol. The product was recovered as an oil. ¹H NMR [300 MHz, d4 Methanol] Selected peaks: 7.20 (m, 10H), 4.82 (s, 2H), 4.3 (m, 1H), 4.16 (m, 2H), 3.05 (t, 2H), 2.45 (m, 2H),1.19 (d, 3H), 0.87 (m, 9H). Mass spectrum [ESI, 80% CH₃CN/20% 0.01% aqTFA] m/z=638.

EXAMPLE 32

α-[3S-methyl-3-phenylpropionyl]-Lys-Nva-Leu-NH₂

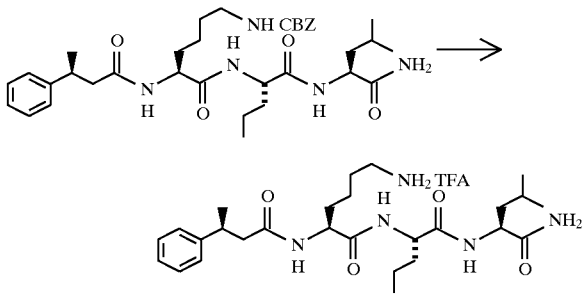

The deprotection of the CBZ amine prepared according to the procedures of Example 31 (26.7 mg, 0.042 mmol) was carried out as described in Example 21. The crude product was purified by preparatory reverse phase HPLC on an E. Merck LiChroprep RP-18 column with 0.1% TFA (aq) :CH₃CN (62:38). The product was recovered as an oil. ¹H NMR [400 MHz, d4 Methanol] Selected peaks: 7.22 (m, 5H), 4.27 (m, 3H), 3.23 (q, 1H ), 2.89 (t, 2H), 2.51 (m, 2H), 1.25 (d, 3H), 0.95 (d, 3H), 0.93 (t, 3H), 0.91 (d, 3H). Mass spectrum [ESI, 80% CH₃CN/20% 0.01% aqTFA] m/z=504.2.

EXAMPLE 33

α-[3R-methyl-3-phenylpropionyl]-(εBOC)Lys-Nva-Leu-NH₂

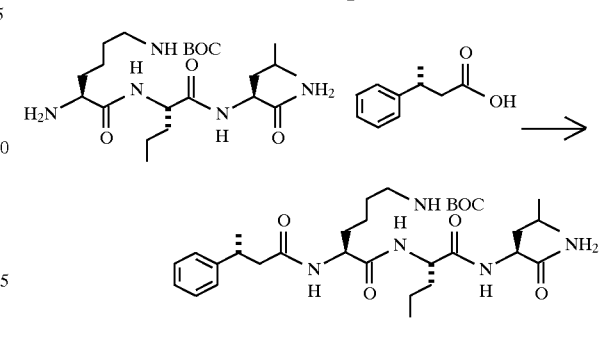

The acylation of (ε-BOC)Lys-Nva-Leu-NH₂ (31.3 mg, 0.68 mmol, product of Example 8) by (R)-β-methyl dihydrocinnamic acid (13.0 μL, 0.085 mmol) was carried out as described in Example 10. The crude product was purified by elution from a Sephadex LH-20-100 (780×12.7 mm) column with methanol. The product was recovered as an oil. ¹H NMR [400 MHz, d4 Methanol] Selected peaks: 7.23 (m, 5H), 4.37 (m, 1H), 4.26 (q, 1H), 4.13 (m, 1H), 3.21 (h, 1H ), 2.94 (m, 2H), 2.5 (m, 2H), 1.27 (d, 3H), 0.92 (m,9H). Mass spectrum [ESI, 80% CH₃CN/20% 0.01% aqTFA] m/z=604.3.

EXAMPLE 34

α-[3R-methyl-3-phenylpropionyl]-Lys-Nva-Leu-NH₂

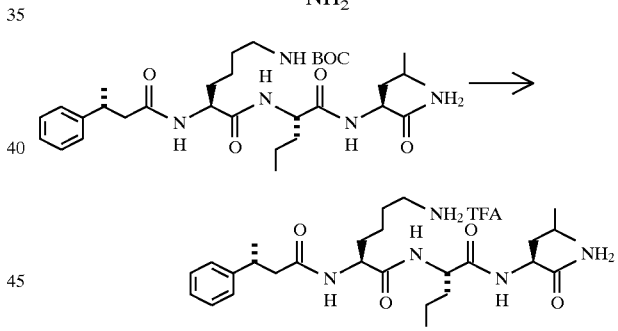

The deprotection of the BOC amine prepared according to the procedures of Example 33 (33.3 mg, 0.055 mmol) was carried out as described in Example 9. The crude product was purified by preparatory reverse phase HPLC on an E. Merck LiChroprep RP-18 column with 0.1% TFA(aq) :CH₃CN (62:38). The product was recovered as an oil. ¹H NMR [400 MHz, d4 Methanol] Selected peaks: 7.27 (m, 5H), 4.36 (m, 1H), 4.25 (m, 1H), 3.22 (h, 1H ), 2.8 (t, 2H), 2.51 (m, 2H), 1.27 (d, 3H), 1.1 (m, 2H), 0.95 (m, 6H), 0.91 (d, 3H). Mass spectrum [ESI, 80% CH₃CN/20% 0.01% aqTFA] m/z=504.2.

EXAMPLE 35

α-[3R-methyl-3-cyclohexylpropionyl](ε-BOC)Lys-Nva-Leu-NH₂

Step 1: Preparation of 3R-methyl-3-cyclohexylpropionic acid

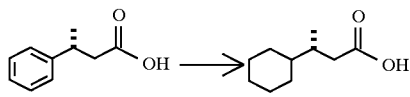

Commercially available (R)-β-Methyl dihydrocinnamic acid (5.35 g, 0.033 mol) was dissolved in glacial acetic acid (15 ml). $PtO_2$ (283.6 mg, cat.) was added to the solution. The reaction flask was purged three times vacuum versus $H_2$ and stirred vigorously under one atm. of $H_2$ at 60° C. The reaction proceeded very slowly. The hydrogenation was continued with periodic additions of fresh $PtO_2$ until consumption of starting material was judged to be completed by TLC. The mixture was filtered through a pad of Celite™ diatomaceous earth and rinsed with glacial acetic acid. The solution was concentrated i. vac. and residual acetic acid removed as the toluene azeotrope i. vac. The product was recovered as an oil. $^1$H NMR [400 MHz, d4 Methanol] Selected peaks: 1.85 (m, 1H), 0.91 (d, 3H). Mass spectrum [Probe-EI] m/z=171.1.

Step 2: Preparation of α-[3R-methyl-3-cyclohexylpropionyl](ε-BOC) Lys Nva Leu-$NH_2$

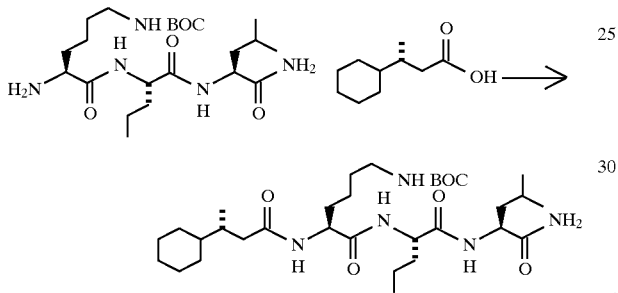

The acylation of (ε-BOC)Lys-Nva-Leu-$NH_2$ (37.9 mg, 0.083 mmol, product of Example 8) by 3R-methyl-3-cyclohexylpropionic acid (24.5 mg, 0.145 mmol, from Step 1) was carried out as described in Example 10. The crude material was purified by elution from a Sephadex LH-20-100 (700×25 mm) column with methanol. The product was recovered as an oil. $^1$H NMR [400 MHz, d4 Methanol] Selected peaks: 4.4 (m, 1H), 4.26 (m, 2H), 3.02 (t, 2H). Mass spectrum [ESI, 80% $CH_3CN$/20% 0.01% aqTFA] m/z=610.3.

EXAMPLE 36

α-[3R-methyl-3-cyclohexylpropionyl]-Lys-Nva-Leu-$NH_2$

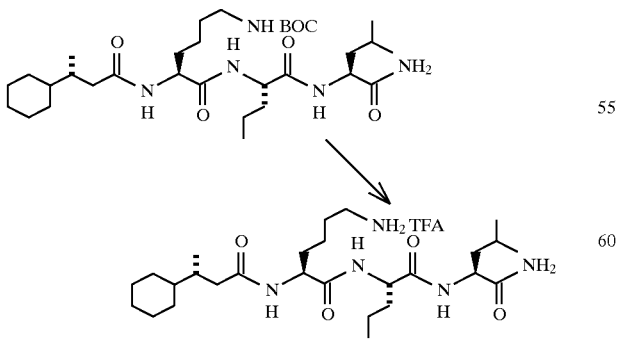

The deprotection of the BOC amine produced according to the procedures of Example 35 (38 mg, 0.062 mmol) was carried out as described in Example 9. The crude product was purified by preparatory reverse phase HPLC on an E. Merck LiChroprep RP-18 column with 0.1% TFA(aq) :$CH_3CN$ (58:42). The product was recovered as an oil. $^1$H NMR [400 MHz, d4 Methanol] Selected peaks: 4.33 (m, 3H), 2.92 (t, 2H), 2.30 (dd, 1H), 2.02 (dd, 1H), 0.86 (d, 3H). Mass spectrum [ESI, 80% $CH_3CN$/20% 0.01% aqTFA] m/z=510.2

EXAMPLE 37

α-(3-Phenylpropyl)-(ε-BOC)Lys-Nva-Leu-$NH_2$

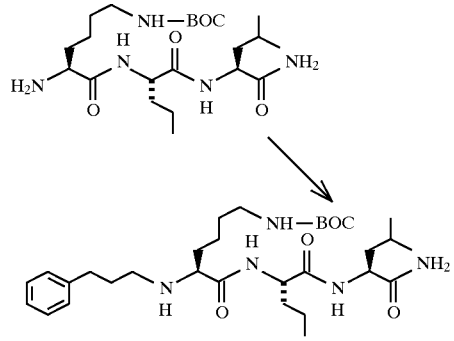

The (ε-BOC)Lys-Nva-Leu-$NH_2$ (1.0 Eq, 38 mg, 0.083 mmol, the product of Example 8) was dissolved in $CH_3OH$ (400 μL) and glacial acetic acid (2.0 Eq, 9.5 μL, 0.166 mmol) was added followed by 3-phenylpropionaldehyde (1.0 Eq, 10.9 μL, 0.083 mmol). The solution was stirred briefly at RT. A 1M THF solution of $NaCNBH_3$ (1.2 Eq, 100 μL, 0.1 mmol) was added and the mixture stirred one hour at RT. The reaction mixture was diluted with 2 mL of saturated aqueous sodium bicarbonate and ethyl acetate. The aqueous layer was extracted three times with ethyl acetate. Organic layers were combined and washed with $H_2O$, 0.25M citrate buffer (pH=2.3), sodium bicarbonate and brine. The combined extracts were dried over $Na_2SO_4$, filtered and concentrated i. vac. The product was purified by elution from a Sephadex LH-20-100 column (780×12.7 mm) with methanol. The product was recovered as an oil. Characteristic NMR Resonances; $^1$H NMR 400 MHz ($CD_3OD$); 7.2 (m, 5H), 4.39 (overlapping m's, 2H), 3.08 (t, 1H, J=6.6 Hz), 3.00 (t, 2H, J=6.9 Hz), 2.63 (m, 2H, 3-phenylpropyl α-H's), 2.49 (m, 2H, 3-phenylpropyl benzylic H's), 1.42 (s, 9H), 0.94 (overlapping methyl resonances, 6H), 0.90 (d, 3H, J=6.5 Hz).

EXAMPLE 38

α-[3-Phenylpropyl]-Lys-Nva-Leu-$NH_2$

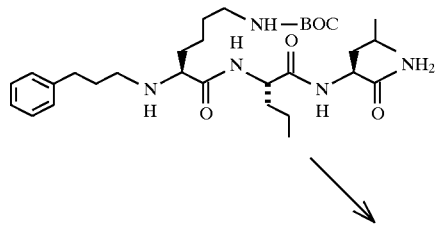

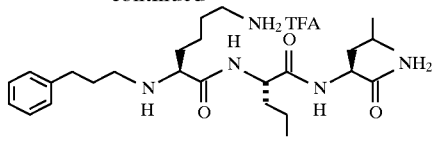

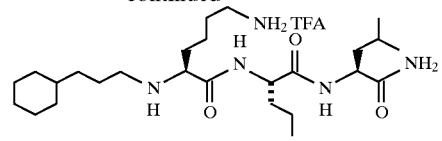

The deprotection of the BOC amine produced according to the procedures of Example 37 (15.4 mg, 0.027 mmol) was performed as for Example 9. The crude product was purified by preparatory reverse phase chromatography on an E. Merck LiChroprep RP-18 (310×25 mm) column with 0.1% TFA (aq):CH$_3$CN (68:32) as eluent. The product was recovered as an amorphous solid. Characteristic NMR Resonances; $^1$H NMR 400 MHz (CD$_3$OD); 8.26 (NH d, 2H, J=7.6 Hz), 8.27 (m, 2H), 7.29 (m, 3H), 4.34 (overlapping m's, 2H), 3.88 (m, 1H), 2.83–3.0 (overlapping m's, 4H), 2.71 (t, 2H, J=7.4 Hz), 0.95 (t, 3H, J=7.3 Hz), 0.95 (d, 3H, J=6.6 Hz), 0.91 (d, 3H, J=6.6 Hz). Mass spectrum [ESI 80% CH$_3$CN /0.1% Aq TFA]: m/z476.2, M+1 for 475.4 calculated mass.

EXAMPLE 39

α-[3-Cyclohexylpropyl]-(ε-BOC)Lys-Nva-Leu-NH$_2$

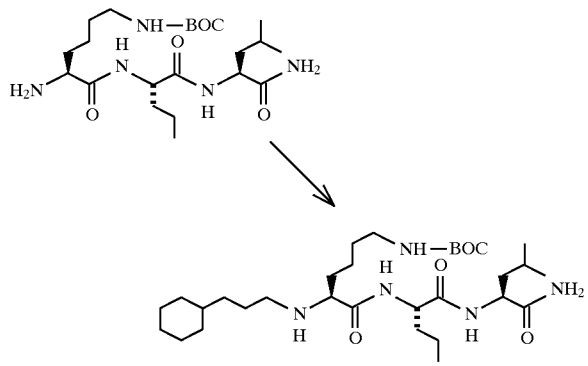

The reductive alkylation of the (ε-BOC)Lys-Nva-Leu-NH$_2$ (1.0 Eq, 0.083 mmol, 38 mg, product of Example 8) with 3-cyclohexylpropionaldehyde (1.0 Eq, 0.083 mmol, 12.7 μL) was performed as described in Example 38. The product was purified by elution from a Sephadex LH-20-100 column (780×12.7 mm) with methanol. The product was recovered as an oil. Characteristic NMR Resonances; $^1$H NMR 400 MHz (CD$_3$OD); 4.4 (overlapping m's, 2H), 3.27 (t, 1H, partially obscured), 3.01 (t, 2H, J=6.5 Hz), 2.55 (t, 2H, J=7.6 Hz), 0.95 (t, 3H, J=7.3 Hz), 0.95 (d, 3H, J=6.5 Hz), 0.91 (d, 3H, J=6.5 Hz).

EXAMPLE 40

α-[3-Cyclohexylpropyl]-Lys-Nva-Leu-NH$_2$

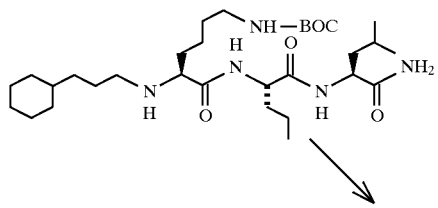

The deprotection of the BOC amine produced according to the procedures of Example 39 (15 mg, 0.026 mmol) was performed as for Example 9. The crude product was purified by preparatory reverse phase chromatography on an E. Merck LiChroprep RP-18 (310×25 mm) column with 0.1% TFA (aq):CH$_3$CN (60:40) as eluent. The product was recovered as an amorphous solid. Characteristic NMR Resonances; $^1$H NMR 400 MHz (CD$_3$OD); 8.75 (d, NH), 8.27 (d, NH), 4.38 (dd, 1H, J=9.2, 5.3 Hz), 4.37 (m, 1H), 3.92 (dd, 1H, J=8.4, 4.8 Hz), 2.96 (m, 2H), 3.91 (2H, AB of ABM$_2$ partially obscured), 0.97 (t, 3H, J=7.3 Hz), 0.96 (d, 3H, J=6.5 Hz), 0.92 (d, 3H, J=6.5 Hz). Mass spectrum [ESI 80% CH$_3$CN/0.1% Aq TFA]: m/z 482.2, M+1 for 481.4 calculated mass.

EXAMPLE 41

α-[trans-2-Cyclohexylcyclopropyl-1-methyl]-Lys-Nva-Leu -NH$_2$

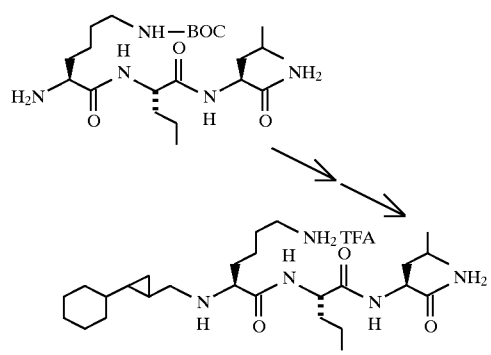

The reductive alkylation of (ε-BOC)Lys-Nva-Leu-NH$_2$ (35 mg, product of Example 8) by (±)-trans-3-cyclohexylcyclopropyl-1-carboxaldehyde (11.7 mg) was performed as described in Example 37. The product was purified by elution from a Sephadex LH-20-100 column (780×12.7 mm) with methanol. The material obtained was deprotected without further characterization.

The deprotection of the BOC amine was carried out as described in Example 9. The crude product was purified by preparatory reverse phase HPLC on an E. Merck LiChroprep RP-18 (310×25 mm) column with 0.1% TFA(aq):CH$_3$CN (70:30) as eluent. The product was recovered as an oil, as one to one mixture of isomers.

Characteristic NMR Resonances; $^1$H NMR 400 MHz (CD$_3$OD); 4.37 (dd, 2H, J=9.2, 5.5 Hz), 4.36 (m, 1H), 3.91 (m, 1H), 2.95 (m, two adjacent triplets, 2H), 2.85 (2H, AB of ABX, C isomer, Δδ=149 Hz, JAB=13 Hz, JAX=6.1 Hz, JBX=8.9 Hz), 2.83 (2H, AB of ABX, D isomer, Δδ=249 Hz, JAB=13 Hz, JAX=6.0 Hz, JBX=9.3 Hz), 0.96 (t, 3H, J=7 Hz), 0.95 (d, 3H, overlaps t), 0.91 ( d, 3H, J=6.5 Hz), 0.5–0.7 (overlapping m's, 4H, cyclopropyl H's). Mass spectrum [ESI 80% CH$_3$CN/0.1% Aq TFA]:m/z 494.3, M+1for 493.4 calculated mass.

EXAMPLES 42–52

General Synthetic Access to α-Aza-p2epntide Isosteres or acyl carbazates and carbamates.

In addition to the other strategies described in this invention to reduce susceptibility to proteases, α-aza-peptide isosteres, or N-alkylcarbazates and carbamates have been incorporated to protect the tetra peptide mimic from protease degradation.

FIG. 1 shows the structure and nomenclature of the α-Aza-peptide Isostere function.

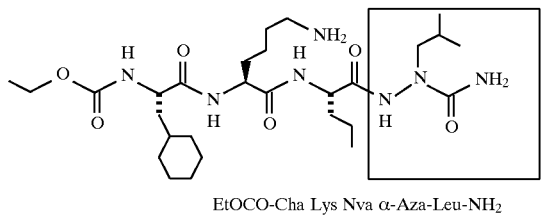

EtOCO-Cha Lys Nva α-Aza-Leu-NH$_2$

Although the (α-aza-amino acid isostere function may be incorporated at any of the potential protease cleavage sites, terminal substitutions are most likely to provide maximum utility for protection from enzymatic cleavage, based on published investigation. See ref. below for enzyme stability studies.

1) Dutta, A. S.; Giles, M. B. *J. Chem. Soc. Perkin* 1 1976, 244–248.
2) Oehme, P.; Katzenwinkel, S.; Vogt, W. E.; Niedrich, H. *Experentia*, 1973, 29, 947–948.
3) Oehme, P.; Bergmann, J.; Niedrich, H.; Jung, F.; Menzel, G. *Acta Biol. Med. Germ.* 1970,25, 613–625.
4) Wergin, A. *Naturwissenschaften* 1965,52, 34.

The general synthesis and properties of the class are well covered in the reviews and articles referenced below.

5) Gante, J. *Synthesis* 1989, 405–413. Review
6) Gante, *J. Chemische Berichte* 1965 98, 540–547.
7) Quibell, M.; Turnell, W. G.; Johnson, T. *J. Chem. Soc. Perkin* 1 1993, 2843–2849.
8) Folkers, K; Bowers, C. Y.; Lutz, W. B.; Friebel, K.; Kubiak, T.; Schircks, B.; Rampold, G. Z. *Naturforsch.* 1982, 37b, 1075–1081.
9) Dutta, A. S.; Morley, J. S. *J. Chem. Soc. Perkin* 1 1975, 1712–1720.

Synthesis of the carboxy terminal isostere is approachable from several routes. Complete elaboration of an alkylsemicarbazide or alkylcarbazate followed by coupling under conditions similar to normal peptide coupling methods is one practical route. For conditions where this route is not suitable, or where a series of analogs is desired, alkylation of a di- or tripeptide hydrazide followed by acylation, and further elaboration as appropriate, is also practical.

The route in Scheme I below relies only on the availability of a desired aldehyde or ketone, and is quite general. Similar reductive alkylations are well known. See ref. (10) below.

10) Borch, R. F.; Bernstein, M. D.; Durst, H. D. *J. Am. Chem. Soc.* 1971, 93, 2897–2904.

The protected hydrazine derivative, either the BOC hydrazine [t-butylcarbazate] as shown in Scheme I below, or the analogous CBZ hydrazine [benzylcarbazate], is typically dissolved in methanol at room temperature or below with one equivalent of the desired aldehyde or ketone. Glacial acetic acid is added in excess to facilitate the formation of the imminium intermediate and its subsequent reduction. A slight excess of a 1 molar solution of sodium cyanoborohydride is added to reduce the imminium intermediate to the desired alkylated carbazate. Minor quantities of dialkylation products are removed by chromatography.

Reaction with chloroformates or similar agents and subsequent deprotection lead to carbazoic acid derivatives, or α-aza-amino acid ester isosteres. In the example of Scheme I, the carbazate may be treated with a slight excess of the alkyl chloroformate either in two phase mixture of methylene chloride and an aqueous base, or in homogeneous solution of dioxane and an aqueous base. Treatment of the alkylated carbazate with potassium cyanate in the presence of a protic acid, for instance in dioxane solution with an excess of 2N hydrochloric acid leads to the semicarbazide analog, or α-aza-amino acid amide isostere. Treatment with other acylating reagents such as acid chlorides under similar conditions lead to analogs with less exact relationships to natural amino acids.

The shorter route in Scheme II is preferred when the desired hydrazine is commercially available. By a method similar to the example of Scheme I, a slight excess of the unprotected hydrazine or hydrazine salt may be treated with the alkyl chloroformate either in two phase mixture of methylene chloride and an aqueous base, or in homogeneous solution of methylene chloride in the presence of a tertiary amine base. Several studies have shown that the monoalkyl hydrazines are selectively or exclusively acylated on the substituted nitrogen. See review by Gante above.

Scheme I

Minor Di-alkylation

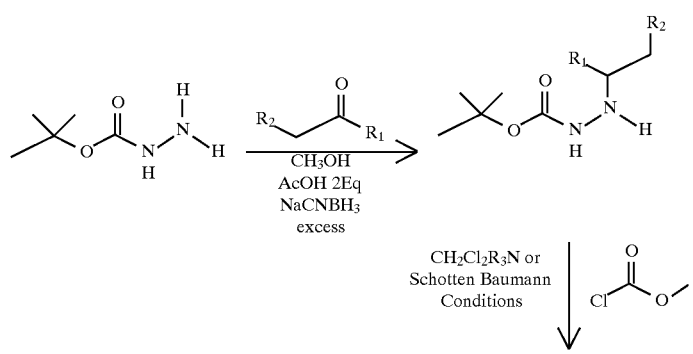

-continued
Scheme I
Scheme II
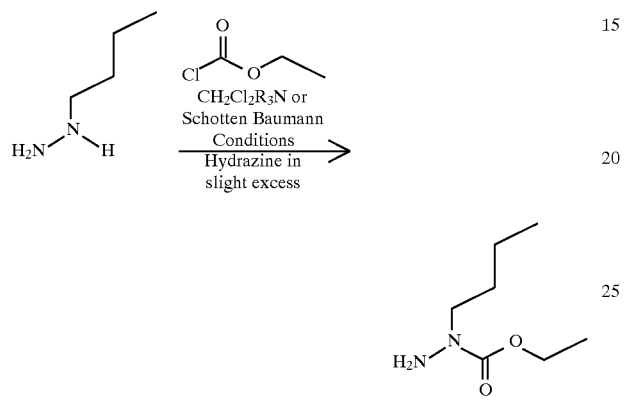
Where the hydrazide starting material is a di- or tripeptide hydrazide, the completely elaborated isostere is prepared as in Scheme III.
Scheme III
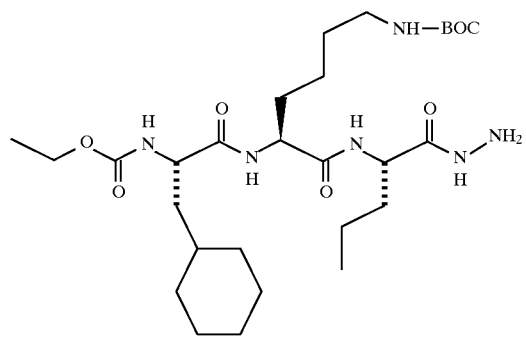
1) 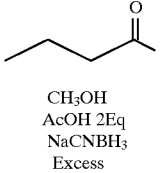
Typically
50–60%
yield
CH₃OH
AcOH 2Eq
NaCNBH₃
Excess
2) 
Both Steps
Typically
>90%
yield
3) TFA
CH₂Cl₂
0° C.

-continued
Scheme III

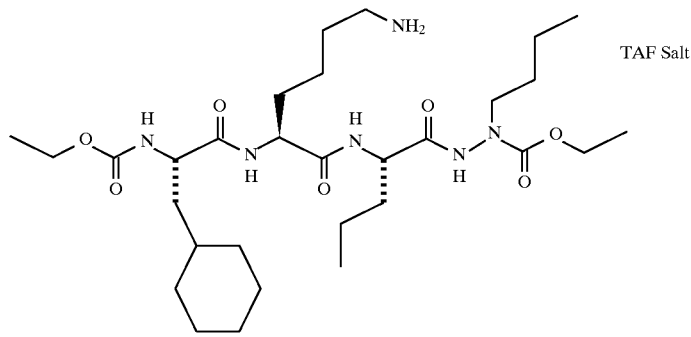
TAF Salt

The peptide hydrazide may be prepared by hydrazine resin cleavage from the usual solid phase synthesis, or hydrazides may be prepared by the solution phase coupling of either t-Butyl or benzylcarbazate under the usual carbodiimide HOBT peptide coupling conditions followed by deprotection. The steps required for the conversion of the resulting peptide hydrazide analogs produced to the desired final products are substantially the same as those described above for the simpler carbazate derivatives. Some dialkylation product is also typically obtained by this route, and must be removed chromatographically.

EXAMPLE 42

EtOCO-Cha-(ε-BOC)Lys-Nva-o-AzaLeu-NH₂
Step 1: Preparation of CBZ-α-AzaLeu-NH₂

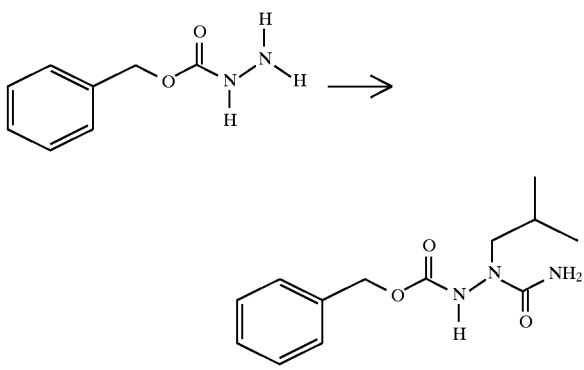

Benzyl carbazate (1.0 Eq, 1.0 g, 6 mmol) was dissolved CH₃OH (12 mL) and cooled to 0° C. Isobutyraldehyde (1.0 Eq, 434 mg, 6 mmol) and acetic acid (2.0 Eq, 0.7 mL, 12 mmol) were added and the reaction mixture stirred briefly. A 1M THF solution of NaCNBH₃ was added and the mixture was allowed to come to RT and stirred one hour. The mixture was poured into H₂O and CH₂Cl₂ and the aqueous phase extracted three times CH₂Cl₂. The combined organic phases were washed with H₂O , pH 2.3 citrate buffer satd. aq. sodium bicarbonate and brine. The extracts were dried over Na₂SO₄ and concentrated i. vac. The product was recovered as an oil (used without purification).

The crude alkylated carbazate (1.0 Eq, 1.26 g, 5.7 mmol) was dissolved in dioxane (12 mL) with KOCN (2.0 Eq, 919 mg, 11.4 mmol). Aqueous 2N HCl (2.0 Eq, 5.7 ml, 11.4 mmol) was added. The turbid mixture was stirred ½ Hr at RT and then concentrated i. vac. The paste was dissolved H₂O and EtOAc. The aqueous phase was extracted three times with EtOAC, the extracts dried over Na₂SO₄ and concentrated i. vac. The crude product was purified by chromatography on SiO₂ (40–63μ) eluting with 8:1:1 toluene:EtOAc:iPrOH. The product was obtained as amorphous solid.

Characteristic NMR Resonances; ¹H NMR 400 MHz (CD₃OD); 7.37 (m, 5H), 5.15 (s, 2H), 3.1–3.6 (two very broad signals, α-H's of iBu residue), 1.83 (sept, 1H, J=6.8 Hz), 0.88 ( d, 6H, J=6.2, slightly broadened).

Step 2: Preparation of CBZ-Nva-α-AzaLeu-NH₂

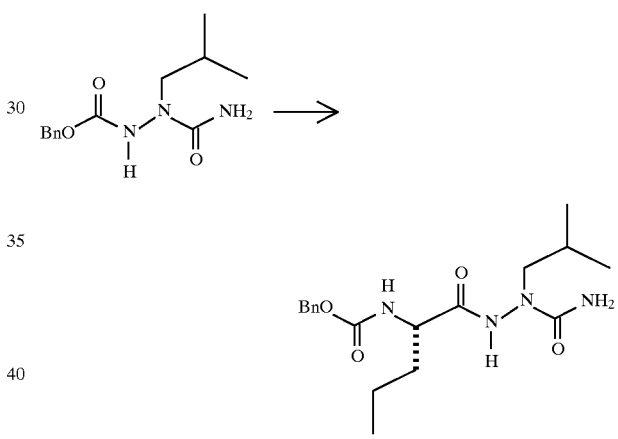

CBZ-α-AzaLeu-NH₂, the product of Step 1, (150 mg, 0.57 mmol) was dissolved CH₃OH with 10% Pd/C (15 mg, 10% by wt). The flask was purged three times vacuum versus H₂ and the mixture stirred at RT 1 Hr. The mixture was filtered through a pad of Celite™ diatomaceous earth and concentrated i. vac. The crude amine from the deprotection was dissolved DMF (2.5 ml) at 0° C. with CBZ-Nva-OH (1.2 Eq, 170 mg, 0.68 mmol) and HOBT hydrate (1.2 Eq, 104 mg, 0.68 mmol). EDC hydrochloride (2.4 Eq, 260 mg, 1.36 mmol) was added and the mixture stirred overnight at 0° C. followed by 1 Hr at RT. The mixture was poured into H₂O and EtOAc and the aqueous phase extracted three times with EtOAc. Combined EtOAc extracts were washed with satd. aq. sodium bicarbonate, washed with brine, dried over Na₂SO₄ and concentrated i. vac. The crude product was purified by chromatography on SiO₂ (40–63μ, 10 g) eluting with 8:1:1 toluene:EtOAc:iPrOH. The product was obtained as amorphous solid. Characteristic NMR Resonances; ¹H NMR 400 MHz (CD₃OD); 7.3 (m's, 5H), 5.07 (s, 2H), 3.94 (t, 1H, J=7.4 Hz), 3.45 (very brd, 1H, α-H of iBu residue), 3.09 (very brd, 1H, α-H of iBu residue), 1.81 (sept, 1H, J=6.9 Hz), 1.67 (Symmetric 9 line m, 2H, J=~6.9 Hz), 1.40 (Symmetric 12 line m, 2H, J=~6.9 Hz), 0.96 (t, 3H, J=7.2 Hz), 0.91 (d, 3H, J=6.6 Hz), 0.90 ( d, 3H, J=6.6 Hz).

Step 3: Preparation of EtOCO-Cha-(ε-BOC)Lys-Nva-α-AzaLeu-NH₂

EXAMPLE 43

EtOCO-Cha-Lys-Nva-α-AzaLeu-NH₂

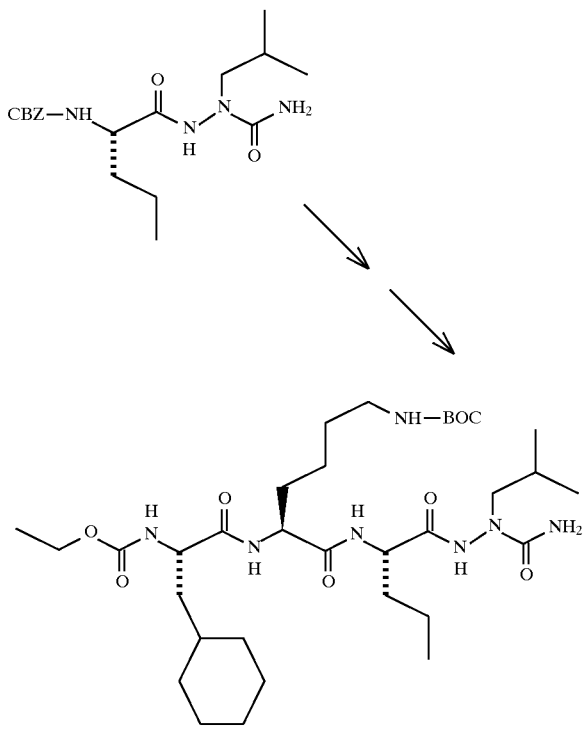

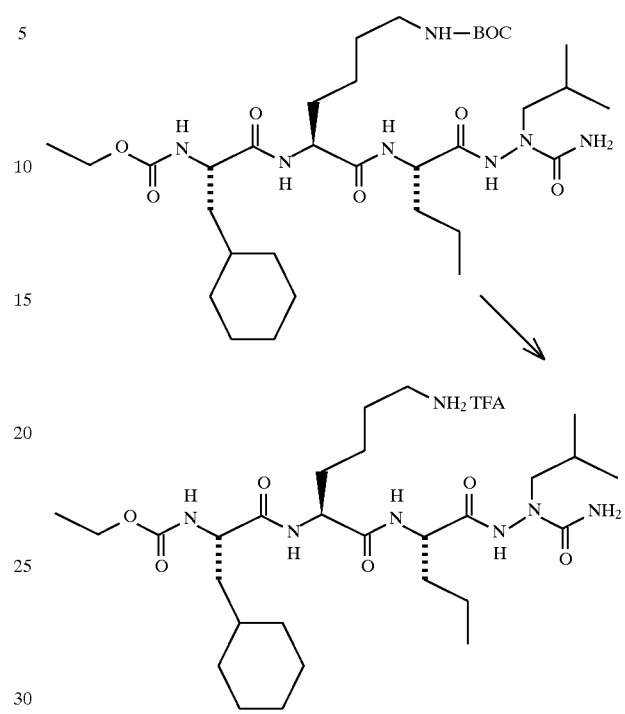

CBZ-Nva-α-AzaLeu-NH₂, the product of Step 2, (51 mg, 0.14 mmol) was deprotected as for Step 2, except for the use of glacial acetic acid as solvent. The crude amine was used in the coupling below.

Characteristic NMR Resonances; ¹H NMR 400 MHz (CD₃OD); 3.69(t, 1H, J=6.7 Hz), 3.47 (brd m, 1H, α-H of iBu residue), 3.1 (brd m, 1H, α-H of iBu residue), 1.95 (s, 3H), 1.7–1.9 (overlapping m's, 3H), 1.42 (sext, 2H, J=7.7 Hz), 0.99 (t, 3H, J=7.3 Hz), 0.924 (d, 3H, J=6.6 Hz), 0.918 (d, 3H, J=6.6 Hz).

The coupling of Nva α-AzaLeu-NH₂ acetate(1.0 Eq, 0.14 mmol) and EtOCO-Cha (ε-BOC)Lys-OH (0.6 Eq, 39.3 mg, 0.083 mmol) was performed as in Step 2 above except for the addition of diisopropylethyl amine (0.9 Eq, 22 μL, 0.125 mmol) to the initial mixture. The product was purified by elution from a Sephadex LH-20-100 column (780×12.7 mm) with methanol. The product was obtained as amorphous solid.

Characteristic NMR Resonances; ¹H NMR 400 MHz (CD₃OD); 4.29 (brd dd, 1H), 4.1 (overlapping m's, 3H), 3.48 (brd m, 1H, α-H of iBu residue), 3.03 (brd m, 1H, α-H of iBu residue), 3.01 (t, 2H, J=6.6 Hz), 1.42 (s, BOC), 1.24 (t, 3H, J=7.1 Hz), 0.96 (t, 3H, J=7.3 Hz), 0.918 (d, 3H, J=6.6 Hz), 0.905 (d, 3H, J=6.6 Hz). Mass spectrum [ESI 80% CH₃CN/0.1% Aq TFA]: m/z 684.3, M+1 for 683.5 calculated mass, m/z 584.3 for loss of BOC residue.

The deprotection of the BOC amine from Example 42 (40 mg, 0.058 mmol) was performed as for Example 9. The crude product was purified by preparatory reverse phase chromatography on an E. Merck LiChroprep RP-18 (310×25 mm) column with 0.1% TFA (aq):CH₃CN (57:43) as eluent. The product was recovered as an amorphous solid.

Characteristic NMR Resonances; ¹H NMR 400 MHz (CD₃OD); 4.37 (q, 1H, J=6.3 Hz), 4.08(overlapping m's, 4H), 3.5 (brd m, 1H, α-H of iBu residue), 3.03 (brd m, 1H, α-H of iBu residue), 2.91 (t, 2H, J=7.5 Hz), 1.23 (t, 3H, J=7.1 Hz), 0.97 (t, 3H, J=7.3 Hz), 0.923 (d, 3H, J=6.6 Hz), 0.909 (d, 3H, J=6.6 Hz). Mass spectrum [ESI 80% CH₃CN/ 0.1% Aq TFA]: m/z 584.3, M+1 for 583.4 calculated mass.

EXAMPLE 44

(α-BOC)-(ε-CBZ)Lys-Nle-α-AzaNle-OEt

Step 1: Preparation of α-AzaNle-OEt

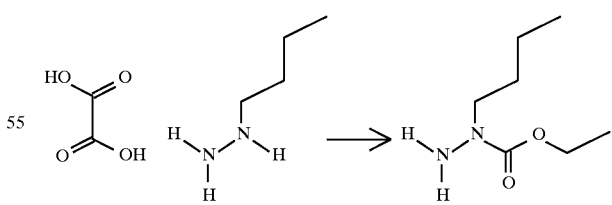

The oxalate salt of n-butylhydrazine (1.0 Eq, 1 g, 5.6 mmol) was suspended in CH₂Cl₂ (15 ml) at RT. Diisopropylethyl amine (3.3 Eq, 3.2 ml, 18.5 mmol) was added and the suspension was cooled to 0° C. Ethyl chloroformate (0.9 Eq, 482 μL, 5.1 mmol) was a dropped in at 0° C. The resulting solution was allowed to warm to RT over ~1 Hr. The mixture was diluted with EtOAC and H₂O. The EtOAc phase was washed with water, washed with brine, dried over Na₂SO₄ and concentrated i. vac. The resulting carbazate is quite clean and was used without purification.

Characteristic NMR Resonances; ¹H NMR 400 MHz (CD₃OD); 4.13 (q, 2H, J=7.1 Hz), 3.39 (t, 2H, J=7.2 Hz), 1.57 (p, 2H, J=7.1 with 2 Hz fine coupling), 1.2–1.4 (overlapping m's, 4H), 0.937 (t, 3H, J=7.3 Hz).

Step 2: Preparation of (α-BOC)-(ε-CBZ)Lys-Nle-α-AzaNle-OEt

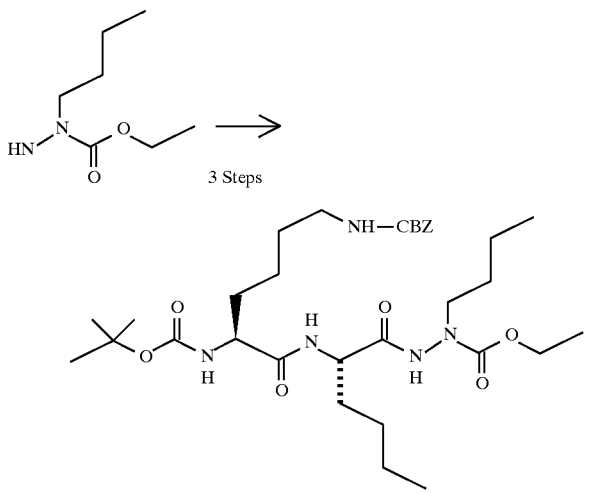

3 Steps

The coupling of the carbazate obtained via the procedures of Step 1 ( 1.5 Eq, 104 mg, 0.65 mmol) and BOC-Nle-OH (1.0 Eq, 100 mg, 0.43 mmol) was performed as in Example 42, Step 2 above. The crude product was purified by chromatography on SiO₂ (40–63μ, 15 g) eluting with 96:4 toluene:tBuOH. The product was obtained as amorphous solid.

Mass spectrum [ESI 80% CH₃CN/0.1% Aq TFA]:m/z 374.1, M+1 for 373.3 calculated mass.

The deprotection of the BOC amine (125 mg) was carried out as described in Example 9. The product was purified by elution from a Sephadex LH-20-100 column (780×12.7 mm) with methanol. The product was obtained as amorphous solid (Product recovery was essentially quantitative.). The NMR spectrum was consistent with the desired product.

The crude amine (1.0 Eq, 20 mg, 0.052 mmol) was dissolved THF (1.25 mL) with commercial (α-BOC)(ε-CBZ)Lysine N-hydroxysuccinimide ester (1.5 Eq, 37 mg, 0.078 mmol) at RT. Diisopropylethyl amine (1.0 Eq, 9 μL, 0.052 mmol) was added and the solution stirred at RT for 1 Hr. The mixture was diluted EtOAc and H₂O and the aqueous phase extracted three times EtOAc. The EtOAc extracts were washed with H₂O, washed with satd. aq. NH₄Cl, dried over Na₂SO₄ and concentrated i. vac. The product was purified by elution from a Sephadex LH-20-100 column (780×12.7 mm) with methanol. The product was obtained as amorphous solid.

Characteristic NMR Resonances; ¹H NMR 400 MHz (CD₃OD); 7.2–7.4 (m's, 5H), 5.06 (s, 2H), 4.32 (brd, 1H), 4.10 (brd, 2H), 3.98 (dd, 1H, J=8.4, 5.4 Hz), 3.44 (brd, 2H), 3.10 (t, 2H, J=6.7 Hz), 1.22 (brd, 3H, OEt methyl), 0.92 (t, 5H, J=7.3 Hz).

EXAMPLE 45

α-[3-Cyclohexylpropyl]-(ε-CBZ)Lys-Nle-α-AzaNle-OEt

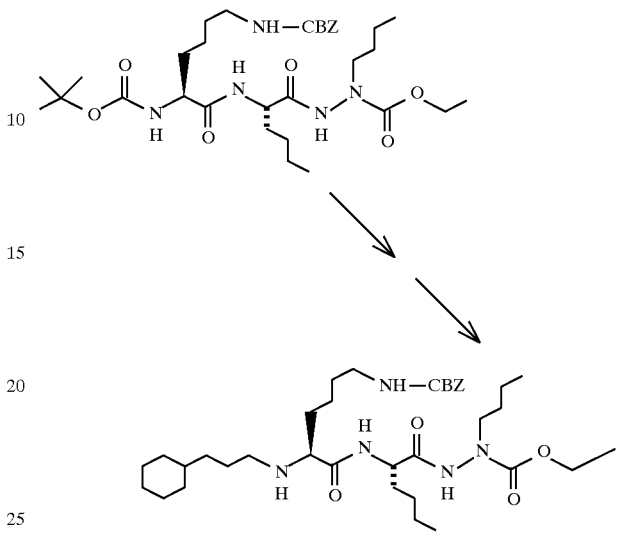

Step 1: Preparation of (ε-CBZ)Lys-Nva-α-AzaNle-OEt

The deprotection of the BOC amine obtained following the procedures of Example 445 (30 mg) was carried out as described in Example 9. The product was purified by elution from a Sephadex LH-20–100 column (780×12.7 mm) with methanol. The product was obtained as amorphous solid.

Step 2: Preparation of α-[3-Cyclohexylpropyl]-(ε-CBZ)Lys-Nle-α-AzaNle-OEt

The reductive alkylation of (ε-CBZ)Lys-Nle-α-AzaNle-OEt (1.0 Eq, 17 mg, 0.026 mmol, product of Step 1) by 3-cyclohexypropionaldehyde (1.0 Eq, 4 μL) was performed as described in Example 37. The crude product was purified by chromatography on SiO₂ (40–63μ, 2g) eluting with 96:4 toluene: tBuOH. The product was obtained as amorphous solid.

Characteristic NMR Resonances; ¹H NMR 400 MHz (CD₃OD); 7.25–7.4 (m, 5H), 5.05 (s, 2H), 4.38 (brd, 1H), 4.11 (brd, 2H), 3.51 (m, 1H, α-H of n-Bu residue), 3.41 (m, 1H, α-H of n-Bu residue), 3.1 (2 overlapping t's, 3H), 2.45 (m, 2H, α-H's of cyclohexylpropyl sidechain.). Mass spectrum [ESI 80% CH₃CN/0.1% Aq TFA]: m/z 660.3, M+1 for 659.5 calculated mass.

EXAMPLE 46

α-[3-Cyclohexylpropyl]-Lys-Nle-α-AzaNle-OEt

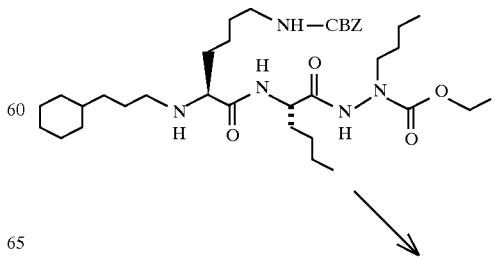

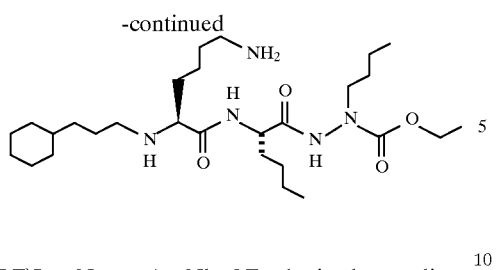

The (ε-CBZ)Lys-Nva-α-AzaNle-OEt obtained according to the procedures of Example 45, Step 1 (6 mg) was deprotected as for Example 42, Step 2 above.

Characteristic NMR Resonances; $^1$H NMR 400 MHz (CD$_3$OD); 4.38 (brd, 1H), 4.12 (brd, 2H), 3.52 (brd m, 1H, α-H of n-Bu residue), 3.4 (brd m, 1H, α-H of n-Bu residue), 3.13 (t, 1H, J=6.8 Hz), 2.76 (t, 2H, J=7.3 Hz), 2.45 (m, 2H, α-H's of cyclohexylpropyl sidechain.), 0.93 (t, 3H, J=7.3 Hz, overlaps m, 2H). Mass spectrum [ESI 80% CH$_3$CN/0.1% Aq TFA]: m/z 526.2, M+1 for 525.4 calculated mass.

EXAMPLE 47

α-[3-Cyclohexylpropyl]-(ε-BOC)Lys-Nva-α-AzaLeu-OEt

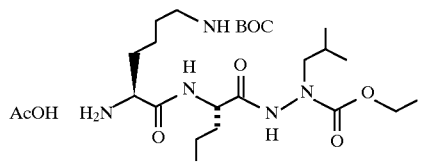

1

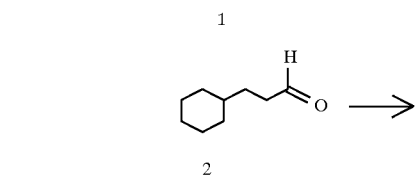

2

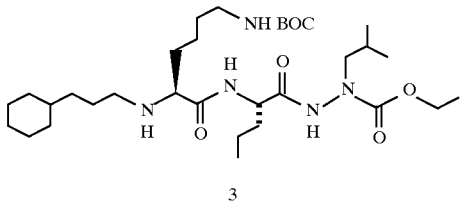

3

The reductive alkylation of (ε-BOC)Lys-Nva-α-AzaLeu-OEt (40.2 mg, 0.075 mmol) with 3-cyclohexylpropionaldehyde (12.0 μL, 0.086 mmol) was performed as for Example 37. The crude product was purified by preparatory reverse phase chromatography on an E. Merck LiChroprep RP-18 (310×25 mm) column with 0.1% TFA (aq):CH$_3$CN (25:75) as eluent. The product was recovered as an amorphous solid.

$^1$H NMR [400 MHz, d4 Methanol] Selected peaks 4.4 (broad s, 1H), 4.12 (broad s, 2H), 3.79 (t, 1H), 2.87 (m, 2H). Mass Spectrum [ESI, 80% CH$_3$CN/20% 0.01% aqTFA] m/z=612.4.

EXAMPLE 48

α-[3-Cyclohexylpropyl]-Lys-Nva-α-AzaLeu-OEt

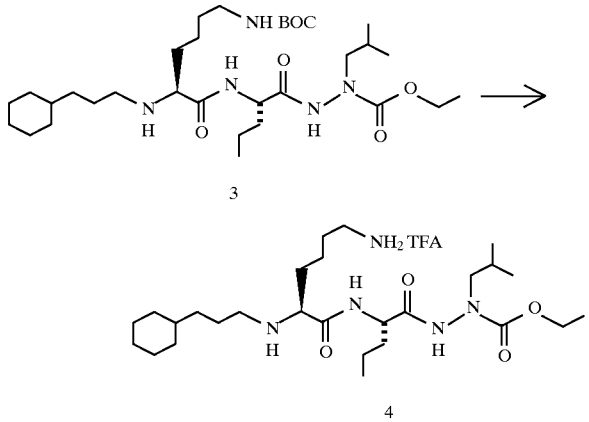

The deprotection of the BOC amine prepared according to the procedures of Example 47 (25.2 mg, 0.041 mmol) was performed as described above for Example 9. The crude product was purified by preparatory reverse phase chromatography on an E. Merck LiChroprep RP-18 (310×25 mm) column with 0.1% TFA (aq):CH$_3$CN (50:50) as eluent. The product was recovered as an amorphous solid. $^1$H NMR [400 MHz, d4 Methanol] Selected peaks 4.2 (broad s, 2H), 3.85 (q, 1H), 2.93 (m, 4H), 1.0 (t, 3H), 0.93 (d, 6H). Mass Spectrum [ESI, 80% CH$_3$CN/20% 0.01% aqTFA] m/z= 512.3.

EXAMPLE 49

α-[3-Cyclohexylpropyl]-(ε-CBZ)Lys-Nva-α-AzaNle-OEt

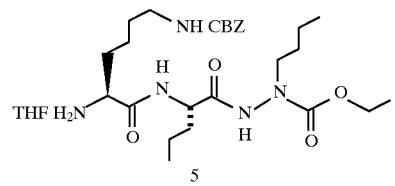

5

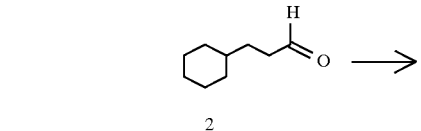

2

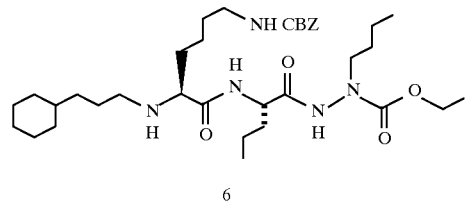

6

The reductive alkylation of the trifluoroacetate salt of (ε-CBZ)Lys-Nva-α-AzaNle-OEt (48.8 mg, 0.077 mmol, obtained from the BOC deprotection of Example 45) with 3-Cyclohexylpropionaldehyde (11.0 μL, 0.072 mmol) was performed as for Example 37 except for the addition of diisopropylethylamine (13 μL, 0.073 mmol) before the addition of glacial acetic acid. The crude product was purified by chromatograph on SiO₂ (40–63μ, 50:1 SiO₂: crude mass ratio) eluting with toluene:isopropyl alcohol (75:25). The product was recovered as an amorphous solid.

¹H-NMR [400 MHz, d4 Methanol] Selected peaks: 4.38 (broad s, 1H), 4.1 (broad s, 1H), 3.51 (m, 1H), 3.39 (m, 1H), 2.4 (t, 2H). Mass Spectrum [ESI, 80% CH₃CN/20% 0.01% aqTFA ] m/z=646.5.

EXAMPLE 50

α-[3-Cyclohexylpropyl]-Lys-Nva-α-AzaNle-OEt

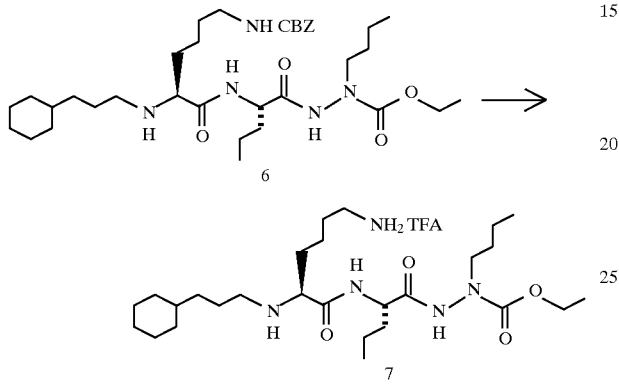

The CBZ protected amine obtained following the procedures of Example 49 (22.0 mg, 0.034 mmol) was dissolved in absolute ethanol (2 mL) with Pd/C 10% (7.0 mg, 30% w/w). The reaction flask was purged three times vacuum versus H₂ and stirred vigorously under one atm. of H₂ at room temperature. The reaction was typically complete after 2.5 hours as judged by TLC. The reaction mixture was filtered through a pad of Celite™ diatomaceous earth to remove the catalyst and concentrated i. vac. The crude product was purified by preparatory reverse phase chromatography on an E. Merck LiChroprep RP-8 (310×25 mm) column with 0.1% TFA (aq):CH₃CN (50:50) as eluent. The product was recovered as an amorphous solid. ¹H NMR [400 MHz, d4 Methanol] Selected peaks: 4.38 (broad s, 1H), 4.12 (broad s, 2H), 3.85 (q, 1H), 2.93 (m, 4H). Mass Spectrum [ESI, 80% CH₃CN/20% 0.01% aqTFA] m/z=512.4.

EXAMPLE 51

α-[1,2,3,4-tetrahydronaphthyl-2-methyl]-(ε-CBZ) Lys-Nva-α-AzaNle-OEt

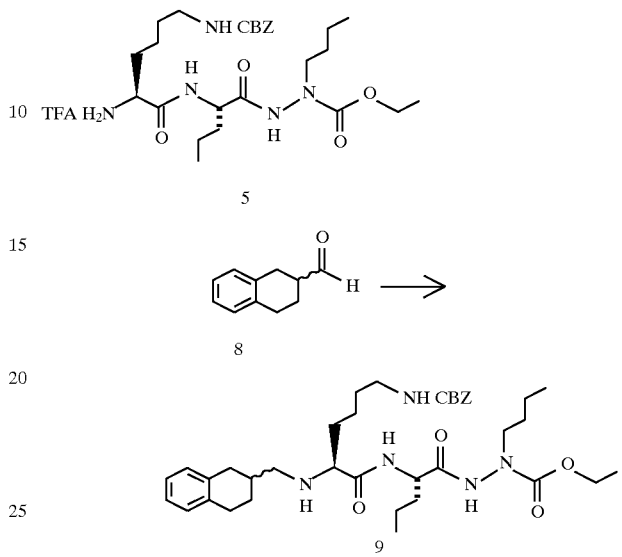

The reductive alkylation of (ε-CBZ)Lys-Nva-α-AzaNle-OEt (33.5 mg, 0.053 mmol, obtained from the BOC deprotection of the product of Example 45) by (±)-1,2,3,4 tetrahydronaphthaldehyde (8.5 μL, 0.048 mmol) was performed as described in Example 38. The product was purified by elution from a Sephadex LH-20-100 column (780×12.7 mm) with methanol. The product was recovered as an amorphous solid. ¹H NMR [400 MHz, d4 Methanol] Selected peaks: 7.32 (m, 5H), 7.02 (m, 4H), 5.05 (s, 2H), 4.39 (broad s, 1H), 4.1 (broad s, 2H), 3.48 (m, 1H), 3.4 (m, 1H). Mass Spectrum [ESI, 80% CH₃CN/20% 0.01% aqTFA] m/z=666.5.

EXAMPLE 52

α-[1,2,3,4-tetrahydronaphthyl-2-methyl]-Lys-Nva-α-AzaNle-OEt

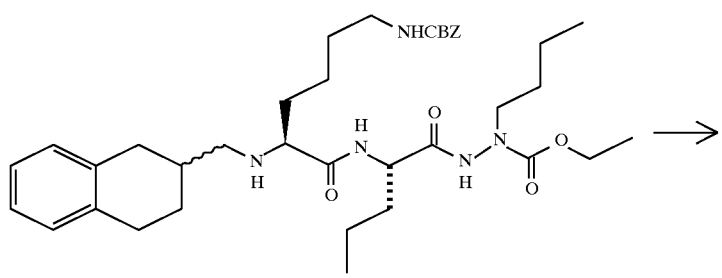

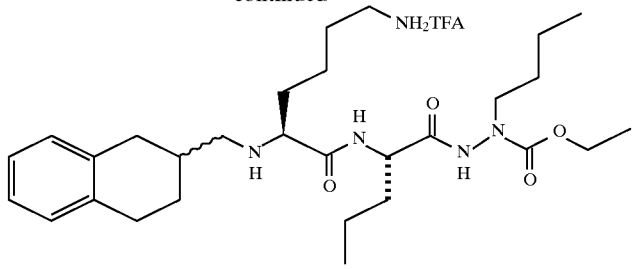

Deprotection of the CBZ amine prepared according to the procedures of Example 51 ( 12.5 mg, 0.016 mmol ) was carried out as described in Example 50. The product was purified by preparatory reverse phase chromatography on an E. Merck LiChroprep RP-8 (310×25 mm) column with 0.1% TFA (aq):CH$_3$CN (40:60) as eluent. The product was recovered as an amorphous solid. $^1$H NMR [400 MHz, d4 Methanol] Selected peaks: 7.07 (s, 4H), 4.34 (broad, 1H), 4.11 (broad s, 2H), 3.89 (q, 1H). Mass Spectrum [ESI, 80% CH$_3$CN/20% 0.01% aqTFA] m/z=532.4.

EXAMPLE 53

N-ethylcarbamoyl-phenylalanine-valine-alanine-leucinol

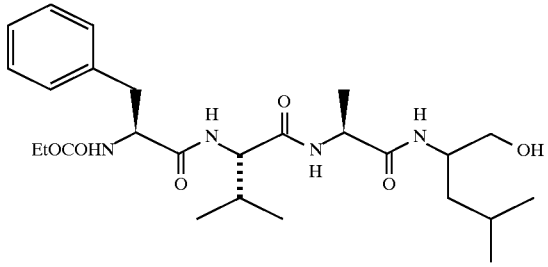

Step 1: Preparation of Val-Ala-Leu-® (Merrifield)

Standard Boc deprotection protocol for resin: Boc-V-A-L-® (Merrifield) (260 mg, Preparation 1) was rinsed with DCM (3×15 mL) and deprotected by treatment with 50% TFA/DCM (25 min). The solution was filtered and the resin was rinsed with DCM (3×15 mL), 10% DIEA/DCM (3×15 mL), and DCM (3×15 mL).

Step 2: Preparation of Boc-Phe-Val-Ala-Leu-® (Merrifield)

Standard manual coupling protocol for Merrifield or PAM resins: The deprotected resin of Step 1 was suspended in DMF (5 mL) and Boc-Phe (119 mg, 0.45 mmol), BOP (310 mg, 0.70 mmol), and HOBt (95 mg, 0.70 mmol) added followed by DIEA (100 µL). The reaction mixture was agitated at room temperature until a negative Kaiser test (See Preparation 6) is obtained (30 min to 24 hours typical). The resin is rinsed with DMF (3×15 mL) then DCM (3×15 mL).

Step 3: Preparation of EtOCO-Phe-Val-Ala-Leu-® (Merrifield)

Standard ethylchloroformate capping procedure for resin: The resin of Step 3 was suspended in DMF (5 mL) and DIEA (100 µL) added followed by ethylchloroformate (55 µL, 0.6 mmol) and the mixture agitated at room temperature (30 min). The resin was rinsed with DMF (3×15 mL), DCM (3×15 mL), and dried.

Step 4: Preparation of N-ethylcarbamoyl-phenylalanine-valine-alanine-leucinol

Standard reductive cleavage protocol: The resin was then transferred to a dry flask and a solution of lithium borohydride (67 mg, 3 mmol) in dry THF (3 mL) was added followed by DIEA (50 µL, 0.3 mmol). The reaction was stirred at room temperature (1–5 hr) under an atmosphere of N$_2$. The reaction was concentrated in vacuo and the resin taken up in water, filtered, and the filtrate lyophilized.

Standard purification protocol: The resulting product was purified by reverse phase high performance liquid chromatography (RP-HPLC) (Waters Delta Pak C$_{18}$, RCM 25×10, 10 mL/min., 20→80% CH$_3$CN gradient, 30 min). The fractions containing the desired product were combined and lyophilized, providing the peptide (5) as a white powder.

Electrospray MS M+H=507.1

EXAMPLE 54

N-ethylcarbamoyl-phenylalanine-valine-norvalanine-leucinol

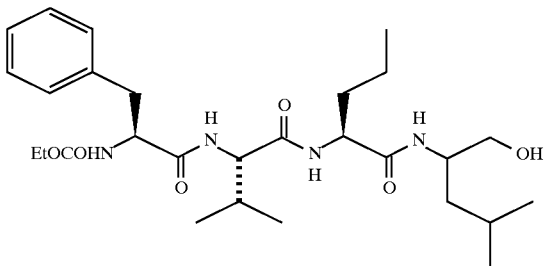

Starting with N-ethylcarbamoyl-phenylalanine-valine-norvalanine-leucine-® Pam resin (80 mg, Preparation 4) the standard reductive cleavage protocol of Example 53, Step 4 was used to provide the crude product which was taken up in water, filtered, and the filtrate lyophilized. The product was purified using the standard purification protocol Example 53, Step 4, providing the desired product as a white powder.

Electrospray MS M+H=535.4

EXAMPLE 55

N-3-cyclohexylpropyl-valine-alanine-leucinol

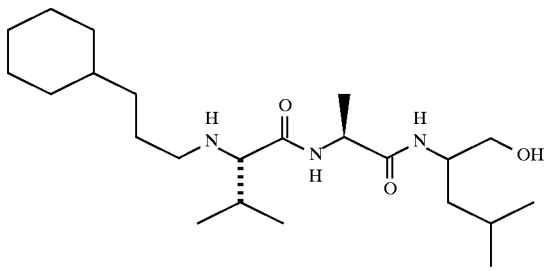

Step 1: Preparation of Val-Ala-Leu-® (Merrifield)

Boc-V-A-L-® (Merrifield) resin (91 mg, Preparation 1) was deprotected by the standard Boc deprotection protocol of Example 53, Step 1.

Step 2: Standard solid phase reductive amination procedure:

The N-deprotected resin was suspended in DMF (2 mL) and cyclohexylpropionaldehyde (9.5 mg, 69 μmol) added. The reaction was agitated briefly (5–15 min. typical reaction time) and sodium cyanoborohydride (4.5 mg, 69 μmol) added in one portion. The reaction was agitated (5–24 hours typical reaction times) and the resin was rinsed with DMF (2×2 mL) and MeOH (2×2 mL). Kaiser test on the resin was negative.

Step 3: Preparation of N-3-cyclohexylpropyl-valine-alanine-leucinol

The product was liberated from the resin using the standard reductive cleavage protocol of Example 53, Step 4, and the resulting product purified by the standard peptide purification protocol of Example 53, Step 4. This afforded the desired material as a white powder.

Electrospray MS M+H=412.4

EXAMPLE 56

N-E -α-methylcinnamyl-valine-alanine-leucinol

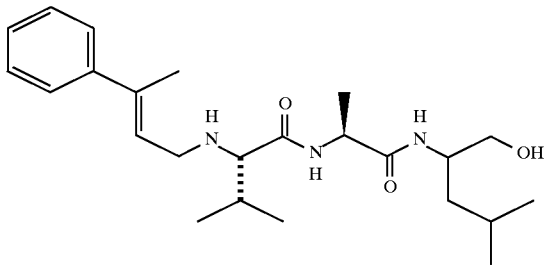

Boc-V-A-L-® (Merrifield) resin (93 mg, Preparation 1) was deprotected by the standard Boc deprotection protocol of Example 53, Step 1 and alkylated by using the standard solid phase reductive amination procedure of Example 55, Step 2 with α-methyl-trans -cinnamaldehyde (8 μL, 55 μmol). The product was liberated from the resin using the standard reductive cleavage protocol of Example 53, Step 4, and the resulting product purified by the standard peptide purification protocol of Example 53, Step 4. This afforded the desired material as a white powder.

Electrospray MS M+H=418.4

EXAMPLE 57

N-ethylcarbamoyl-phenylalanine-valine-alanin-(3', 3'-dimethybutyl) amide

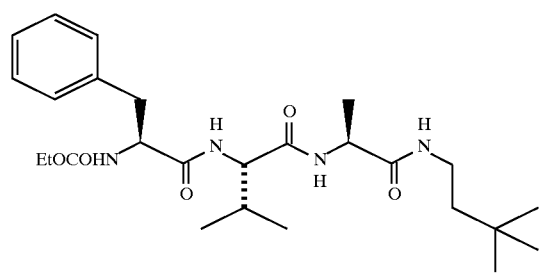

Step 1: Standard resin cleavage procedure for amines:

N-ethylcarbamoyl-phenylalanine-valine-alanine-® Pam resin (180 mg, Preparation 5) was swelled with DMF (200 μL) and 3,3-dimethylbutyl amine (800 μL) was added. The reaction was stirred at RT (4 h to 24 h typical reaction times). The reaction mixture was concentrated in vacuo and taken up into EtOH and the resin filtered off affording a solution of the desired product.

Step 2:

The filtrate, from Step 1, was concentrated in vacuo and recrystallized from EtOH/H$_2$O, filtered, and dried. Further purification was effected by the standard peptide purification protocol of Example 53, Step 4 (20→90% CH$_3$CN gradient, 30 min). This afforded the desired product as a white powder.

Electrospray MS M+H=491.2

EXAMPLE 58

N-ethylcarbamoyl-phenylalanine-valine-alanin-(isoamyl)amide

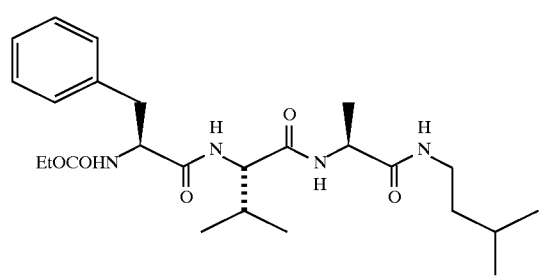

The compound was prepared by the standard resin cleavage procedure for amines of Example 57, Step 1, using isoamyl amine (1.5 mL) and N-ethylcarbamoyl-phenylalanine-valine-alanine-® Pam resin (151 mg, Preparation 5). Purification of the product was effected by using the purification procedure of Example 57, Step 2, affording the product as a white solid.

Electrospray MS M+H=477.2

EXAMPLE 59

N-ethylcarbamoyl-phenylalanine-ornithine-norvaline-leucin-hydrazide

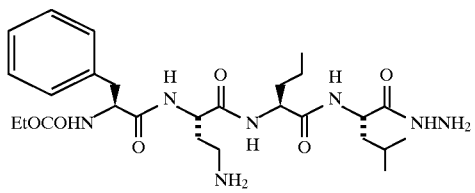

Standard resin cleavage procedure for hydrazine: EtOCO-phenylalanine-arginine (NO2)-norvaline-leucine-® (PAM) resin (156 mg, Preparation 6) was swollen in DCM (1 mL) and anhydrous hydrazine added (2.5 mL). The reaction was stirred at RT (12 to 24 h reaction time) and concentrated in vacuo.

The resin was suspended in hot EtOH/H$_2$O, filtered, and lyophilized. The material was purified using the standard peptide purification procedure of Example 53, Step 4, affording the desired hydrazide as a white powder.

Electrospray MS M+H=578.3

NOTE: Hydrazine cleaves the peptide from the resin (see reference 15 below) and converts the nitroarginine residue to ornithine (see reference 16 below).

15) Ohno, M.; Anfinsen, C. B. *J. Am. Chem. Soc.*, 1967, 89, 5994.

16) See discussion in Bodansky, M. *Peptide Chemistry a Practical Textbook*, Second Edition; Springer Verlag: New York, 1993; p. 98.

EXAMPLE 60

N-ethylcarbamoyl-phenylalanine-valine-alanine-leucin-hydrazide

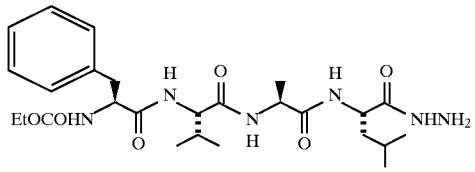

N-ethylcarbamoyl-phenylalanine-valine-alanine-leucine Pam resin (191 mg, Preparation 2) was treated with the standard resin cleavage procedure for hydrazine as described in Example 59. The reaction mixture was concentrated in vacuo and suspended in EtOH and the resin filtered. The filtrate was concentrated in vacuo affording a tan solid which was purified by the standard peptide purification protocol of Example 53, Step 4. This provided the desired hydrazide as a white powder.

Electrospray MS M+H=535.2

EXAMPLE 61

N-ethylcarbamoyl-phenylalanine-valine-leucinhydrazide

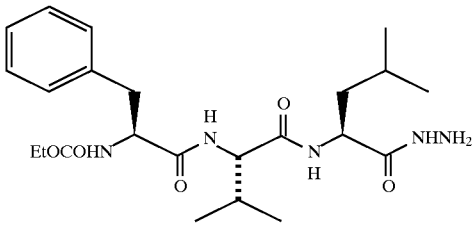

From the synthesis of Example 60, a second component was also isolated during purification and identified as the alanine deletion product.

Electrospray MS M+H=464.2

EXAMPLE 62

N-ethylcarbamoyl-phenylalanine-valine-alaninhydrazide

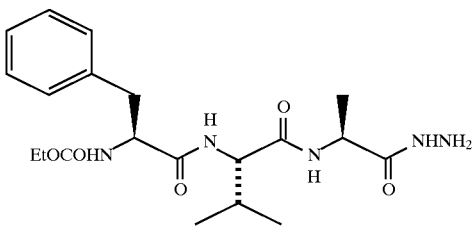

N-ethylcarbamoyl-phenylalanine-valine-alanine-Pam resin (150 mg, Preparation 5) was treated with the standard resin cleavage procedure for hydrazine of Example 59. The reaction mixture was concentrated in vacuo and suspended in EtOH and the resin filtered. The filtrate was concentrated in vacuo affording a tan solid which was purified by the standard peptide purification protocol of Example 53, Step 4. This provided the desired hydrazide as a white powder.

Electrospray MS M+H=422.2

EXAMPLE 63

N-Boc-valine-norvaline-leucinamide

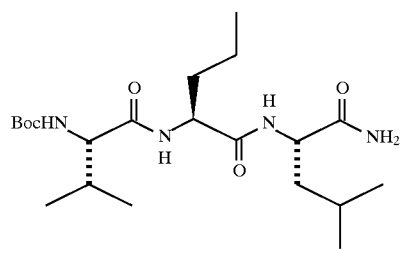

Boc-norvaline (2.0 g, 9.2 mmol) and leucinamide (1.53 g, 9.2 mmol) were dissolved in dry DMF (90 mL). The reaction was cooled to 0° C. and DCC (2.3 g, 11 mmol), HOBt (1.48 g, 11 mmol), and DEA (1.9 mL, 11 mmol) added. The mixture was stirred for 20 min at 0° C. and allowed to slowly warm to room temperature overnight (17 h). The mixture was concentrated to ⅓ its original volume, cooled, and filtered. The filtrate was concentrated, affording a yellow oil which was purified by column chromatography (SiO$_2$, 1:1 hexanes/EtOAc→EtOAc) providing Boc-norvaline-leucinamide as white solid (selected signals 400 MHz, $^1$H NMR, CDCl$_3$: $_\delta$4.93 (m, 1 H), 4.45 (m, 1 H), 3.99 (m, 1 H), 1.81–1.71 (m, 2 H), 1.68-1.50 (m, 4 H), 1.41 (s, 9 H), 1.4–1.3 (m, 2 H), 0.9 (m, 9 H)). The Boc-protecting group was removed by treatment of Boc-norvaline-leucinamide (1.5 g, 4.6 mmol) with 50% TFA/DCM (60 mL) at room temperature (30 min). The reaction mixture was concentrated in vacuo and the peptide triturated with diethyl ether and dried in vacuo overnight providing norvaline-leucinamide as a foamy white solid (Electrospray MS M+H=230.1). Boc-valine (233 mg, 1.1 mmol) and norvaline-leucinamide (246 mg, 1.1 mmol) were dissolved in DMF (5 mL) and the solution cooled to 0° C. DCC (266 mg, 1.3 mmol), HOBt (174 mg, 1.3 mmol), and DIEA (224 μL, 1.3 mmol) were added and the reaction allowed to slowly warm to RT (overnight, 17 h). The reaction was filtered and the filtrate concentrated in vacuo affording a solid which was purified by column chromatography (SiO$_2$, EtOAc). This provided the desired Boc-valine-norvaline-leucinamide as a white solid.

Electrospray MS M+H=429.2

EXAMPLE 64

N-3-cyclohexylpropyl-valine-norvaline-leucinamide

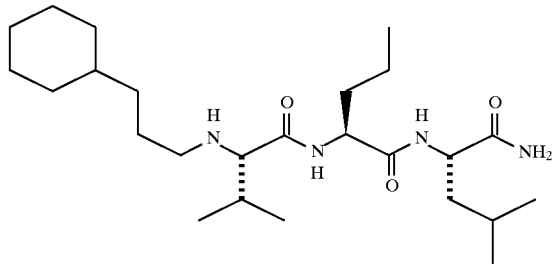

Step 1: Standard solution phase Boc deprotection

Boc-valine-norvaline-leucinamide (21.4 mg, 50 μmol, product of Example 63) was dissolved in 50% TFA/DCM (5.0 mL) and the solution stirred for 30 min. at RT. The solution was concentrated in vacuo affording a white powder that was used directly in the subsequent reaction.

Step 2: Standard solution phase reductive amination procedure

The N-deprotected material was dissolved in MeOH (280 μL) and 3-cyclohexylpropionaldehyde (7.6 μL, 50 μmol) added. The reaction was stirred briefly (1–5 min.) and a solution of sodium cyanoborohydride (3.2 mg, 50 μmol) in MeOH (200 μL) was added. The pH of the reaction mixture was adjusted to 7 by the addition of small aliquots (1 μL) of DIEA and the solution was stirred overnight at RT (5–24 hr). 50% HOAc/MeOH (1 mL) was added to the reaction mixture and the mixture concentrated in vacuo.

Step 3: Purification

The product was purified by the standard peptide purification protocol of Example 53, Step 4, affording the desired material as a white powder.

Electrospray MS M+H=453.4

EXAMPLE 65

N-E -α-methylcinnamyl-valine-alanine-leucinamide

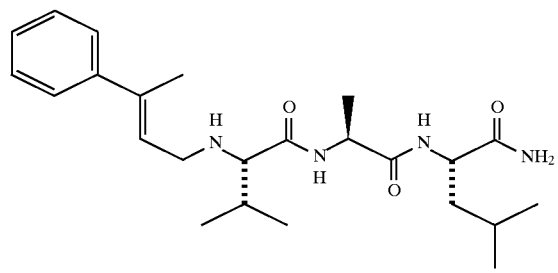

Step 1:
N-9-fluorenylmethoxycarbonyl-valine-alanine-leucine-® Rink Amide MBHA resin (92 mg, Preparation 7) was deprotected using the standard Fmoc deprotection protocol for resin described in Preparation 6. The deprotected resin was then alkylated using the standard solid phase reductive amination procedure of Example 55 with α-methyl-trans-cinnamaldehyde (60 μL, 0.4 mmol).

Step 2: Standard acidic cleavage for Fmoc resin protocol A
The peptide was cleaved from the resin using TFA/H$_2$O (24:1, 2 mL) for 2 hr at RT. The resin was filtered off and the filtrate concentrated in vacuo , taken up into 25% aq. CH$_3$CN, and lyophilized.

Step 3: Purification
The peptide was purified using the standard peptide purification protocol of Example 53, Step 4, affording the desired material as a white powder.

Electrospray MS M+H=431.3

EXAMPLE 66

N-3-phenylpropanoyl-lysine-norvaline-leucinamide

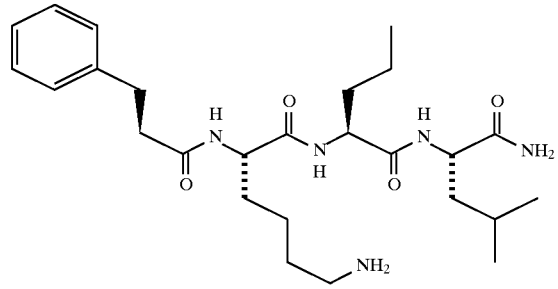

Step 1:
Lysine-norvaline-leucine-Rink Amide MBHA resin (102 mg, Preparation 8) was rinsed with DMF (2×1.5 mL) and suspended in DMF (1.5 mL) and DIEA added (20 μL). 3-phenylpropanoic acid (14 mg, 85 μmol), and PyBOP (44.1 mg, 85 μmol) was added. The reaction was agitated at RT (1–18 h typical reaction time) and the resin filtered and rinsed with MeOH (3×1.5 mL).

Step 2: Standard acidic cleavage for Fmoc resin protocol B
The peptide was cleaved from the resin by treatment with TFA/anisole/water (98:1:1) (3 mL) for 3 h at RT. The resin was filtered off and the filtrate concentrated in vacuo, taken up into 25% aq. CH$_3$CN, and lyophilized.

Step 3: Purification
The product was purified using the standard peptide purification protocol of Example 53, Step 4 with a 25–55% aq. CH$_3$CN gradient over 30 min. This afforded the desired material as a white powder.

Electrospray MS M+H=490.1

EXAMPLE 67

N-3-cyclohexylpropanoyl-lysine-norvaline-leucinamide

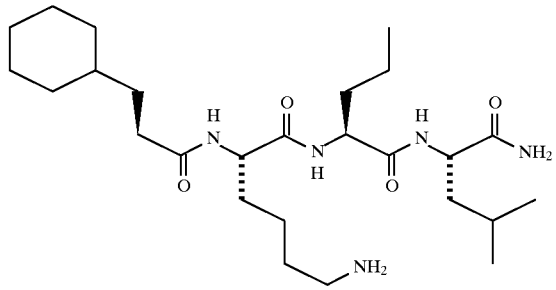

Lysine-norvaline-leucine-Rink Amide MBHA resin (108 mg, Preparation 8) was rinsed with DMF (2×1.5 mL) and suspended in DMF (1.5 mL) and DIEA added (20 μL). 3-cyclohexylpropanoic acid (14 mg, 90 μmol), and PyBOP (47 mg, 90 μmol) was added. The reaction was agitated at RT (1–18 h typical reaction time) and the resin filtered and rinsed with MeOH (3×1.5 mL). The peptide was removed from the resin using the standard acidic cleavage for Fmoc resin protocol B of Example 66, Step 2, and purified by the standard peptide purification protocol of Example 53, Step 4. This afforded the desired material as a white powder.

Electrospray MS M+H=496.2

EXAMPLE 68

Oral Composition

As a specific embodiment of an oral composition of a compound of this invention, 5 mg of a compound of structural formula I is formulated with sufficient finely divided lactose to provide a total amount of 580 to 590 mg to fill a size 0 hard gelatin capsule.

RESIN PREPARATIONS 1–8

All reactions were carried out under an atmosphere of nitrogen unless otherwise noted.

PREPARATION 1

N-tertbutyloxycarbonyl-valine-alanine-leucine-Merrifield resin

Boc-V-A-L-® (Merrifield resin): 1 mmol of Boc-Leu-® (Merrifield) resin (Bachem Calif., 0.6 mmol/g) was swelled in DCM in a fritted vessel equipped for manual peptide synthesis. Nitrogen sparging was used as a source of agitation. The Ala and Val residues were coupled to the resin using standard Boc-amino acid coupling protocol (see reference 11 below) with DCC activation and DCM as the reaction solvent. DIEA was used for all neutralizations. Following synthesis, the resin-bound tripeptide was rinsed with DCM (2×20 mL), MeOH (2×20 mL), DCM (2×20 mL), and dried ($N_2$ stream) affording the loaded resin.

11) Standard Boc-amino acid coupling procedures, for example, can be found in Stewart, J. M.; and Young, J. D. *Solid Phase Peptide Synthesis*, Second Edition; Pierce Chemical Company: Rockford, Ill. 1984; pp. 91–95.

PREPARATION 2

N-tertbutyloxycarbonyl-valine-alanine-leucine-Pam resin

Boc-V-A-L-® (PAM resin): The resin-bound tripeptide was prepared from 1.5 mmol of Boc-Leu-® (PAM) resin (Bachem Calif., 0.6 mmol/g), using the synthesis protocol outlined in Preparation 1. NMP was used as the reaction solvent in place of DCM.

PREPARATION 3

N-ethylcarbamoyl-phenylalanine-valine-alanine-leucine-Pam resin EtOCO-F-V-A-L-® (PAM resin): The resin-bound tripeptide was prepared from 1.0 mmol of Boc-Leu-® (PAM) resin (NovaBiochem, 0.56 mmol/g), using the synthesis protocol outlined in Preparation 1. NMP was used as the reaction solvent in place of DCM. The N-terminal Boc protecting group was removed by treatment with 50% TFA/DCM (30 min., RT) and the tripeptide was capped by the addition of ethylchloroformate (382 μL, 4.0 mmol). The resin was finally rinsed with NMP (3×20 mL), then DCM (3×20 mL), and dried affording the loaded resin.

PREPARATION 4

N-ethylcarbamoyl-phenylalanine-valine-norvalanine-leucine-Pam resin

EtOCO-F-V-Nva-L-® (PAM resin): The resin-bound tripeptide was prepared from 1.0 mmol of Boc-Leu-® (PAM) resin (Bachem Calif., 0.6 mmol/g), using the synthesis procedure outlined in Preparation 3.

PREPARATION 5

N-ethylcarbamoyl-phenylalanine-valine-alanine-Pam resin

EtOCO-F-V-A-® (PAM resin): The resin-bound tripeptide was prepared from 1.0 mmol of Boc-Ala-® (PAM) resin (Bachem Calif., 0.76 mmol/g), using the synthesis procedure outlined in Preparation 3.

PREPARATION 6

N-ethylcarbamoyl-phenylalanine-arginine($NO_2$)-norvaline-leucine-Pam resin 6

EtOCO-F-R($NO_2$)-Nva-L-® (PAM resin): The resin-bound tetrapeptide was prepared from 1.0 mmol of Boc-Leu-® (PAM) resin (Bachem Calif., 0.6 mmol/g), using the synthesis procedure outlined in Preparation 3. The Arg($NO_2$) residue was introduced as the N-Fmoc-protected amino acid using the standard Fmoc-amino acid coupling protocol illustrated below.

Standard Fmoc-amino acid coupling protocol: The resin bound, deprotected dipeptide (422 mg, Nva-Leu-® PAM) was suspended in DMF (10 mL) and Fmoc-Arg($NO_2$) (333 mg, 0.76 mmol), BOP (672 mg, 1.5 mmol), HOBt (206 mg, 1.5 mmol), and DEIA (132 μL, 0.76 mmol) added. The reaction was agitated at RT (1 to 24 h typical reaction time). The resin was filtered and rinsed with DMF (3×15 mL) and DCM (3×15 mL).

Kaiser test (reference 12 below) on the resin was positive, therefore the standard Fmoc-amino acid coupling procedure was repeated using Fmoc-Arg($NO_2$).

Standard Fmoc deprotection protocol for resin: The resin was suspended in 20% piperidine/DMF (10 mL) and agitated at room temperature (10 to 60 min typical reaction time). The resin was filtered and rinsed with DMF (5×15 mL) and DCM (3×15 mL). A Kaiser test on the resin was positive for the presence of a free amino group.

12) Kaiser, E.; Colescott, R. L.; Bossinger, C. D.; Cook, P. I. *Analytical Biochem.*, 1970, 34, 595.

PREPARATION 7

N-9-fluorenylmethoxycarbonyl-valine-alanine-leucine-Rink Amide MBHA resin

Fmoc-V-A-L-® (Rink amide MBHA resin): 1.5 mmol of Rink amide MBHA resin (NovaBiochem, 0.47 mmol/g) was swelled in DMF in a fritted vessel equipped for manual peptide synthesis. Nitrogen sparging was used as a source of agitation. The resin was deprotected using the standard Fmoc deprotection protocol for resin described in Preparation 6, and the Leu, Ala, and Val residues sequentially coupled to the resin using standard Fmoc-amino acid coupling protocol (see reference 13 below). DCC activation was used with DMF as the reaction solvent. Following the synthesis of the resin-bound tripeptide, the material was rinsed with DMF (2×20 mL), DCM (2×20 mL), MeOH (2×20 mL), and dried ($N_2$ stream) affording the loaded resin.

13) Standard Fmoc-amino acid coupling procedures, for example, can be found in Stewart, J. M.; and Young, J. D. *Solid Phase Peptide Synthesis*, Second Edition; Pierce Chemical Company: Rockford, Ill., 1984; pp. 82–95.

PREPARATION 8 lysine-norvaline-leucine-Rink Amide MBHA resin

K-Nva-L-® (Rink amide MBHA resin): The resin was prepared on an ABI 431 A peptide synthesizer (Applied Biosystems, Inc.) using the standard scale ABI 431 A Fmoc peptide synthesis protocol (reference 14 below) on a 0.25 mmol scale starting with unloaded Rink amide MBHA resin (0.47 mmol/g).

14) For the standard ABI 431A Fmoc peptide synthesis protocol refer to the user manual for the ABI 431 A instrument (ABI part 900658, version 1.0A) sections 2 through 7.

Biological Assays

Binding and Inhibition Assays

For direct binding assays, optimal concentrations of affinity purified DR1Dw1 (1.25 nM) or DR4Dw4 (10 nM) are incubated with serial dilutions of biotinylated rat myelin basic protein (RMBP) 90–102 in PBS (phosphate buffered saline) containing 0.75% octyl glucoside, pH 6.5, in 96-well polypropylene plates for 16 to 20 h at 37° C. In studies optimizing the assay it was determined that only between 5 to 10% of the DR molecules are capable of binding added peptide. Therefore, the effective concentration of DR1Dw1 and DR4Dw4 was approximately 0.125 and 1.0 nM, respectively. The conditions of the assays are shown to be in ligand excess, because twofold reduction of these class II concentrations does not change the measured $ED_{50}$ values. The DR-peptide complexes (50 μL) are transferred to wells of a 96-well EIA plate precoated with LB3.1, the monoclonal antibody which recognizes the DR alleles of MHC Class II, and blocked with PBS with fetal calf serum (FCS). An additional 50 μL of 50 mM Tris, pH 7.0, containing 0.75% octyl glucoside is added to each well and the mixture incubated overnight at 4° C. Excess peptide is removed by washing with PBS containing 0.05% Tween 20 (Polyoxyethylene sorbitan monolaurate) and 0.01% $NaN_3$. Europium-labeled streptavidin (Wallac Inc.) is added and incubated overnight. After washing, complexes are measured by the addition of Enhance™ buffer, the tradename for 0.1M acetate phthalate buffer, pH 3.2, containing 0.1% Triton X-100, tradename for polyoxyethylene ethers and other surface active compounds of Union Carbide Chemicals and Plastics Co., Inc. (particularly, a non-ionic surfactant for recovery of membrane components under non-denaturing conditions) 15 μM 2-naphthoyltrifluoroacetone, and 50 μM tri-N-octylphosphine oxide, which buffer releases the chelated europium from streptavidin and forms a highly fluorescent micellar solution. The resultant fluorescence is measured using a fluorescent plate reader (e.g., DELPHIA, Wallac, Inc.). The data are analyzed using a four-parameter logistical curve tilt program (e.g., SigmaPlot) that calculates the concentration of biotinylated peptide giving a half-maximal signal ($ED_{50}$).

The ability of LB3.1 to bind DR1Dw1 and DR4Dw4 is shown to be equivalent by measuring the capacity of Ab-coated plates to bind serial dilutions of biotinylated DR molecules. Europium streptavidin is used to measure the number of DR molecules bound as described for the peptide binding assay.

The effects of pH on HLA-DR binding of RMBP 90–102 are explored by performing assays over a range from 4.0 to 9.0. The equivalently low $ED_{50}$ values are observed between pH 5.0 and 6.5, consistent with previous reports. Both lower $IC_{50}$ values and higher percentage occupancy are observed when octyl glucoside was used compared with Tween 20, dodecyl-β-D-maltoside, NP-40, CHAPS, octanoyl-N-methyl-glucamide, and Triton X-100.

The inhibition assay format is identical to the procedure described above with the exception that the unlabeled antagonist is serially diluted and incubated with constant concentrations of biotinylated RMBP 90–102 (0.3 nM for DR1Dw1 or 0.9 nM for DR4Dw4) and the MHC class II proteins. The concentration of unlabeled compound that prevents 50% of the labeled peptide from binding is the $IC_{50}$ value. The concentration of the biotinylated RMBP 90–102 in each assay is experimentally determined to be at least one-sixth of its measured $ED_{50}$ to assure the inhibition was primarily measuring the binding characteristics of the competitor. This was confirmed by demonstrating that a two-or four fold reduction in the biotinylated agonist peptide did not alter the $IC_{50}$ values obtained with unlabeled competitor proving that the receptor concentration was not limiting.

In particular, a protocol for carrying out the inhibition assay is given below.

Preparation of antibody plate:

Day 1)

Add 115 μL of 5μg/mL LB3.1 in 50 mM Tris HCl pH 9.6/azide to each well of a Costar EIA plate. Incubate the plate overnight at 4° C.

Day 2)

Wash the plate 4 times with water/0.05% Tween-20/azide. Add 200 μL of PBS /5% FCS/azide for 1 hour at 4° C. to block the plate. The plate may be held at this point for later use or used immediately.

Flip out the block. It is not necessary to wash the plate. At 50 μL of load buffer (50 mM Tris HCl, pH 8.0 0.75% octylglucoside). Add to this volume 50 μL of the reaction mix from day 2, step 3 below.

Preparation of reaction mixture

Day 2)

(1) Add the following to a polypropylene round bottom 96-well plate such as a Costar #3794:

(A) Diluent (Ca Mg free PBS adjusted to pH 6.5 with 0.1 M $KH_2PO4$/0.75% octylglucoside/azide).81 μL (B) Competitor at 16.6 times the final concentration in diluent or diluent alone. 9 μL (C) biotinylated rat myelin basic protein (BRMBP) 90–102; 1.5 nM for DR1 or 4.5 nM for DR4 (These are 5× stocks of final concentrations of 0.3 nM/DR1 or 0.9 nM/DR4) 30 μL (D) 6.25 nM DR1Dw1 or 50 nM DR4Dw4 (these are Drosophila transmembrane DR) (This is a 5× stock of the final concentration of 1.25 or 10 nM.) 30 μL Add the DR last and mix well at this time 150 μL (2) Incubate at 37° C. for 20 min and 5 hours.

(3) Add 50 μL of this reaction mixture to one well of the blocked antibody plate from day 2 above.

(4) Incubate overnight at 4° C. to capture the DR-peptide complexes.

(5) Wash 4× with $H_2O$/ 0.05% Tween-20/azide (6) Add 125 μL of 100 ng/mL europium streptavidin (Wallac Inc.) in Ca Mg free PBS with 3.5 mg DTPA, 1.6 mL of 30% BSA/500 mL to each well.

(7) Incubate 2 to 4 hours at 4° C.

(8) Wash 4 times.

(9) Add 125 μL of Enhance™ buffer (described above) and incubate at room temperature.

(10) Read the plates.

Representative of $IC_5$ values for inhibition of peptide binding to DR1 compounds of the present invention are shown in the following Table:

| Example | $IC_{50}/\mu M$ @ 20' | $IC_{50}/\mu M$ @ 5h |
|---|---|---|
| 48 | 0.15 | 0.68 |
| 50 | 0.046 | 0.26 |
| 52 | 0.030 | 0.14 |
| 5 | 0.21 | 1.43 |
| 34 | 0.16 | 1.25 |
| 13 | 0.25 | 1.7 |
| 22 | 0.012 | 1.08 |
| 36 | 0.040 | 0.187 |
| 38 | 0.16 | 1.8 |
| 40 | 0.0052 | 0.059 |
| 2 | 0.26 | 1.59 |

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended,therefore that the invention be defined by the scope of the claims which follow and that such claims be interpreted as broadly as is reasonable.

What is claimed is:

1. A compound selected from:

(1) N-α-((3-Cyclohexyl)propyl))-pyAla-Nva-Leu-NH$_2$, (2) N-α-((2-Methyl-2-((3-cyclohexyl)propylamino))-propanoyl)-Nva-Leu-NH$_2$, (3) N-α-((2-Methyl-2-((3-cyclohexyl)propylamino))-4-pentenoyl)-Nva-Leu-NH$_2$, (4) N-α-((2-Methyl-2-((3-cyclohexyl)propylamino))-4-pentanoyl)-Nva-Leu-NH$_2$, (5) N-α-((3-Cyclohexyl)propyl))-pyAla-Nva-cLys, (6) N-α-((3-Cyclohexyl)propyl))-Nva-Nva-Leu-NH$_2$, (7) N-α-Ethylcarbamoyl-Cha-Val-Nva-NH-NH$_2$, (8) (α-CBZ)-(ε-BOC)Lys-Nva-Leu-NH$_2$, (9) (α-CBZ)-Lys-Nva-Leu-NH$_2$,

(10) α-[Cinnamoyl]-(ε-BOC)Lys-Nva-Leu-NH$_2$,

(11) α-[Cinnamoyl]-Lys-Nva-Leu-NH$_2$,

(12) α-[2-methylcinnamoyl]-(ε-BOC)Lys-Nva-Leu-NH$_2$,

(13) α-[2-methylcinnamoyl]-Lys-Nva-Leu-NH$_2$,

(14) α-[3-methylcinnamoyl]-(ε-BOC)Lys-Nva-Leu-NH$_2$,

(15) α-[3-methylcinnamoyl]-Lys-Nva-Leu-NH$_2$,

(16) α-[2-Phenylcyclopropyl-1-carbonyl]-(ε-BOC)Lys-Nva-Leu-NH$_2$,

(17) α-[2-Phenylcyclopropyl-1-carbonyl]-Lys-Nva-Leu-NH$_2$,

(18) α-[2-Benzylcyclopropyl-1-carbonyl]-(ε-BOC)Lys-Nva-Leu-NH$_2$,

(19) α-[2-Benzylcyclopropyl-1-carbonyl]-Lys-Nva-Leu-NH$_2$,

(20) α-[1-phenylcyclopropyl-1-carbonyl]-(ε-BOC)Lys-Nva-Leu-NH$_2$,

(21) α-[1-Phenylcyclopropyl-1-carbonyl]-Lys-Nva-Leu-NH$_2$,

(22) α-[(1R,2S)-Cyclohexylcyclopropyl-1-carbonyl]-Lys-Nva-Leu-NH$_2$,

(23) α-[Benzylurea]-(ε-CBZ)Lys-Nva-Leu-NH$_2$,

(24) α-[Benzylurea]-Lys-Nva-Leu-NH$_2$,

(25) α-[2-methyl-3-phenylpropionyl]-(ε-CBZ)Lys Nva-Leu-NH$_2$,

(26) α-[2-methyl-3-phenylpropionyl]-Lys-Nva-Leu-NH$_2$

(27) α-[2-(t-Butylsulfony)methyl-3-phenylpropionyl]-(ε-BOC)Lys-Nva-Leu-NH$_2$,

(28) α-[2-(t-Butylsulfony)methyl-3-phenylpropionyl]-Lys-Nva-Leu-NH$_2$,

(29) α-[2,2-dimethyl-3-phenylpropionyl]-(ε-BOC)Lys-Nva-Leu-NH$_2$,

(30) α-[2,2-dimethyl-3-phenylpropionyl]-Lys-Nva-Leu-NH$_2$,

(31) α-[3S-methyl-3-phenylpropionyl]-(ε-CBZ)Lys-Nva-Leu-NH$_2$,

(32) α-[3S-methyl-3-phenylpropionyl]-Lys-Nva-Leu-NH$_2$,

(33) α-[3R-methyl-3-phenylpropionyl]-(ε-BOC)Lys-Nva-Leu-NH$_2$,

(34) α-[3R-methyl-3-phenylpropionyl]-Lys-Nva-Leu-NH$_2$,

(35) α-[3R-methyl-3-cyclohexylpropionyl]-(ε-BOC)Lys-Nva-Leu-NH$_2$,

(36) α-[3R-methyl-3-cyclohexylpropionyl]-Lys-Nva-Leu-NH$_2$,

(37) α-[(1R,2S)-2-Cyclohexylcyclopropyl-1-carbonyl]-Lys-Nva-Leu-NH$_2$,

(38) α(3-Phenylpropyl)-(ε-BOC)Lys-Nva-Leu-NH$_2$,

(39) α-[3-Phenylpropyl]-Lys-Nva-Leu-NH$_2$,

(40) α-[3-Cyclohexylpropyl]-(ε-BOC)Lys-Nva-Leu-NH$_2$,

(41) α-[3-Cyclohexylpropyl]-Lys-Nva-Leu-NH$_2$,

(42) α-[trans-2-Cyclohexylcyclopropyl-1-methyl]-Lys-Nva-Leu-NH$_2$,

(43) EtOCO-Cha-(ε-BOC)Lys-Nva-αAzaLeu-NH$_2$,

(44) EtOCO-Cha-Lys-Nva-α-AzaLeu-NH$_2$,

(45) (α-BOC)-(ε-CBZ)Lys-Nle-αAzaNle-OEt,

(46) α-[3-Cyclohexylpropyl]-(ε-CBZ)Lys-Nle-αAzaNle-OEt,

(47) α-[3-Cyclohexylpropyl]-Lys-Nle-αAzaNle-OEt,

(48) α-[3-Cyclohexylpropyl]-(ε-BOC)Lys-Nva-α-AzaLeu-OEt,

(49) α-[3-Cyclohexylpropyl]-Lys-Nva-αAzaLeu-OEt,

(50) α-[3-Cyclohexylpropyl]-(ε-CBZ)Lys-Nva-αAzaNle-OEt,

(51) α-[3-Cyclohexylpropyl]-Lys-Nva-αAzaNle-OEt,
(52) α-[1,2,3,4-tetrahydronaphthyl-2-methyl]-(ε-CBZ) Lys-Nva-α-AzaNle-OEt,
(53) α-[1,2,3,4-tetrahydronaphthyl-2-methyl]-Lys-Nva-α-AzaNle-OEt,
(54) N-ethylcarbamoyl-phenylalanine-valine-alanine-leucinol,
(55) N-ethylcarbamoyl-phenylalanine-valine-norvalanine-leucinol,
(56) N-3-cyclohexylpropyl-valine-alanine-leucinol,
(57) N-E -α-methylcinnamyl-valine-alanine-leucinol,
(58) N-ethylcarbamoyl-phenylalanine-valine-alanin-(3',3'-dimethylbutyl)amide,
(59) N-ethylcarbamoyl-phenylalanine-valine-alanin-(isoamyl)amide,
(60) N-ethylcarbamoyl-phenylalanine-ornithine-norvaline-leucin- hydrazide,
(61) N-ethylcarbamoyl-phenylalanine-valine-alanine-leucin-hydrazide,
(62) N-ethylcarbamoyl-phenylalanine-valine-leucinhydrazide,
(63) N-ethylcarbamoyl-phenylalanine-valine-alaninhydrazide,
(64) N-Boc-valine-norvaline-leucinamide,
(65) N-3-cyclohexylpropyl-valine-norvaline-leucinamide,
(66) N-E -(-methylcinnamyl-valine-alanine-leucinamide,
(67) N-3-phenylpropanoyl-lysine-norvaline-leucinamide, and
(68) N-3-cyclohexylpropanoyl-lysine-norvaline-leucinamide, or a pharmaceutically acceptable salt thereof.

2. The compound of claim 1 selected from:
(1) N-α((3-Cyclohexyl)propyl))-pyAla-Nva-Leu-NH$_2$,
(2) N-ox-((2-Methyl-2-((3-cyclohexyl)propylamino))-propanoyl)-Nva- Leu-NH$_2$,
(3) N-α((2-Methyl-2-((3-cyclohexyl)propylamino))-4-pentanoyl)-Nva- Leu-NH$_2$,
(4) N-α-((2-Methyl-2-((3-cyclohexyl)propylamino))-4-pentanoyl)-Nva- Leu-NH$_2$,
(5) N-α-((3-Cyclohexyl)propyl))-pyAla-Nva-cLys,
(6) N-oa-((3-Cyclohexyl)propyl))-Nva-Nva-Leu-NH$_2$,
(7) (αCBZ)-Lys-Nva-Leu-NH$_2$,
(8) α[Cinnamoyl]-Lys-Nva-Leu-NH$_2$,
(9) α[2-methylcinnamoyl]-Lys-Nva-Leu-NH$_2$,
(10) α[3-methylcinnamoyl]-Lys-Nva-Leu-NH$_2$,
(11) α[2-Phenylcyclopropyl-1 -carbonyl] -Lys-Nva-Leu-NH$_2$,
(12) α[2-Benzylcyclopropyl-I-carbonyl]-Lys-Nva-Leu-NH$_2$,
(13) o:-[ 1 -Phenylcyclopropyl-I-carbonyl]-Lys-Nva-Leu-NH$_2$
(14) o-[( 1 R,2S)-2-Cyclohexylcyclopropyl-1 -carbonyl ] -Lys-Nva-Leu- NH$_2$,
(15) α-[Benzylurea]-Lys-Nva-Leu-NH$_2$,
(16) α-[2-methyl-3-phenylpropionyl]-Lys-Nva-Leu-NH$_2$,
(17) α-[2-(t-Butylsulfony)methyl-3-phenylpropionyl]-Lys-Nva-Leu-NH$_2$,
(18) α-[2,2-dimethyl-3-phenylpropionyl]-Lys-Nva-Leu-NH$_2$,
(19) α-[3S-methyl-3-phenylpropionyl]-Lys-Nva-Leu-NH$_2$,
(20) α-[3R-methyl-3-phenylpropionyl]-Lys-Nva-Leu-NH$_2$,
(21) α-[3R-methyl-3-cyclohexylpropionyl]-Lys-Nva-Leu-NH$_2$,
(22) α-[3-Phenylpropyl]-Lys-Nva-Leu-NH$_2$,
(23) α-[3-Cyclohexylpropyl]-Lys-Nva-Leu-NH$_2$,
(24) α-[trans-2-Cyclohexylcyclopropyl-1-methyl]-Lys-Nva-Leu -NH$_2$,
(25) EtOCO-Cha-Lys-Nva-αAzaLeu-NH$_2$,
(26) α-[3-Cyclohexylpropyl]-Lys-Nle-α-AzaNle-OEt,
(27) α-[3-Cyclohexylpropyl]-Lys-Nva-α-AzaLeu-OEt,
(28) α-[3-Cyclohexylpropyl]-Lys-Nva-α-AzaNle-OEt,
(29) α-[1,2,3,4-tetrahydronaphthyl-2-methyl]-Lys-Nva-α-AzaNle-OEt,
(30) N-ethylcarbamoyl-phenylalanine-valine-norvalanine-leucinol,
(31) N-ethylcarbamoyl-phenylalanine-ornithine-norvaline-leucin-hydrazide,
(32) N-ethylcarbamoyl-phenylalanine-valine-alanine-leucin-hydrazide, and
(33) N-3-cyclohexylpropanoyl-lysine-norvaline-leucinamide, or a pharmaceutically acceptable salt thereof.

3. The compound of claim 2 selected from:
(1) N-α-((3-Cyclohexyl)propyl))-pyAla-Nva-cLys,
(2) α-[3-Cyclohexylpropyl]-Lys-Nle-α-AzaNle-OEt,
(3) α-[3-Cyclohexylpropyl]-Lys-Nva-α-AzaLeu-OEt,
(4) α-[3-Cyclohexylpropyl]-Lys-Nva-αAzaNle-OEt,
(5) α-[1,2,3,4-tetrahydronaphthyl-2-methyl]-Lys-Nva-α-AzaNle-OEt,
(6) N-ethylcarbamoyl-phenylalanine-valine-norvalanine-leucinol,
(7) N-ethylcarbamoyl-phenylalanine-ornithine-norvaline-leucin- hydrazide, and
(8) N-ethylcarbamoyl-phenylalanine-valine-alanine-leucin-hydrazide, or a pharmaceutically acceptable salt thereof.

* * * * *

UNITED STATES PATENT AND TRADEMARK OFFICE
CERTIFICATE OF CORRECTION

PATENT NO. : 5,817,757                                    Page 1 of 2
DATED      : October 6, 1998
INVENTOR(S): A.D. Adams, et al It is certified that error appears in the above-identified patent and that said Letters Patent is hereby corrected as shown below:

On the title page, delete the title at Item 54, and substitute therefor, -- INHIBITORS OF PEPTIDE BINDING TO MHC CLASS II PROTEINS --.

In Column 68, Claim 1, line 66, delete the text of compound (50) and substitute therefor --
α-[3-Cyclohexylpropyl]-(ε–CBZ)Lys-Nva-α–AzaNle-OEt, --

In Column 69, Claim 1, line 1, delete the text of compound (51) and substitute therefor --
α-[3-Cyclohexylpropyl]-Lys-Nva-α–AzaNle-OEt, --

In Column 69, Claim 1, line 30, delete the text of compound (66) and substitute therefor --
N-E-α-methylcinnamyl-valine-alanine-leucinamide, --

In Column 69, Claim 2, line 38, delete the text of compound (2) and substitute therefor --
N-α-((2-Methyl-2-((3-cyclohexyl)propylamino))-propanoyl)-Nva-Leu-$NH_2$ , --

In Column 69, Claim 2, line 40, delete the text of compound (3) and substitute therefor --
N-α-((2-Methyl-2-((3-cyclohexyl)propylamino))-4-pentenoyl)-Nva-Leu-$NH_2$ , --

In Column 69, Claim 2, line 46, delete the text of compound (6) and substitute therefor --
N-α-((3-Cyclohexyl)propyl))-Nva-Nva-Leu-$NH_2$ , --

In Column 69, Claim 2, line 48, delete the text of compound (8) and substitute therefor --
α-[Cinnamoyl]-Lys-Nva-Leu-$NH_2$ , --

In Column 69, Claim 2, line 50, delete the text of compound (9) and substitute therefor --
α-[2-methylcinnamoyl]-Lys-Nva-Leu-$NH_2$ , --

In Column 69, Claim 2, line 52, delete the text of compound (10) and substitute therefor --
α-[3-methylcinnamoyl]-Lys-Nva-Leu-$NH_2$ , --

In Column 69, Claim 2, line 54, delete the text of compound (11) and substitute therefor --
α-[2-Phenylcyclopropyl-1-carbonyl]-Lys-Nva-Leu-$NH_2$ , --

In Column 69, Claim 2, line 56, delete the text of compound (12) and substitute therefor --
α-[2-Benzylcyclopropyl-1-carbonyl]-Lys-Nva-Leu-$NH_2$ , --

UNITED STATES PATENT AND TRADEMARK OFFICE
CERTIFICATE OF CORRECTION

PATENT NO. : 5,817,757
DATED : October 6, 1998
INVENTOR(S) : A.D. Adams, et al

It is certified that error appears in the above-identified patent and that said Letters Patent is hereby corrected as shown below:

In Column 70, Claim 2, line 1, delete the text of compound (13) and substitute therefor --
α-[1-Phenylcyclopropyl-1-carbonyl]-Lys-Nva-Leu-$NH_2$, --

In Column 70, Claim 2, line 3, delete the text of compound (14) and substitute therefor --
α-[(1R,2S)-2-Cyclohexylcyclopropyl-1-carbonyl]-Lys-Nva-Leu-$NH_2$, --

Signed and Sealed this

Second Day of February, 1999

Attest:

Attesting Officer

*Acting Commissioner of Patents and Trademarks*